United States Patent [19]

Kishimoto et al.

[11] Patent Number: 5,180,735

[45] Date of Patent: Jan. 19, 1993

[54] CYCLOHEXANOL DERIVATIVES, PRODUCTION AND USE THEREOF

[75] Inventors: Shoji Kishimoto, Takarazuka; Shogo Marui, Suita; Takeshi Fujita, Takarazuka, all of Japan

[73] Assignee: Takeda Chemical Industries, Ltd., Osaka, Japan

[21] Appl. No.: 575,559

[22] Filed: Aug. 29, 1990

[30] Foreign Application Priority Data

Aug. 31, 1989 [JP] Japan .................................. 1-226514
Mar. 8, 1990 [JP] Japan .................................. 2-57752

[51] Int. Cl.$^5$ ..................... A61K 31/38; C07D 307/80
[52] U.S. Cl. ..................... 514/443; 549/58;
549/52; 549/55; 549/56; 549/60; 549/551;
549/553; 549/554; 549/561; 549/562; 544/147;
544/238; 544/339; 544/246; 544/241; 544/374;
544/408; 544/409; 544/336; 544/235; 544/234;
544/242; 544/168; 544/171; 544/174; 546/159;
546/153; 546/207; 546/286; 514/231.5;
514/432; 514/444; 514/475; 514/825; 514/866;
514/863; 514/336; 514/252; 514/422; 514/314;
548/517; 548/518; 548/527
[58] Field of Search ................... 549/13, 19, 52, 55,
549/56, 60, 332, 551, 553, 561, 562, 554, 58;
544/147, 238, 339, 246, 241, 374, 408, 409, 316,
336, 235, 234, 242, 171, 168, 174; 514/231.5,
443, 444, 432, 475, 825, 866, 863, 336, 252, 422,
314, 326, 331, 269, 256; 546/280, 207, 153, 155,
159; 548/518, 527, 517

[56] References Cited

U.S. PATENT DOCUMENTS 4,954,496 9/1990 Oka et al. ........................... 549/553

FOREIGN PATENT DOCUMENTS 325199 7/1989 European Pat. Off. ............. 549/332
354767 2/1990 European Pat. Off. ............. 549/551
354787 2/1990 European Pat. Off. ............. 549/551

OTHER PUBLICATIONS

Landquist, J. Chem. Soc., "Some Degradation Products of Fumagillin," pp. 4237–4245 (1956).

Primary Examiner—Richard L. Raymond
Assistant Examiner—Mark W. Russell
Attorney, Agent, or Firm—Gregory D. Williams; David G. Conlin

[57] ABSTRACT

The present invention relates to a compound of the formula:

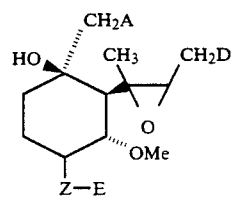

wherein A is halogen, $N(O)mR^1R^2$, $N^{\oplus}R^1R^2R^3 \cdot X^{\ominus}$, $S(O)nR^1$ or $S^{\oplus}(O)mR^1R^2 \cdot X^{\ominus}$ where $R^1$, $R^2$ and $R^3$ are each optionally substituted hydrocarbon or heterocyclic group, $X^{\ominus}$ is a counter anion; m is an integer of 0 or 1; n is an integer of 0 to 2; $R^1$ and $R^2$ may form a nitrogen-containing or a sulfur-containing heterocyclic ring, which may further form a condensed ring, with the adjacent nitrogen atom or sulfur atom, and these nitrogen-containing or sulfur-containing heterocyclic rings may have substituents, Z is O or $NR^4$ where $R^4$ is hydrogen or an optionally substituted lower alkyl or aryl group, D is 2-methyl-1-propenyl group or isobutyl group, and E is hydrogen, an optionally substituted hydrocarbon or an optionally substituted acyl group; provided that, when A is chlorine, E is an optionally substituted hydrocarbon or acyl excepting dinitrobenzoyl, a salt thereof, production and use thereof.

The novel cyclohexanol derivatives of the present invention have angiogenesis inhibiting activity and antitumor activity, and they are used as antirheumatic agents, therapeutic agents of psoriasis, therapeutic agents of diabetic retinopathy and anti-tumor agents.

14 Claims, No Drawings

CYCLOHEXANOL DERIVATIVES, PRODUCTION AND USE THEREOF

TECHNICAL FIELD

This invention relates to novel cyclohexanol derivatives and their use.

BACKGROUND TECHNOLOGY

Angiogenesis is concerned with the occurrence of pathological processes of various inflammatory diseases (rheumatic diseases, psoriasis, etc.), diabetic retinopathy, tumors, etc. Therefore, it has been considered that inhibition of angiogenesis has a connection with therapy and prophylaxis of these diseases and several groups have searched for substances capable of inhibiting angiogenesis. For example,.mention is made of research works for application of Protamine by Taylor [Taylor, S, et al., Nature, 297, 307 (1982)] and for use of heparin in the presence of cortisone by Folkman et al. [Folkman, J. et al., Science, 221, 719 (1983)]. Furthermore, patent applications have been filed directed to ascorbic acid ether and its related compounds (JP-A-131978/1983) or polysaccharide sulfate DS4125 (JP-A-119500/1988) as compounds showing activity of inhibiting angiogenesis. However, the activities of these compounds are not sufficiently satisfactory, and compounds having more satisfactory activity are desired.

OBJECT OF THE INVENTION

The object of the present invention lies in providing novel compounds having an action of inhibiting angiogenesis and an anti-tumor action, whose toxicity to hosts is low.

To attain the above-mentioned object, the present inventors have conducted searches for various compounds. As a result, they found that cyclohexanol derivatives, chemically derived from fumagillol, a hydrolysate of fumagillin which has been known as an antibiotic agent and an antiprotozoal agent, have a superb action of inhibiting angiogenesis and an antitumor action, and that they are less toxic to hosts, thus the present invention has been accomplished.

SUMMARY OF THE INVENTION

More specifically, the present invention is directed to a compound and a method of producing the compound, wherein the compound is represented by the formula:

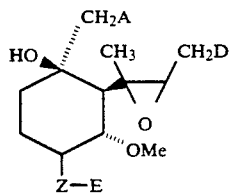

wherein A is halogen, $N(O)mR^1R^2$, $N^{\oplus}R^1R^2R^3.X^{\ominus}$, $S(O)nR^1$ or $S^{\oplus}(O)mR^1R^2.X^{\ominus}$ (where $R^1$, $R^2$ and $R^3$ are each optionally a substituted hydrocarbon group or a heterocyclic group, $X^{\oplus}$ is a counter anion; m is an integer of 0 or 1; n is an integer of 0 to 2; $R^1$ and $R^2$ may form a nitrogen-containing or a sulfur-containing heterocyclic ring, which may further form a condensed ring, with the adjacent nitrogen atom or sulfur atom, and these nitrogen-containing or sulfur-containing heterocyclic rings may have substituents); Z is O or $NR^4$ (where R is hydrogen or an optionally substituted lower alkyl or aryl group); D is 2-methyl-1-propenyl group or isobutyl group; and E is hydrogen, an optionally substituted hydrocarbon group or an optionally substituted acyl group; provided that, when A is chlorine, E is an optionally substituted hydrocarbon group or acyl excepting dinitrobenzoyl, or a salt thereof.

The present invention is also directed to an antitumor agent containing a compound represented by the formula:

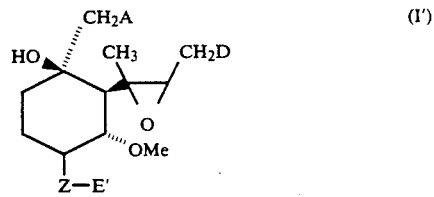

wherein A is halogen, $N(O)mR^1R^2$, $N^{\oplus}R^1R^2R^3.X^{\ominus}$, $S(O)nR^1$ or $S^{\oplus}(O)mR^1R^2.X^{\ominus}$ (where $R^1,R^2$ and $R^3$ are each optionally substituted hydrocarbon group or heterocyclic group, $X^{\ominus}$ is a counter anion; m is an integer of 0 or 1; n is an integer of 0 to 2; $R^1$ and $R^2$ may form a nitrogen-containing or a sulfur-containing heterocyclic ring, which may further form a condensed ring, with the adjacent nitrogen atom or sulfur atom, and these nitrogen-containing or sulfur-containing heterocyclic rings may have substituents); Z is O or $NR^4$ (where $R^4$ is hydrogen or an optionally substituted lower alkyl or aryl group); D is 2-methyl-1-propenyl group or isobutyl group; and E' is hydrogen, an optionally substituted hydrocarbon group or an optionally substituted acyl group, or a salt thereof.

DETAILED DESCRIPTION OF THE INVENTION

In the above-mentioned formulae (I) and (I'), the halogen shown by A includes fluorine, chlorine, bromine and iodine.

Examples of the hydrocarbon groups of the optionally substituted hydrocarbon groups shown by $R^1$, $R^2$ or $R^3$ include straight-chained or branched $C_{1-6}$ alkyl groups (e.g. methyl, ethyl, propyl, isopropyl, butyl, isobutyl, sec-butyl, pentyl, isopentyl, hexyl, etc.), $C_{2-6}$ alkenyl groups (e.g. vinyl, allyl, 2-butenyl, methylallyl, 3-butenyl, 2-pentenyl, 4-pentenyl, 5-hexenyl, etc.), $C_{2-6}$ alkynyl groups (e.g. ethynyl, propargyl, 2-butyn-1-yl, 3-butyn2-yl, 1-pentyn-3-yl, 3-pentyn-1-yl, 4-pentyn-2-yl, 3-hexyn-1-yl, etc.), $C_{3-6}$ cycloalkyl groups (e.g. cyclopropyl, cyclobutyl, cyclopentyl, cyclohexyl, etc.), $C_{3-6}$ cycloalkenyl groups (e.g. cyclobutenyl, cyclopentenyl, cyclohexenyl, cyclohexadienyl, etc.), $C_{7-13}$ aralkyl groups (e.g. benzyl, 1-phenethyl, 2-phenethyl, etc.), and $C_{6-10}$ aryl groups (e.g. phenyl, naphthyl, etc.).

Examples of the heterocyclic groups of the optionally substituted heterocyclic groups shown by $R^1$, $R^2$ or $R^3$ include 5- or 6-membered heterocyclic groups containing 1 to 4 hetero-atoms such as nitrogen, oxygen, sulfur,. etc. (e.g. 2-furyl, 2-thienyl, 4-thiazolyl, 4-imidazolyl, 4-pyridyl, 1,3,4-thiadiazol-2-yl, 1-methyl-5-tetrazolyl, etc.). These heterocyclic groups may form bicyclic condensed rings by condensation with 5- or 6-membered ring such as benzene, pyridine, cyclohexane, etc. (e.g. 8-quinolyl, 8-purinyl, etc.)

Examples of the nitrogen-containing heterocyclic groups which may be formed by $R^1$ and $R^2$ together with the adjacent nitrogen atom include 4- to 7-membered nitrogen-containing heterocyclic groups (e.g. pyrrolidin-1-yl, piperazino, morpholino, 4-methylpiperazin-1-yl, etc.).

Examples of the sulfur-containing heterocyclic groups which may be formed by $R^1$ and $R^2$ together with the adjacent sulfur atom include 4- to 7-membered sulfur-containing heterocyclic groups (e.g. tetrahydrothiophen-1-yl, 1,4-thioxan-1-yl, etc.).

The nitrogen-containing or sulfur-containing heterocyclic groups which may be formed by $R^1$ and $R^2$ together with the adjacent nitrogen atom or sulfur atom may be condensed with a 5- or 6-membered cyclic group (e.g. benzene, pyridine, pyrazine, pyridazine, cyclohexane, cyclohexene, etc.) to form bicyclic condensed rings (e.g. isoindolin-2-yl, 2-isoquinolyl, 1,3-dihydrobenzo[c]thiophen-2-yl, 2,3-dihydrobenzo[b]thiophen-1-yl, 1,3,3a,4,7,7a-hexahydrobenzo[c]thiophen-2-yl, perhydrobenzo[c]thiophen-2-yl, 3,4-dihydro-1H-2-benzopyran-2-yl, 3,4-dihydro-2H-1-benzopyran-1-yl, 1,2,4,5-tetrahydro-3-benzothiepin-3-yl, 1,3-dihydrothieno[3,4-c]pyridin-2-yl, 5,7-dihydrothieno[3,4-b]pyrazin-6-yl, 5,7dihydrothieno[3,4-d]pyridazin-6-yl, etc.)

Examples of the lower alkyl groups of the optionally substituted lower alkyl groups shown by $R^4$ include $C_{1-6}$ alkyl groups (e.g. methyl, ethyl, propyl, isopropyl, butyl, isobutyl, sec-butyl, pentyl, isopentyl, hexyl, etc.).

As the aryl groups of the optionally substituted aryl groups shown by $R^4$, mention is made of $C_{6-10}$ aryl groups (e.g. phenyl, naphthyl, etc.).

As the optionally substituted hydrocarbon groups shown by E or E', mention is made of those specifically described above as the optionally substituted hydrocarbon groups shown by $R^1$, $R^2$ and $R^3$.

As the optionally substituted acyl groups shown by E or E', mention is made of the residues of acids such as carboxylic acid acyl, sulfonic acid acyl, carbamoyl, thiocarbamoyl, sulfamoyl, etc., and examples of them include respectively optionally substituted alkanoyl, aroyl, heterocyclic carbonyl, carbamoyl, thiocarbamoyl, arylsulfonyl, alkylsulfonyl, sulfamoyl, alkoxycarbonyl, aryloxycarbonyl, etc.

As the alkanoyl groups of the above-mentioned optionally substituted alkanoyl groups, mention is made of $C_{1-10}$ alkanoyl groups (e.g. formyl, acetyl, propionyl, isopropionyl, butyryl, pentanoyl, hexanoyl, etc.).

As the aroyl groups of the optionally substituted aroyl groups, mention is made of $C_{7-10}$ aroyl groups (e.g. benzoyl, 1-naphthoyl, 2-naphthoyl, etc.).

As the heterocyclic carbonyl groups in the optionally substituted heterocyclic carbonyl groups, mention is made of 5- or 6-membered heterocyclic carbonyl groups containing 1 to 4 hetero-atoms such as nitrogen, oxygen, sulfur, etc. (e.g. 2-furoyl, 2thenoyl, nicotinoyl, isonicotinoyl, etc.).

As the arylsulfonyl groups of the optionally substituted arylsulfonyl groups, mention is made of $C_{6-10}$ arylsulfonyl groups (e.g. benzenesulfonyl, 2-naphthylsulfonyl, etc.).

As the alkylsulfonyl groups of the optionally substituted alkylsulfonyl groups, mention is made of $C_{1-6}$ alkylsulfonyl groups (e.g. methylsulfonyl, ethylsulfonyl, etc.).

As the alkoxycarbonyl groups of the optionally substituted alkoxycarbonyl groups, mention is made of $C_{2-7}$ alkoxycarbonyl groups (e.g. methoxycarbonyl, ethoxycarbonyl, isobutoxycarbonyl, etc.).

As the aryloxycarbonyl groups of the optionally substituted aryloxycarbonyl groups, mention is made of $C_{7-11}$ aryloxycarbonyl groups (e.g. phenoxycarbonyl, 1-naphthyloxycarbonyl, 2-naphthyloxycarbonyl, etc.

The respectively optionally substituted hydrocarbon groups or heterocyclic groups shown by $R^1$, $R^2$ or $R^3$, the nitrogen-containing or sulfur-containing heterocyclic groups which may be formed by $R^1$ and $R^2$ together with the adjacent nitrogen atom or sulfur atom and may form condensed ring, the respectively optionally substituted lower alkyl groups or aryl groups shown by $R^4$, and the respectively optionally substituted hydrocarbon groups or acyl groups (e.g. alkanoyl group, aroyl group, heterocyclic carbonyl group, carbamoyl group, thiocarbamoyl group, arylsulfonyl group, alkylsulfonyl group, sulfamoyl group, alkoxycarbonyl group or aryloxycarbonyl group) shown by E or E' may have 1 to 3 substituents at any positions possibly substituted.

Examples of these substituents include $C_{1-6}$ alkyl groups (e.g. methyl, ethyl, propyl, isopropyl, butyl, sec-butyl, pentyl, isopentyl, hexyl, etc.), $C_{2-6}$ alkenyl groups (e.g. vinyl, allyl, 2-butenyl, methylallyl, 3-butenyl, 2-pentenyl, 4-pentenyl, 5-hexenyl, etc.), $C_{2-6}$ alkynyl groups (e.g. ethynyl, propargyl, 2-butyn-1-yl, 3-butyn-2-yl, 1-pentyn-3-yl, 3-pentyn-1-yl, 4-pentyn-2-yl, 3-hexyn-1-yl, etc.), $C_{3-6}$ cycloalkyl groups (cyclopropyl, cyclobutyl, cyclopentyl, cyclohexyl, etc.), $C_{3-6}$ cycloakenyl groups (e.g. cyclobutenyl, cyclopentenyl, cyclohexenyl, cyclohexadienyl, etc.), $C_{6-10}$ aryl groups (e.g. phenyl, naphthyl, etc.), amino, $C_{1-6}$ alkylamino groups (e.g. methylamino, ethylamino, isopropylamino, etc.), di$C_{1-6}$ alkylamino groups (e.g. dimethylamino, diethylamino, etc.), azido, nitro, halogen (e.g. fluorine, chlorine, bromine, iodine, etc.), hydroxyl, $C_{1-4}$ alkoxy groups (e.g. methoxy, ethoxy, etc.), $C_{6-10}$ aryloxy groups (e.g. phenoxy, naphthyloxy, etc.), $C_{1-6}$ alkylthio groups (e.g. methylthio, ethylthio, propylthio, etc.), $C_{6-10}$ arylthio groups (e.g. phenylthio, naphthylthio, etc.), cyano, carbamoyl groups, carboxyl groups, $C_{1-4}$ alkoxycarbonyl groups (e.g. methoxycarbonyl, ethoxycarbonyl, etc.), $C_{7-11}$ aryloxycarbonyl groups (e.g. phenoxycarbonyl), 1-naphthyloxycarbonyl, 2-naphthyloxycarbonyl, etc.), carboxy $C_{1-4}$ alkoxy groups (e.g. carboxymethoxy, 2-acetyl, propionyl, isopropionyl, butyryl, pentanoyl, hexanoyl, etc.), $C_{7-11}$ aroyl groups (e.g. benzoyl, 1-naphthoyl, 2-naphthoyl, etc.), $C_{1-6}$ arylsulfonyl groups (e.g. benzenesulfonyl, 1-naphthylsulfonyl, 2naphthylsulfonyl, etc.), $C_{7-11}$ alkylsulfinyl groups (e.g. methylsulfinyl, ethylsulfinyl, etc.), $C_{6-10}$ arylsulfinyl groups (e.g. benzenesulfinyl, 1-naphthylsulfinyl, 2-naphthylsulfinyl, etc.), $C_{1-6}$ alkylsulfonyl groups (e.g. methylsulfonyl, ethylsulfonyl, etc.), 5- or 6-membered heterocyclic groups containing 1–4 hetero-atoms such as nitrogen, oxygen, sulfur, etc. (e.g. 2-furyl, 2-thienyl, 4-thiazolyl, 4-imidazolyl, 4-pyridyl, 1,3,4-thiadiazol-2-yl, 1-methyl-5-tetrazolyl, etc.), 5- or 6-membered heterocyclic carbonyl groups containing 1 to 4 heteroatoms such as nitrogen, oxygen, sulfur, etc. (e.g. 2-furoyl, 2-thenoyl, nicotinyl, isonicotinyl, etc.), and 5- or 6-membered heterocyclic this groups containing 1 to 4· hetero-atoms such as nitrogen, oxygen, sulfur, etc., (e.g. 4-pyridylthio, 2-pyrimidylthio, 1,3,4-thiadiazol-2-ylthio, 1-methyl-5-tetrazolylthio, etc.) and the heterocyclic thio groups may be fused with benzene ring to form bicyclic condensed ring thio groups (e.g. 2-benzothiazolylthio, 8-quinolylthio, etc.). And, when E or E' each stands for di-substituted carbamoyl group, thiocarbamoyl group or sulfamoyl group, it may form, taken together with the nitrogen atom of the carbamoyl group, thiocarbamoyl group or sulfamoyl group, a nitrogen-containing heterocyclic group (e.g. pyrrolidin-1-yl, piperidino, morpholino, piperazin-1-yl, 4-methyl-piperazin-1-yl, 4-phenylpiperazin-yl, etc.

And, the substituents in the respectively optionally substituted hydrocarbon groups or heterocyclic groups shown by $R^1$, $R^2$ or $R^3$, the substituents in the nitrogen-containing or sulfur-containing heterocyclic groups, which may be formed by $R^1$ and $R^2$ together with adjacent nitrogen atom or sulfur atom, which may further form condensed ring, the substituents in the respectively optionally substituted lower alkyl groups or aryl groups shown by $R^4$, and the substituents in the respectively optionally substituted hydrocarbon groups, alkanoyl groups, aroyl groups, heterocyclic carbonyl groups, carbamoyl groups, thiocarbamoyl groups, aryl sulfonyl groups, alkyl sulfonyl groups, sulfamoyl groups, alkoxy carbonyl groups or aryloxy carbonyl groups, which are shown by E or E', may further have 1 to 3 substituents at their substitutive positions.

As these substituents, use is made of those as exemplified by the substituents in the respectively optionally substituted hydrocarbon groups or heterocyclic groups shown by $R^1$, $R^2$ or $R^3$, the substituents in the nitrogen-containing or sulfur-containing heterocyclic groups, which may be formed by $R^1$ and $R^2$ together with adjacent nitrogen atom or sulfur atom, which may further form condensed ring, the substituents in the respectively optionally substituted lower alkyl groups or aryl groups shown by $R^4$, and the substituents in the respectively optionally substituted hydrocarbon groups, alkanoyl groups, aroyl groups, heterocyclic carbonyl groups, carbamoyl groups, thiocarbamoyl groups, aryl sulfonyl groups, alkyl sulfonyl groups, sulfamoyl groups, alkoxy carbonyl groups or aryloxy carbonyl groups, which are shown by E or E', as they are.

Examples of the counter anion shown by $X^\ominus$ include halogen ion (e.g. iodide ion, bromide ion, chloride ion, etc.), sulfate ion, phosphate ion, nitrate ion, perchlorate ion, tetrafluoroborate ion, methanesulfonate ion, p-tolylsulfate ion, benzenesulfate ion, hydroxyl ion, carboxyl ion of organic acid (oxalate ion, maleate ion, fumarate ion, succinate ion, citrate ion, lactate ion, trifluoroacetate ion, lactobionate ion, acetate ion, propionate ion, tartrate ion, ethyl succinate ion, etc.).

While the compound (I) or (I') has an asymmetric center in the molecule and has optical activity, its absolute structure is based on fumagillol employed as the starting material. This means that the absolute structure is in agreement with that of fumagillol. In the description of manner of linkage of the substituents on the cyclohexane ring, "'''''" shows αlinkage, "—" show β-linkage, and "⬛" shows the case where the linkage may be either α-type or β-type.

When the compound of this invention has, in its molecule, an acid substituent (e.g. carboxyl, etc.) or a basic substituent (e.g. amino, a lower alkylamino, a di-lower alkylamino, a nitrogen-containing heterocyclic group, etc.), it can be used as a physiologically acceptable salt as well. Examples of the physiologically acceptable salt include salts with inorganic bases, salts with organic bases, and salts with basic or acid amino acids. Examples of inorganic bases include alkali metals (e.g. sodium, potassium, etc.) and alkaline earth metals (e.g. calcium, magnesium, etc.), examples of organic bases include trimethylamine, triethylamine, pyridine, picoline, N,N-dibenzylethylenediamine, ethanolaiine, diethanolamine, tris-hydroxymethylaminomethane, dicyclohexylamine, etc., examples of inorganic acids include hydrochloric acid, hydrobromic acid, sulfuric acid, nitric acid, phosphoric acid, etc., examples of organic acids include formic acid, acetic acid, trifluoroacetic acid, oxalic acid, tartaric acid, fumaric acid, maleic acid, methanesulfonic acid, benzenesulfonic acid, p-toluenesulfonic acid, and examples of basic or acid amino acids include arginine, lysine, ornithine, aspartic acid, glutamic acid, etc. Among these salts, those with bases (i.e. salts with inorganic bases, salts with organic bases, salts with basic amino acids) include salts which can be formed with the carboxyl group in the substituents of the compound (I) and (I'), and salts with acids (i.e. salts with inorganic acids, salts with organic acids, salts with acid amino acids) include salts which can be formed with amino group, a lower alkylamino group, di-lower alkylamino group, a nitrogen-containing heterocyclic group, etc. in the substituents of the compound (I).

And, when the compound (I) and (I') have intramolecularly a di-lower alkylamino group, a nitrogen-containing heterocyclic group or a nitrogen-containing aromatic heterocyclic group, the nitrogen atom in these substituents may further be alkylated to form a quaternary ammonio group (e.g. trimethylammonio, N-methylpyridinio, N-methylpyrrolidin-1-ylio, etc.), and, as the counter anion, mention is made of counter anion similar to that shown by the afore-mentioned $X^\ominus$ In the compound (I) and (I'), A is preferably $S^\oplus(O)mR^1R^2.X^\ominus$ (where $R^1$, $R^2$ and R: are each optionally a $N(O)mR^1R^2$, $N^\oplus R^1R^2R^3.X^\ominus$, $S(O)nR^1$ and $S^\oplus(O)mR^1R^2.X^\ominus$, especially $S^\oplus R^1R^2.X^\ominus$ wherein $R^1$ and $R^2$ are hydrocarbon group and $X^\ominus$ is halogen.

As B, O or NH is preferable, as D, 2-methyl-1-propenyl is preferable, and, as E or E', substituted carbamoyl is preferable.

The compound of this invention represented by the general formula (I) can be produced by employing, as the starting material, fumagillol, which is the hydrolysate of fumagillin produced by microorganism, [Tarbell, D. S. et al., (J. Am. Chem. Soc.) 83, 3096 (1961)]. The production method is described in detail as follows.

A compound of formula (I), wherein the manner of linkage of the cyclohexane ring with B is β-type, B is O and D is 2-methyl-1-isopropenyl, can be produced as the intermediates or the end products shown by (IV)~(XIII) by conducting the reaction shown by the following scheme 1.

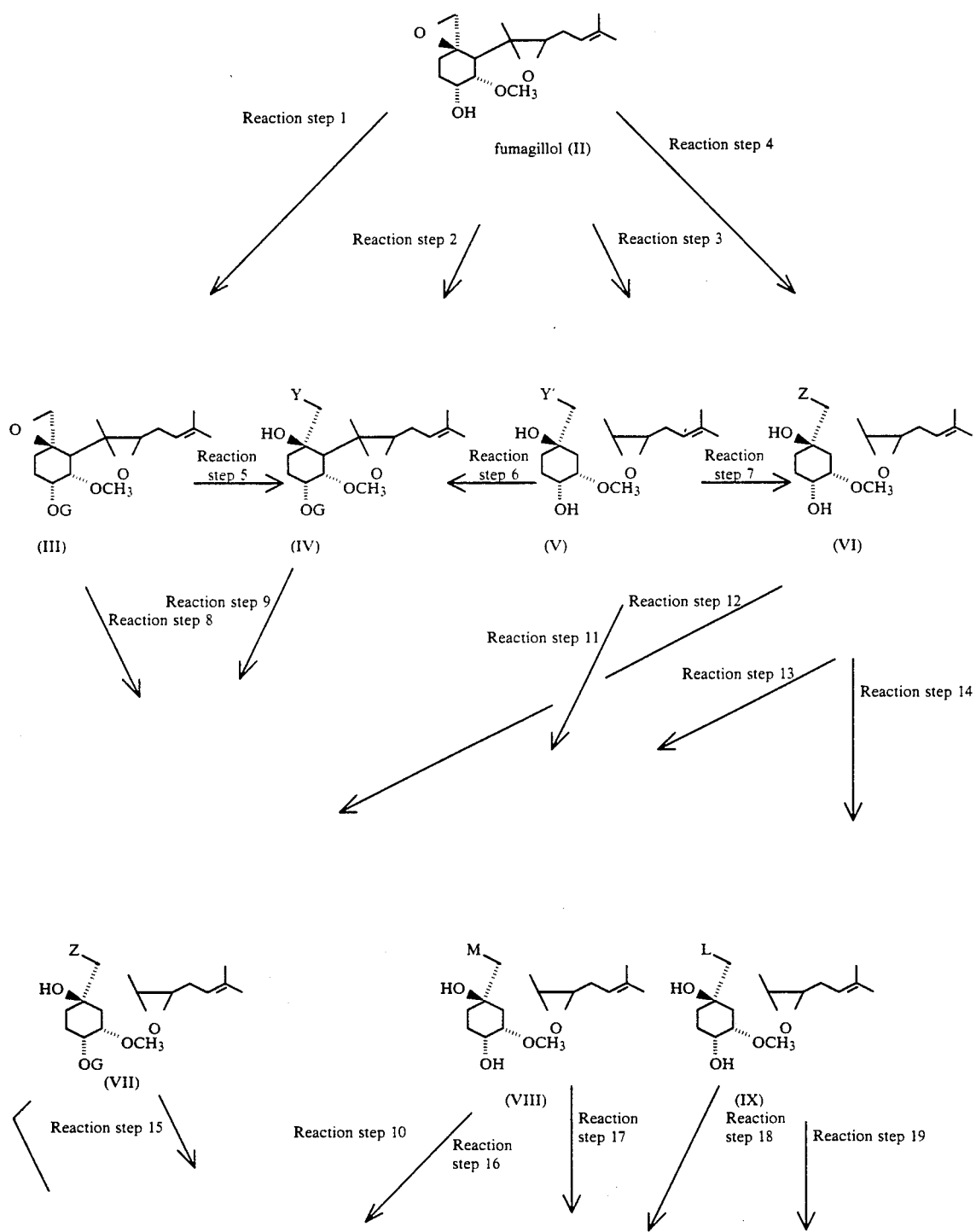

-continued
(Scheme 1)

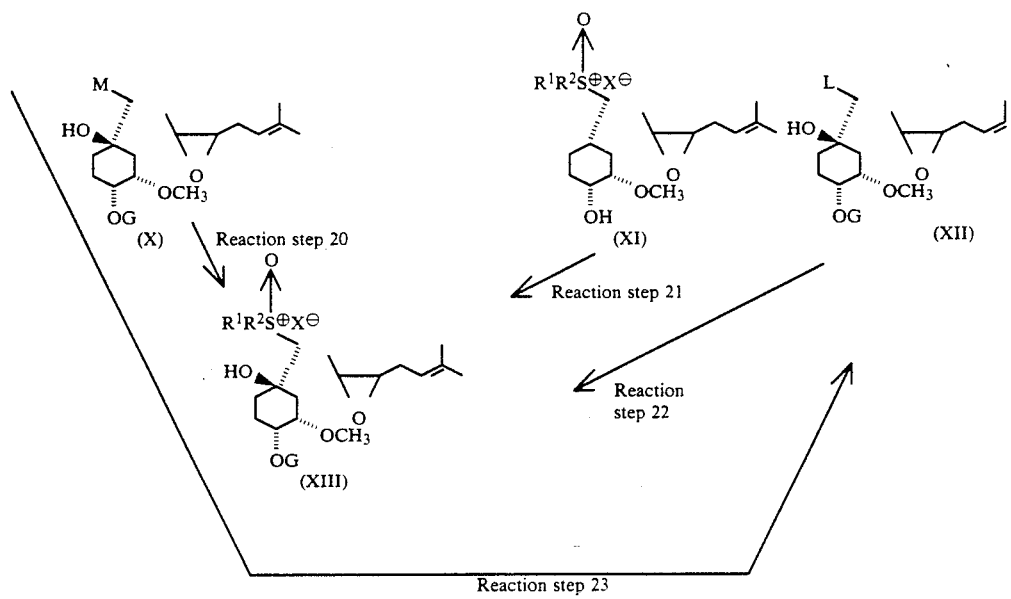

And, in the above scheme 1, G stands for an optionally substituted hydrocarbon group or an optionally substituted acyl group; Y stands for halogen; Y' stands for halogen excepting chloride; Z stands for $NR^1R^2$ or $SR^1$; L stands for $(O)_lR^1R^2$ or $S(O)_lR^1$ (wherein l denotes 1 or 2); M stands for $N^{\oplus}R^1R^2R^3.X^{\ominus}$ or $S^{\oplus}R^1R^2.X^{\ominus}$; $R^1 \sim R^3$ and $X^{\ominus}$ are of the same meaning as defined for those in the general formula (I): provided that when Y is chlorine, G stands for an optionally substituted hydrocarbon group or an optionally substituted acyl group excepting dinitrobenzoyl.

A compound of formula (I), wherein the manner of linkage of the cyclohexane ring with B is β-type, B is $NR^4$ and D is 2-methyl-1-isopropenyl, can be produced as the intermediates or the end products shown by (XIX)~(XX) by conducting the reaction shown by the following scheme 2.

(Scheme 2)

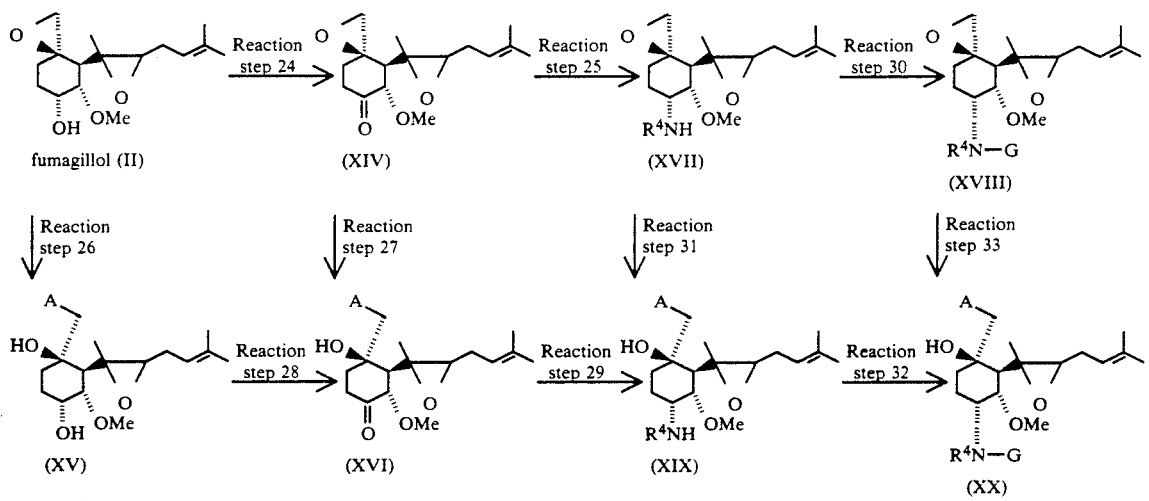

And, in the above scheme 2, A and $R^4$ are of the same meaning as those in the general formula (I); and G is of the same meaning as defined for g in the scheme 1.

A compound of formula (I), wherein the manner of linkage of the cyclohexane ring with B is α-type, B is O and D is 2-methyl-1-isopropenyl, can be produced as the intermediates or the end products (XXIII)~(XXIV) by the reaction shown by the scheme 3.

(Scheme 3)

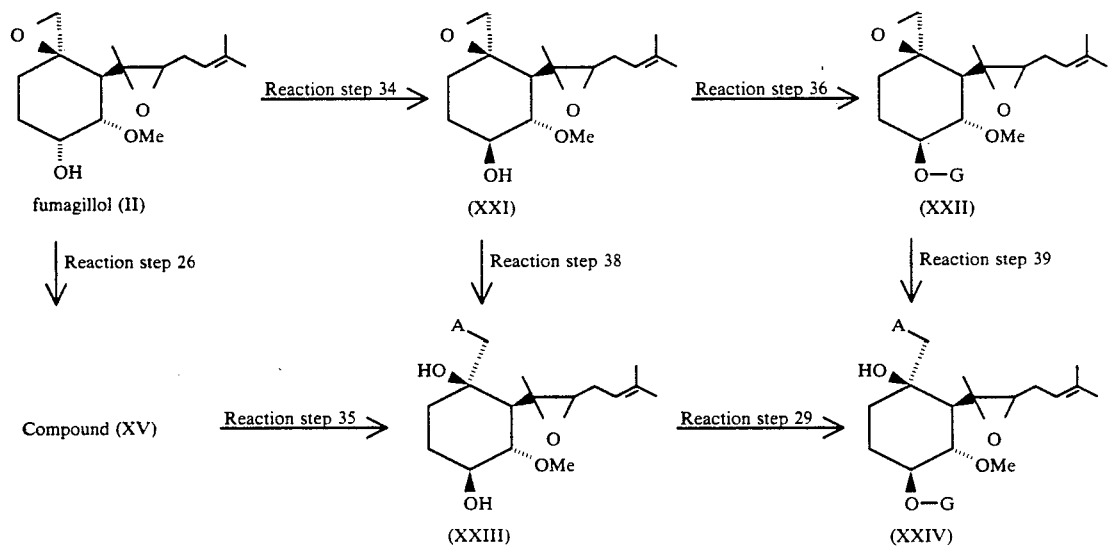

And, in the above scheme 3, A is of the same meaning as defined for A in the general formula (I), and G is of the same meaning as defined for G in the scheme 1.

A compound of formula (I), wherein the manner of linkage of the cyclohexane ring with B is α-type, B is $NR^4$ and D is 2-methyl-1-isopropenyl, can be produced as the intermediates or the end products (XXIX)~(XXXII) by the reaction shown by the scheme 4.

(Scheme 4)

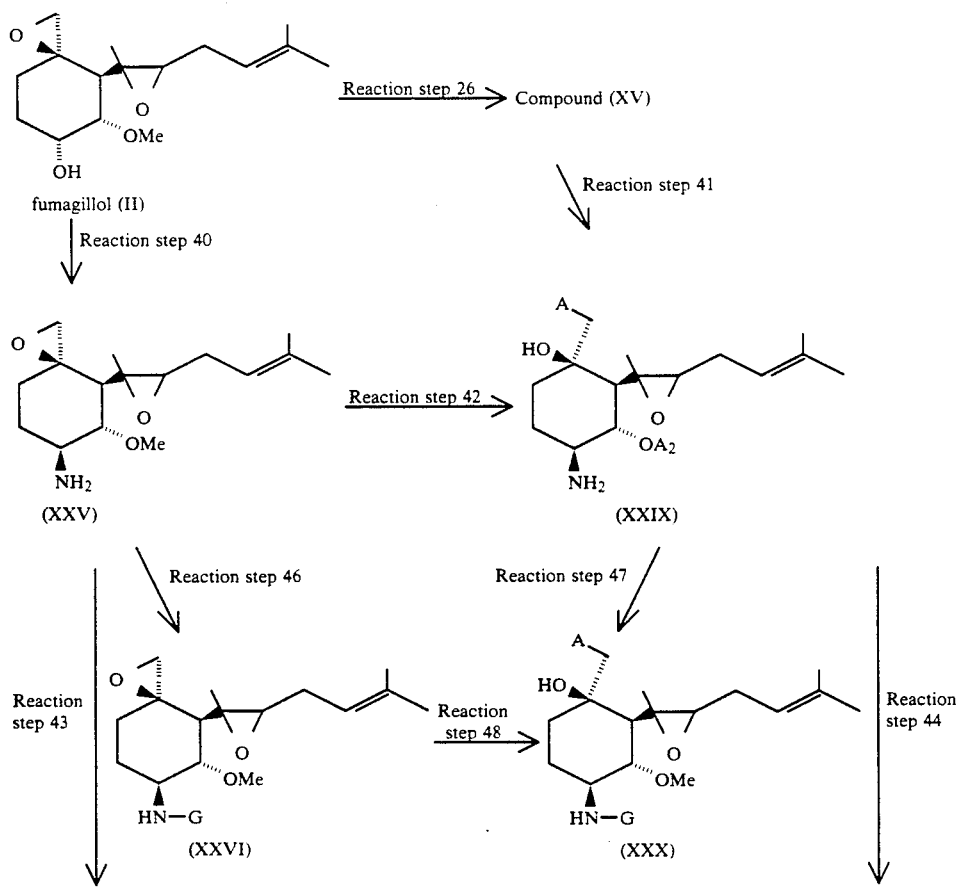

-continued
(Scheme 4)

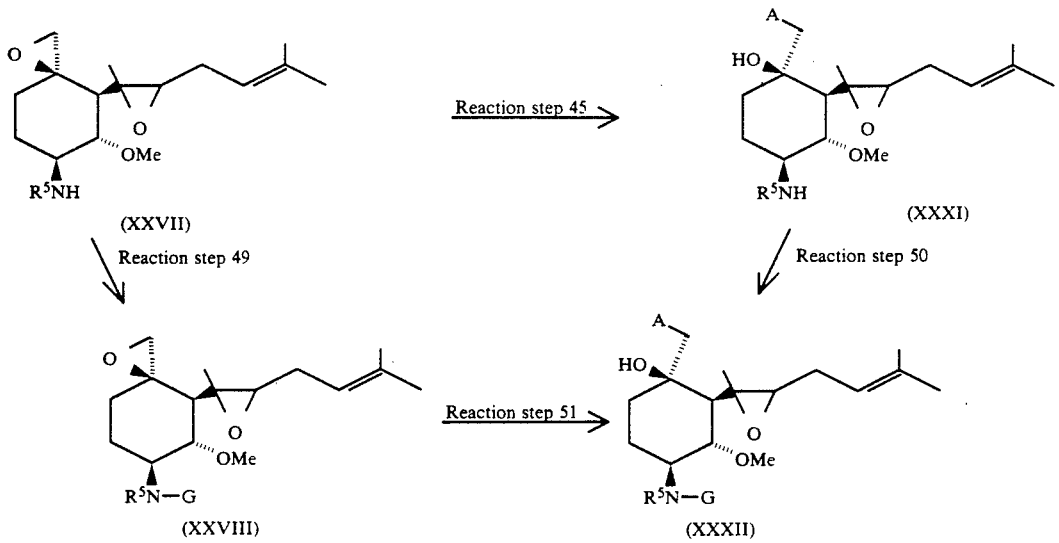

And, in the above scheme 4, A is of the same meaning as defined for A in the general formula (I), G is of the same meaning as defined for G in the scheme 1 and $R^5$ is an optionally substituted lower alkyl or aryl group.

A compound of formula (I), wherein D is isobutyl, can be produced by conducting catalytic reduction at an appropriate stage in the above-mentioned schema 1~4. For example, in scheme 1, the catalytic reduction can be conducted at step 1 by platinum catalysts.

As the catalytic reduction, for example, a method similar to the catalytic reduction of fumagillol by Tarbell et al. [Tarbell, D. S. et al., J. Am. Chem. Soc., 83, 3096 (1961)] can be employed.

The reactions shown in the above schema 1 to 4 are individually described in more detail hereinbelow.

Reaction step 1: Production of the compound (III) from fumagillol (II)

Compound (III) in scheme 1 can be produced by subjecting fumagillol (II) to alkylation, acylation, carbamoylation, thiocarbamoylation, sulfonylation or hydroxycarbamoylation.

Detail description on the alkylation, acylation, carbamoylation, thiocarbamoylation, sulfonylation and hydroxycarbamoylation is as follows.

1) Alkylation

This alkylation is conducted by allowing fumagillol to react with an alkylating agent such as alkyl halide (e.g. methyl iodide, ethyl iodide, benzyl bromide, allyl bromide, propargyl bromide, etc.), dialkyl sulfate (dimethyl sulfate, diethyl sulfate, etc.), etc.

This alkylating agent is employed in an amount of usually about 1 to 5 times as much mol. relative to 1 mol. of fumagillol.

This reaction is conducted usually in the presence of a base. As the base, use is made of alkali metal hydrogencarbonates (e.g. sodium hydrogencarbonate, potassium hydrogencarbonate, etc.), alkali metal carbonates (e.g. sodium carbonate, potassium carbonate, etc.), alkali metal hydrides (e.g. sodium hydride, potassium hydride, etc.), or organic metals (e.g. butyl lithium, lithium diisopropylamide, etc.). The amount of the base to be added ranges usually from about 1 to about 5 times as much mol. relative to 1 mol. of fumagillol.

This reaction is carried out usually in an organic solvent which does not exert undesirable influence on the reaction. Examples of such organic solvents as above include amides (e.g. dimethylformamide, dimethylacetamide, etc.), halogenated hydrocarbons (e.g. dichloromethane, chloroform, 1,2-dichloroethane, etc.), ethers (e.g. diethyl ether, tetrahydrofuran, dioxane, etc.), esters (e.g. methyl acetate, ethyl acetate, isobutyl acetate, methyl propionate, etc.), nitriles (e.g. acetonitrile, propionitrile, etc.), nitro compounds (e.g. nitromethane, nitroethane, etc.), ketones (e.g. acetone, methyl ethyl ketone, etc.), aromatic hydrocarbons (e.g. benzene, toluene, etc.), aliphatic saturated hydrogencarbonates (e.g. pentane, hexane, cyclohexane, etc.), etc., and these solvents may be used singly or as a mixture of two or more species of them in a suitable ratio.

While the reaction temperature varies with the amounts, kinds, etc. of alkylating agents, bases and solvents, it ranges from −80° C. to 100° C., preferably from 0° C. to 80° C. The reaction time ranges from about 20 minutes to about 5 days depending on numerous factors such as temperature.

2) Acylation

This acylation is conducted by allowing a reactive derivative of activated carboxylic acid, such as acid anhydride, acid halide, activated amide, activated ester, activated thioester, etc. to react with fumagillol.

These reactive derivatives are specifically described as follows.

i) Acid halide:

For example, acid chloride, acid bromide, etc. are employed.

ii) Acid anhydride:

For example, symmetric acid anhydrides, mixed acid anhydrides with a lower alkyl carbonate, etc. are employed.

iii) Active amide:

For example, amides with pyrazole, imidazole, 4-substituted imidazole, dimethyl pyrazole, benzotriazole, etc. are employed.

iv) Active ester:

For example, besides esters such as methoxymethyl ester, benzotriazole ester, 4-nitrophenyl ester, 2,4-dinitrophenyl ester, trichlorophenyl ester, pentachlorophenyl ester, etc., are employed esters with 1-hydroxy-1H-2-pyridone, N-hydroxysuccinimide, N-hydroxyphthalimide, etc.

v) Active thioester:

For example, thioesters with heterocyclic thiol such as 2-pyridyl thiol, 2-benzothiazolyl thiol, etc. are employed.

A reaction derivative of the carboxylic acid is employed in an amount of usually about 1 to 10 times as much mol., preferably 1 to 5 times as much mol., relative to 1 mol. of fumagillol. And, in case of using the carboxylic acid as its free state, the reaction is conducted preferably in the presence of a condensing agent. As the condensing agent, use is made of, for example, N, N'-dicyclohexylcarbodiimide, N-cyclohexyl-N'-morpholinoethylcarbodiimide, N-cyclohexyl-N'-(4-diethylaminocyclohexyl) (4-diethylaminocyclohexyl)carbodiimide, N-ethyl-N'-(3-dimethylaminopropyl)-carbodiimide, diphenylphospholylazide, diethyl cyanophosphate, etc.

This reaction is carried out usually in the presence of a base. As the base, use is made of the bases mentioned in the description of the alkylation, and the amount to be added ranges from about 1 mol. to 10 times as much mol. relative to 1 mol. of fumagillol.

This reaction is carried out usually in an organic solvent which does not exert undesirable influence on the reaction. As such organic solvents, use is made of those mentioned in the description of the alkylation.

The reaction temperature varies with the amount, kinds, etc. of carboxylic acid derivatives, bases and solvents, but it ranges from $-80°$ C. to $100°$ C., preferably from $0°$ C. to $80°$ C. The reaction time ranges from about 30 minutes to about 5 days.

3) Carbamoylation

Carbamoylation for introducing a mono-substituted carbamoyl group is carried out by usually allowing isocyanate to react with fumagillol.

This isocyanate is used in an amount of usually about 1 mol. to about 5 times as much mol. relative to 1 mol. of fumagillol.

This reaction may be conducted in the presence of a base. As the base, use is made of bases mentioned in the description of the alkylation in an amount ranging from about 1 mol. to 10 times as much mol. relative to 1 mol. of fumagillol.

This reaction is carried out usually in an organic solvent which does not exert undesirable influence on the reaction. As such organic solvents as above, use is made of those mentioned in the description of the alkylation.

The reaction temperature varies with the amounts and kinds of isocyanate, the base and the solvent then employed, and it usually ranges from about $-80°$ C. to $100°$ C., preferably from $0°$ C. to $80°$ C. The reaction time ranges from about one hour to about five days.

Among the compounds having mono-substituted carbamoyl group thus obtained, compounds having, for example, chloroacetyl carbamoyl, trichloroacetyl carbamoyl, etc., can be converted to compounds having carbamoyl group by removing chloroacetyl group or trichloroacetyl group by a conventional process (e.g. at room temperatures or elevated temperatures under basic conditions).

The said carbamoylation can also be conducted by allowing fumagillol to react with carbamoyl halide.

The said carbamoyl halide is used in an amount usually ranging from 1 mol. to 5 times as much mol. relative to 1 mol. of fumagillol.

This reaction is carried out usually in the presence of a base. As the base, use is made of bases mentioned in the description of the alkylation, and the amount of the base to be added ranges usually from about 1 mol. to about 10 times as much mol. relative to 1 mol. of fumagillol.

This reaction is carried out usually in an organic solvent which does not exert undesirable influence on the reaction. Examples of such organic solvents as above include those mentioned in the description of the alkylation.

The reaction temperature vary with the amounts and kinds of carbamoyl halide, bases and solvents, and it ranges from about $0°$ C. to around the reflux temperature of the reaction medium, preferably from about $25°$ C. to reflux temperature.

The said carbamoylation can also be carried out by allowing the 1,1-carbonyldiimidazole to react with the fumagillol to give an active ester, followed by allowing the ester to react with ammonia, primary amines (e.g. methylamine, ethylamine, isopropylamine, etc.), or secondary amine (e.g. dimethylamine, ethylmethylamine, dimethylamine, pyrrolidine, piperidine, N-methylpiperazine, morpholine, etc.).

1,1-Carbonyldiimidazole, ammonia, primary amines and secondary amines are employed in an amount ranging from usually 1 mol. to 5 times as much mol. relative to 1 mol. of fumagillol.

This reaction is carried out usually in an organic solvent which does not exert undesirable influence. As such organic solvents, use is made of those mentioned in the description of the alkylation.

While the reaction temperature varies with the amounts and kinds of ammonia, primary amines, secondary amines and solvents, it ranges from $-20°$ C. to the reflux temperature of the reaction medium, preferably from $0°$ C. to $50°$ C. The reaction time ranges from 20 minutes to about 5 days.

The active esters obtained as intermediates are included in the category of the compound (III).

Among the compound (III) wherein G is a mono-substituted carbamoyl group, a compound (III) wherein G is a substituted lower alkanoyl carbamoyl group can also be prepared by allowing a compound (III) wherein G is chloroacetyl carbamoyl to react with a nucleophilic reagent.

As the nucleophilic reagent, use is made of a lower carboxylic acid, a lower thiocarboxylic acid, thiols, amines and metal salts of them, and the amount of such reagent ranges usually from about 1 mol. to about 20 times as much mol. relative to 1 mol. of the starting compound, preferably from 1 mol. to 5 times as much mol.

This reaction is conducted usually in the presence of a base. As the base, use is made of those mentioned in the description of the alkylation, and its amount to be added ranges usually from about 1 mol. to 10 times as much mol. relative to 1 mol. of the starting compound.

This reaction is usually carried out in an organic solvent which does not exert undesirable influence on the reaction. As the organic solvents exerting no undesirable influence on the reaction, use is made of those mentioned in the description of the alkylation.

While the reaction temperature varies with the amounts, kinds, etc. of the nucleophilic reagents, bases and solvents, it ranges usually from −80° C. to 100° C., preferably from 0° C. to 80° C. The reaction time ranges from about 20 minutes to 5 days.

4) Thiocarbamoylation

In the above-mentioned carbamoylation, by conducting similar reaction employing thioisocyanate in place of isocyanate, a derivative into which monosubstituted thiocarbamoyl group is introduced can be synthesized.

5) Sulfonylation

This sulfonylation is carried out by allowing fumagillol to react with, for example, sulfonic anhydride, an activated sulfonic acid derivative such as sulfonyl halide (e.g. sulfonyl chloride, sulfonyl bromide, etc.) or an activated sulfamic acid derivative such as sulfamoyl halide (e.g. sulfamoyl chloride, sulfamoyl bromide, etc.

The said reactive derivatives of the sulfonic acid are employed in an amount usually ranging from about 1 mol. to 5 times as much mol. relative to 1 mol. of fumagillol.

This reaction is conducted usually in the presence of a base. As the base, use is made of those mentioned in the description of the alkylation, and the amount to be added ranges usually from about 1 mol. to 10 times as much mol. relative to 1 mol. of fumagillol.

This reaction is carried out usually in an organic solvent which does not exert undesirable influence on the reaction. As the organic solvent which does not exert undesirable influence on the reaction, use is made of those mentioned in the description of the alkylation.

While the reaction temperature varies with the amounts of sulfonic acid or the amount and kinds of sulfamic acid derivatives, bases and solvents, it ranges usually from −80° C. to 100° C., preferably from 0° C. to 80° C. The reaction time ranges from about 10 minutes to about 5 days.

6) Oxycarbonylation

Oxycarbonylation is also conducted by allowing a chloroformic acid ester (e.g. phenyl chloroformate, ethyl chloroformate, isobutyl chloroformate, benzyl chloroformate, 1-chloroethyl chloroformate, etc.) to react with fumagillol. The chloroformic acid ester is used usually in an amount of 1 mol. to 5 times as much mol. relative to 1 mol. of fumagillol.

This reaction is conducted usually in the presence of a base. As the base, use is made of those mentioned in the description of the alkylation, and the amount to be added ranges usually from 1 mol. to 10 times as much mol. relative to 1 mol. of fumagillol.

This reaction is conducted usually in an organic solvent which does not exert undesirable influence on the reaction. As the organic solvent which does not exert undesirable influence on the reaction, use is made of those mentioned in the description of the alkylation.

While the reaction temperature varies with the amounts, kinds, etc. of chloroformic acid ester, bases and solvents, it ranges from −20° C. to the reflux temperature of the reaction medium, preferably from 0° C. to 50° C. The reaction time ranges from about 10 minutes to about 5 days.

And, the compound (III) wherein G is mono- and disubstituted carbamoyl can be produced also by allowing the compound (III) wherein G is phenoxycarbonyl to react with ammonia, primary amines (e.g. methylamine, ethylamine, isopropylamine, etc.), or secondary amines (e.g. dimethylamine, ethylmethylamine, dimethylamine, pyrrolidine, piperidine, N-methylpiperazine, morpholine, etc.).

Ammonia, primary amines and secondary amines are employed usually in an amount of 1 mol. to 5 times as much mol. relative to 1 mol. of the starting compound.

This reaction is conducted usually in an organic solvent which does not exert undesirable influence on the reaction. As the organic solvent which does not exert undesirable influence, use is made of those mentioned in the description of the alkylation.

While the reaction temperature varies with amounts, kinds, etc. of ammonia, primary amines, secondary amines and solvents, it ranges from −20° C. to the reflux temperature of the reaction medium, preferably from 0° C. to 50° C. The reaction times ranges from about 20 minutes to about 5 days.

Reaction step 2: Production of the compound (IV) from fumagillol (II)

This reaction can be conducted by, for example in the acylation described in the acylation in the reaction step 1, using acid halide as the reactive derivative of carboxylic acid and, as the base, triethylamine or pyridine.

Reaction step 3: Production of the compound (V) from fumagillol (II)

This reaction can be conducted by allowing hydrogen halide to react with fumagillol.

Examples of the hydrogen halide include hydrogen bromide, hydrogen iodide, etc., and, in general, they are used as an aqueous solution of hydrobromic acid, hydroiodic acid, etc. The hydrogen halide is used in an amount of usually about 1 mol. to 10 times as much mol., preferably 1 to 5 times as much mol. relative to 1 mol. of fumagillol.

This reaction is conducted usually in a solvent which does not exert undesirable influence on the reaction. As the solvent which does not exert undesirable influence on the reaction, use is made of, for example, water, and alcohols, amides, halogenated hydrocarbons, ethers, esters, nitriles, nitro compounds, ketones, aromatic hydrocarbons, aliphatic hydrocarbons, etc. referred to in the reaction step 1. These can be used singly or as a suitable combination of two or more species of them.

While the reaction temperatures vary with the amounts, kinds, etc. of hydrogen halide and solvents, they are in the range from −80 to 100° C., preferably from 0° C. to room temperatures (room temperatures mean the range from about 20° to about 35° C., and the same applies hereinafter unless otherwise specified). The reaction time ranges from about 30 minutes to about 5 days.

The reaction with hydrogen iodide may be conducted in accordance with known methods such as [Cornforth, J. W., et al., J. Chem. Soc., 1959, 112].

Reaction step 4: Production of the compound (VI) from fumagillol (II)

This reaction is conducted by allowing secondary amines or thiols to react with fumagillol.

As the secondary amines or the thiols, use is made of $HNR^1R^2$, $HSR^1$ wherein $R^1$ and $R^2$ are of the same meaning as defined for them in the general formula (I), or metal salts thereof, and, as the metal salt, use is made of salts with, for instance, alkali metals (e.g. lithium, sodium, potassium, etc.), etc.

The secondary amines or the thiols are used in an amount of usually ranging from about 1 mol. to about 10 times as much mol., preferably 1 to 5 times as much mol., relative to 1 mol. of fumagillol.

This reaction may be conducted in the presence of a base. As the base, use is made of tertiary amine, alkali metal hydrogencarbonates, alkali metal carboantes, alkali metal hydrides, etc. mentioned in the reaction step 1, and the amount to be added ranges usually from about 1 mol. to 10 times as much mol. relative to 1 mol. of fumagillol.

This reaction is conducted in the absence of solvent or in a solvent which does not exert undesirable influence on the reaction. As the solvent which does not exert undesirable influence, use is made of, for example, solvents referred to in the reaction step 3.

The reaction temperature varies with the amounts, kinds etc. of secondary amines, thiols, bases and solvents, but it ranges from $-80°$ C. to $100°$ C., preferably from $0°$ C. to $50°$ C. The reaction time ranges from about 30 minutes to about 5 days

Reaction step 5: Production of the compound (IV) from the compound (III)

This reaction can be conducted by subjecting compound (III) to the reaction mentioned in the reaction step 3, and, in the reaction mentioned in the reaction step 3, hydrogen chloride or hydrochloric acid may be used as hydrogen halogenide.

Reaction step 6: Production from the compound (IV) from the compound (V)

This reaction can be conducted by subjecting compound (V) to the reaction mentioned in the reaction step 1.

Reaction step 7: Production of the compound (VI) from the compound (V)

This reaction can be conducted by subjecting compound (V) to the reaction mentioned in the reaction step 4.

Reaction step 8: Production of the compound (VII) from the compound (III)

This reaction can be conducted by subjecting compound (III) to the reaction mentioned in the reaction step 4.

Reaction step 9: Production of the compound (VII) from the compound (IV)

This reaction can be conducted by subjecting compound (IV) to the reaction mentioned in the reaction step 4.

Reaction step 10: Production of the compound (X) from the compound (IV)

This reaction can be conducted by allowing tertiary amines or sulfides to react with the compound (IV).

As the tertiary amines or the sulfides, use is made of $NR^1R^2R^3$ or $SR^1R^2$ wherein $R^1 \sim R^3$ are of the same meaning as defined for those in the general formula (I).

The tertiary amine or the sulfides are used in an amount of usually about 1 mol. to 10 times as much mol., preferably 1 to 5 times as much mol., relative to a mol. of the compound (IV).

This reaction can also be conducted in the presence of a base or metal salt. As the base, use is made of the afore-mentioned alkali metal hydrogencarbonates, alkali metal carbonates, etc., and, as the metal salt, use is made of mercury salts (e.g. mercury iodide, etc.) or silver salts (e.g. silver tetrafluoroborate, silver perchlorate, etc.), etc., and the amount to be added ranges usually from about 1 mol. to 5 times as much mol. relative to 1 mol. of the compound (IV).

This reaction is conducted in the absence of solvent or in an organic solvent which does not exert undesirable influence. As the organic solvent which does not exert undesirable influence, use is made of alcohols, amides, halogenated hydrocarbons, ethers, esters, nitriles, nitro compounds, ketones, aromatic hydrocarbons, aliphatic saturated hydrocarbons, etc. mentioned in the reaction step 1, and these solvents may be used singly or as a mixture of two or more of them in a suitable ratio.

The reaction temperature varies with the amount, kinds, etc. of tertiary amines, sulfides, bases, metal salts and solvents, but it ranges from $-80°$ C. to $100°$ C., preferably from $0°$ C. to $50°$ C. The reaction time ranges from about 30 minutes to about 15 days.

Reaction step 11: Production of the compound (VIII) from the compound (V)

This reaction can be conducted by subjecting compound (V) to the reaction described in the reaction step 10.

Reaction step 12: Production of the compound (VII) from the compound (VI)

This reaction can be conducted by subjecting compound (VI) to the reaction described in the reaction step 1.

Reaction step 13: Production of the compound (VIII) from the compound (VI)

This reaction is conducted by subjecting compound (VI) to N or S alkylation.

The said alkylation is conducted by allowing an alkylating agent represented by $R^3J$ wherein $R^3$ is of the same meaning as defined for $R_3$ in the general formula (I), and J stands for a leaving group such as halogen, methanesulfonyloxy group, p-toluenesulfonyloxy group, methoxysulfonyloxy group, trifluromethanesulfonyloxy group, dimethyloxonio.tetrafluoroborate group, diethyloxonio.tetrafluoroborate group, etc. to react with the compound (VI).

The alkylating agent is used usually in a range of from about 1 mol. to 100 times as much mol. relative to 1 mol. of the compound (VI).

This reaction may be conducted in the presence of a base or a metal salt. As the base, use is made of alkali metals hydrogencarbonates, alkali metal carbonates, etc. mentioned in the reaction step 1, and, as the metal salt, use is made of mercury salt (e.g. mercury iodide, etc.), and the amount of such base to be added ranges from about 0.1 mol. to 5 times as much mol. relative to 1 mol. of the starting alcohol.

This reaction is conducted in the absence of solvent or in an organic solvent which does not exert undesirable influence on the reaction. As the organic solvent which does not exert undesirable influence on the reaction, use is made of amides, halogenated hydrocarbons, ethers, esters, nitriles, nitro compounds, ketones, aromatic hydrocarbons, aliphatic hydrocarbons, etc., and these can be used singly or as a mixture of two or more of them in a suitable ratio.

The reaction temperature varies with the amounts, kinds, etc. of the alkylating agents, bases, metal salts and solvents, but it ranges from −80° C. to 100° C., preferably from 0° C. to 50° C. The reaction time ranges from about 20 minutes to about 5 days.

Reaction step 14: Production of the compound (IX) from the compound (VI)

This reaction is conducted by subjecting NR R: group or $SR^3$ group shown by X in the compound (VI) to oxidation.

As he oxidizing agent to be employed for the oxidation, use is made of aqueous hydrogen peroxide, periodic acid (e.g. ortho periodic acid, meta periodic acid, etc.) or salts thereof, organic peracids (e.g. performic acid, peracetic acid, perbenzoic acid methachloroperbenzoic acid, etc.) or salts thereof.

This reaction is conducted usually in a solvent which does not exert undesirable influence on the reaction. As the solvent which does not exert undesirable influence on the reaction, use is made of water, and halogenated hydrocarbons, ethers, aromatic hydrocarbons or aliphatic saturated hydrocarbons mentioned in the reaction step 1. These solvents may be used singly or a mixture of two or more of them in a suitable ratio.

The reaction temperature varies with the amounts, kinds etc. of the oxidizing agents and solvents, but it ranges from −80° C. to 100° C., preferably from 0° C. to 50° C. The reaction time ranges from about 20 minutes to 5 days.

Reaction step 15: Production of the compound (X) from the compound (VII)

This reaction can be conducted by subjecting compound (VII) to the reaction described in the reaction step 13.

Reaction step 16: Production of the compound (X) from the compound (VIII)

This reaction can be conducted by subjecting compound (VIII) to the reaction described in the reaction step 1.

Reaction step 17: Production of the compound (XI) from the compound (VIII)

This reaction can be conducted by subjecting compound (VIII) wherein M stands for $S^{\oplus}R^1R^2.X^{\ominus}$ to the reaction described in the reaction step 14.

Reaction step 18: Production of the compound (XI) from the Compound (IX)

This reaction can be conducted by subjecting compound (IX) wherein L is $S(O)R^1$ to the reaction described in the reaction step 11.

Reaction step 19: Production of the compound (XII) from the compound (IX)

This reaction can be conducted by subjecting compound (IX) to the reaction described in the reaction step 1.

Reaction step 20: Production of the compound (XIII) from the compound (X)

This reaction can be conducted by subjecting compound (X) wherein M is $S^{\oplus}R^1R^2.X^{\ominus}$ to the reaction described in the reaction step 14.

Reaction step 21: Production of the compound (XIII) from the compound (XI)

This reaction can be conducted by subjecting compound (XI) to the reaction described in the reaction step 1.

Reaction step 22: Production of the compound (XIII) from the compound (XII)

This reaction can be conducted by subjecting compound (XII) wherein L is $S(O)R^1$ to the reaction described in the reaction step 11.

Reaction step 23: Production of the compound (XII) from the compound (VII)

This reaction can be conducted by subjecting compound (VII) to the reaction described in the reaction step 14.

Reaction step 24: Production of the compound (XIV) from fumagillol (II)

This reaction is conducted by subjecting fumagillol to oxidation using chromic anhydride in Tarbell et al. [Tarbell, D. S.,, (J. Am. Chem. Soc.), 77, 5610 (1955)], or to oxidation using pyridinium dichromate in accordance with the method of Goto et al. (JPA Sho 62-476).

In accordance with known method such as Jones oxidation [Jones. E. R. H., (J. Chem. Soc.), 1946, 39], Collins oxidation [Collins, J. C., Tetrahedron Lett., 1968, 3363], PCC oxidation [Corey, E. J., et al., Tetrahedron Lett., 1975, 2647] or oxidation using the combination of dimethylsulfoxide and an activating agent may be conducted. As the activating agent for dimethylsulfoxide, use can be made of dicyclohexylcarbodiimide [Moffat, J. G., et al. J. Am. Chem. Soc., 85, 3027 (1963)], acetic anhydride [Albright, J. D., et al., J. Am. Chem. Soc., 87, 4214 (1965)], phosphorus pentoxide [Onodera et al. J. Am. Chem. Soc.), 87, 4214 (1965)], sulfur trioxide-pyridine complex [Parikh, J. R., et al., J. Am. Chem. Soc., 89, 5505 (1967)], oxalylchloride [Swern, D., et al., J. Org. Chem., 43, 2480 (1978)], etc.

Reaction step 25: Production of the compound (XVII) from the compound (XIV)

This reaction is conducted by subjecting compound (XIV), in accordance with known methods such as [Borch, R. F. et al. J. Am. Chem. Soc., 93, 2897 (1971)], to reductive amination.

Reaction step 26: Production of the compound (XV) from fumagillol (II)

This reaction can be carried out, in accordance with the scheme 1, by subjecting fumagillol to any one of the reactions described in the reaction steps 3, 4, 11, 13, 14, 17 and 18, or to a suitable combination of them.

Reaction step 27: Production of the compound (XVI) from the compound (XIV)

This reaction can be carried out, in a manner similar to the scheme 1, by subjecting compound (XIV) to any one the reactions described in the reaction steps 3, 4, 11, 13, 14, 17 and 18, or to a suitable combination of them.

Reaction step 28: Production of the compound (XVI] from the compound (XV)

This reaction can be carried out by subjecting compound (XV) to the reaction described in the reaction step 24. And, transformation of the portion A may be carried out simultaneously by a suitable combination of the reaction described in the reaction step 24 with any one of the reactions described in the reaction steps 9, 10, 13, 14, 17 and 18.

Reaction step 29: Production of the compound (XIX) from the compound (XVI)

This reaction can be conducted by subjecting compound (XVI) to the reaction described in the reaction step 25. Transformation of the portion A may be carried out simultaneously by a suitable combination of the reaction described in the reaction step 25 with any one of the reactions described in the reaction steps 9, 10, 13, 14, 17 and 18.

Reaction step 30: Production of the compound (XVIII) from the compound (XVII)

This reaction can be conducted, in a manner similar to the scheme 1, by subjecting the compound (XVII) to the reaction described in the reaction step 1.

In the case of conducting alkylation of the NHR$^4$ group of compound (XVII), other than the method described in the reaction step 1, a method known as a reductive alkylation [Emoerson, W. S., Org. React., 4, 174 (1948); or Lane, C. F., Synthesis, 135 (1975)] may be employed.

Reaction step 31: Production of the compound (XIX) from the compound (XVII)

This reaction can be conducted by subjecting compound (XVII) to the reaction described in the reaction step 27.

Reaction step 32: Production of the compound (XX) from the compound (XIX)

This reaction can be conducted by subjecting compound (XIX) to the reaction described in the reaction step 30. Transformation of the portion A may be carried out simultaneously by a suitable combination of the reaction described in the reaction step 30 with any one of the reactions described in the reaction steps 9, 10, 13, 14, 17 and 18.

Reaction step 33: Production of the compound (XX) from the compound (XVIII)

This reaction can be carried out, in a manner similar to the scheme 1, by subjecting compound (XVIII) to any one of the reactions described in the reaction steps 5, 8, 9, 10, 15, 20, 22 and 23, or to a suitable combination of them.

Reaction step 34: Production of the compound (XXI) from fumagillol

This reaction is conducted by subjecting a 6-O-acyl −6-epifumagillol derivative to hydrolysis by known methods such as [Bose, A. K., Tetrahedron Lett., 1973, 1619], the derivative being obtained by subjecting fumagillol to the Mitsunobu reaction using diethyl azodicarboxylate and carboxylic acid such as triphenyl phosphine and formic acid or benzoic acid [Mitsunobu, O., Synthesis, 1 (1981)].

Reaction step 35: Production of the compound (XXIII) from the compound (XV)

This reaction can be conducted by subjecting compound (XV) to the reaction described in the reaction step 34. Transformation of the portion A can be conducted simultaneously by suitable combination of the reaction described in the reaction step 34 with any one of the reactions described in the reactions steps 9, 10, 13, 14, 17 and 18.

Reaction step 36: Synthesis of the compound (XXII) from the compound (XXI)

This reaction can be conducted by subjecting compound (XXI) to the reaction described in the reaction step 1.

Reaction step 37: Synthesis of the compound (XXV) from the compound (XXIII)

This reaction can be conducted by subjecting compound (XXIII) to a reaction similar to that described in the reaction step 1. Transformation of the portion A may be carried out simultaneously by a suitable combination of the reaction described in the reaction step 1 with any one of the reactions described in the reaction steps 9, 10, 13, 14, 17 and 18.

Reaction step 38: Synthesis of the compound (XXIII) from the compound (XXI)

This reaction can be conducted by subjecting compound (XXI) to the reaction described in the reaction step 27.

Reaction step 39: Production of the compound (XXIV) from the compound (XXII)

This reaction can be conducted by subjecting compound (XXII) to the reaction described in the reaction step 33.

Reaction step 40: Production of the compound (XXV) from fumagillol (II)

This reaction is conducted by subjecting an imide compound to hydrolysis by means of known methods such as [Mitsunobu, O., J. Am. Chem. Soc., 94, 679 (1972)], the imide compound being obtained by subjecting fumagillol to Mitsunobu reaction using diethyl azodicarboxylate, triphenyl phosphine and imide such as phthalimide or succinimide [Mitsunobu, O., Synthesis, 1 (1981)].

Reaction step 41: Production of the compound (XXIX) from the compound (XV)

This reaction can be conducted by subjecting compound (XV) to the reaction described in the reaction step 40. transformation of the portion A may be simultaneously carried out by suitable combination of the reaction described in the reaction step 40 with any one of the reactions described in the reaction steps 9, 10, 13, 14, 17 and 18.

Reaction step 42: Production of the compound (XXIX) from the compound (XXV)

This reaction can be conducted by subjecting compound (XXV) to the reaction described in the reaction step 27.

Reaction step 43: Production of the compound (XXVII) from the compound (XXV)

This reaction can be conducted by subjecting compound (XXV) to N-alkylation by means of known methods such as ["Comprehensive Organic Chemistry" Vol. 2, pp. 4 to 11, compiled by Sutherland, I.O., Pergamon Press (1979)].

Reaction step 44: Production of the compound (XXXI) from the compound (XXIX)

This reaction can be conducted by subjecting compound (XXIX) to the reaction described in the reaction step 43. Transformation of the portion A may be carried out by a suitable combination of the reacitn described in the reaction step 43 with any one of the reactions described in the reaction steps 9, 10, 13, 14, 17 and 13.

Reaction step 45: Production of the compound (XXXI) from the compound (XXVII)

This reaction can be conducted by subjecting compound (XXVII) to the reaction described in the reaction step 27.

Reaction step 46: Production of the compound (XXVI) from the compound (XXV)

This reaction can be conducted by subjecting compound (XXV) to the reaction described in the reaction step 30.

Reaction step 47: Production of the compound (XXX) from the compound (XXIX)

This reaction can be conducted by subjecting compound (XXIX) to the reaction described in the reaction step 30.

Reaction step 48: Production of the compound (XXX) from the compound (XXVI)

This reaction can be conducted by subjecting compound (XXVI) to the reaction described in the reaction step 33.

Reaction step 49: Production of the compound (XXVIII) from the compound (XXVII)

This reaction can be conducted by subjecting compound (XXVII) to the reaction described in the reaction step 30.

Reaction step 50: Production of the compound (XXXII) from the compound (XXXI)

This reaction can be conducted by subjecting compound (XXXI) to the reaction described in the reaction step 30. Transformation of the portion A may be carried out simultaneously by a suitable combination of the reaction described in the reaction step 30 with any one of the reactions described in the reaction steps 9, 10, 13, 14, 17 and 18.

Reaction step 51: Production of the compound (XXXII) from the compound (XXVIII)

This reaction can be conducted by subjecting compound (XXVII) to the reaction described in the reaction step 33.

When substituents such as amino group, lower alkyl amino group, hydroxyl group and carboxyl group are present on starting compounds to be employed in the afore-described methods and on acylating agents, carbamoylating agents, alkylating agents and sylfonylating agents to be employed in these methods, the reaction can be allowed to proceed advantageously by having these substituents protected previously.

For the protection and deprotection of these substituents, known methods such as [Greene, T. W., "Protective Group in Organic Synthesis", John Wiley & Sons, New York (1981)] can be used.

Thus-produced compound (I) of the present invention can be isolated by, for example, known separating and purifying means (e.g. chromatography, crystallization). And, in the case of the compound (I) containing counter anion shown by $X^\ominus$, exchange of the counter anion can be conducted by processing with, for example, ion-exchange resin or silver salt (e.g. silver oxide, silver acetate, silver perchlorate, etc.).

The compounds of this invention show an action of inhibiting angiogenesis and an anti-tumor activity, and are useful as therapeutic and prophylactic agents of various inflammatory diseases (rheumatic diseases, psoriasis), diabetic retinopathy or tumors, and their toxicity is relatively low. And, they can be safely administered orally or non-orally as they are or as a pharmaceutical composition prepared by mixing with known pharmaceutically acceptable carriers, excipients, etc. [e.g. tablets, capsules (including soft capsules, microcapsules), liquids, injections, suppositories]. The dosage varies with, among others, subjects, routes and symptoms, but, usually, it ranges, in an adult, from about 0.1 mg/kg to about 40 mg/kg body weight, preferably from about 0.5 mg/kg to about 20 mg/kg body weight per day.

Pharmacological effects of the compounds of this invention are described as follows.

EXPERIMENTAL EXAMPLE 1

Angiogenesis inhibitory action by the rat cornea micropocket method

Method of Evaluation:

Essentially the same method of Gimbrone et al. [J. National Cancer Institute 52:413–419 (1974)] was follows.

Specifically, adult male Sprague-Dawley rats (11 to 16 week old) were anesthetized with nembtal and locally anesthetized by instillation of xylocaine eyedrops onto the eyeball. The cornea was incised to a length of about 2 mm at about 2 mm inside from the corneal circumference by means of an injection needle, and a basic fibroblast growth factor (bFGF, bovine brain-derived, purified product, R & D Inc.) and a sustained release pellet containing the test sample were inserted side by side into the incision so that the bFGF pellet was located on the central side in the cornea. In the control group, the bFGF pellet and a sample-free pellet were inserted into the cornea. After 10 days, the cornea was observed under a stereoscopic microscope. The results are shown in Table 1.

The sustained release pellets were prepared in the following manner. An ethylene-vinyl acetate copolymer (Takeda Chemical Industries, Ltd.) was dissolved in dichloromethane to a concentration of 8%. A 3 $\mu$l portion of the solution was air-dried on a glass dish, an aqueous solution of bFGF (250 ng) was then placed thereon and air-dried and, finally 3 $\mu$l of the above-mentioned ethylene-vinyl acetate copolymer solution was placed further thereon and air-dried to give a sandwich sheet. This sandwich sheet was made round into a bFGF pellet. The test sample pellets were prepared by dissolving each sample in ethanol to a concentration of 20 $\mu$g/2 $\mu$l, mixing the solution with 6 $\mu$l of an ethylene-vinyl acetate copolymer solution, air-drying the mixed solution on a glass dish and making the thus-obtained sheet round.

TABLE 1

| | Angiogenesis Inhibitory Activity | |
|---|---|---|
| Compound (Example No.) | Inhibitory Rate | Judgment |
| 1c | 5/5 | + |
| 3 | 4/7 | ± |
| 4 | 3/5 | ± |
| 10 | 4/7 | ± |
| 48 | 4/7 | ± |
| 70 | 5/6 | + |
| 91 | 6/6 | + |

In the above Table 1, the number of rats subjected to the test was shown by denominator, and the number of rats whose angiotensin due to bFGF was retarded or weakened by administration of the test sample was shown by numerator. In the judgment, +means an inhibition rate of 70% or more, and ±means that of less than 70% but exceeding 40%.

EXPERIMENTAL EXAMPLE 2

C57BL/6 mice (a group consisting of 6 mice) were inoculated subcutaneously at the dorsolateral area with $2 \times 10^6$ M5076 cells, and then a test compound dissolved in a 5% gum arabic physiological saline solution was subcutaneously administered 10 times in total, i.e. 1st, 2nd, 4th, 5th, 6th, 7th, 8th, 9th, 11th and 12th day after the inoculation. After 13 days, the major axis (a) and the minor axis (b) of the tumor tissue were measured to determine the tumor size by the calculation formula of $a \times b^2 \times \frac{1}{2}$. The ratio of the tumor size thus calculated to the tumor size of animals in the control group was shown by T/C (%). The results are shown in Table 2.

TABLE 2

| Compound (Example No.) | Dose (mg/kg) | T/C (%) |
|---|---|---|
| 1c | 30 | 20 |
| 2 | 30 | 20 |
| 3 | 30 | 36 |
| 13 | 30 | 36 |
| 16 | 30 | 20 |
| 17 | 30 | 21 |
| 60 | 20 | 21 |
| 61 | 20 | 27 |
| 62 | 20 | 29 |
| 64 | 20 | 24 |
| 65A | 20 | 9 |
| 65B | 20 | 37 |
| 76 | 20 | 29 |
| 82 | 20 | 9 |
| 100 | 20 | 22 |
| 104 | 20 | 16 |

EXAMPLES

By the following Reference Examples and Examples, the present invention will be described in more detail, but the present invention is by no means limited to these examples.

The elution in the column chromatography in the following Reference Examples and Examples (bracketed terms are solvents for elution) is conducted under observation by means of thin layer chromatography (TLC).

In the TLC observation, as the TLC plate, Kieselgel 60F$_{250}$ (70 to 230 mesh, Merck) was employed, as the developing solvent, the one employed for elution in the column chromatography, and, as the method of detection, a UV detector, a color-development method with phosphorus molybdate, etc. were employed. As the silica gel for the column, Kieselgel 60 (70 to 230 mesh, Merck) was employed. NMR spectrum shows proton NMR($^1$H-NMR), and, as interior or exterior standard, tetramethylsilane was employed, and the measurement was carried out by using Gemini 200 (VARIAN) showing the δ value in terms of ppm.

Abbreviations used in Reference Examples and Examples have the following significances, respectively.

s:singlet, br:broad, d:doublet, dd:double doublet, ddd:doublet doublet doublet, t:triplet, q:quartet, m:multiplet, ABq:AB quartet, J:coupling constant, Hz:Hertz, %:weight %.

And, the term "room temperatures" appearing in the following reference examples and working examples means temperatures ranging from about 15° to 25° C. Melting points and temperatures are all shown by centigrade.

In the description of compound names in the following Reference Examples and Examples, portion of the absolute steric configuration was omitted as it was in agreement with that of fumagillol. Referring to the relative steric configuration, only the portion different from that of fumagillol based on the structural formula shown for Compound (I) was described.

REFERENCE EXAMPLE 1

2-(1,2-epoxy-1,5-dimethyl-4-hexenyl)-3-methoxy-1-chloromethyl-1,4-cyclohexanediol To a solution of fumagillol (200 mg) in ethanol (2 ml) was added 0.5N hydrochloric acid (1 ml), and the mixture was stirred at room temperatures for one hour. To the reaction mixture was added a saturated aqueous solution of sodium hydrogencarbonate to neutralize, which was concentrated under reduced pressure. The concentrate was purified by means of a silica gel column chromatography (carrier 10 g, developing solvent:hexane-ethylacetate=3:1) to give 2-(1,2-epoxy-1,5-dimethyl-4-hexenyl)-3-methoxy-1-(chloromethyl)-1,4-cyclohexanediol (200 mg: yield 90%).

NMR spectrum (δ value;CDCl$_3$) : 1.33(1H,m), 1.49(3H,s), 1.67(3H,s), 1.75(3H,s), 1.5 to 2.6(7H,m), 2.99(1H,t,6Hz), 3.2 to 3.4(1H,m), 3.35(3H,s), 3.50(1H,d,11Hz), 3.90(1H,br s), 4.23(1H,m), 5.19(1H,m).

REFERENCE EXAMPLE 2

O-chloroacetylcarbamoyl fumagillol

To a solution of fumagillol (314 mg) in dichloromethane (5 ml) was added dropwise, under cooling with ice, chloroacetylisocyanate (160 mg), to which was then added dimethylaminopyridine (130 mg), followed by stirring at 0° C. for two hours. To the reaction mixture was added water, which was subjected to extraction with dichloromethane. The organic layer was washed with a saturated aqueous saline solution, then dried over anhydrous magnesium sulfate. The solvent was distilled off under reduced pressure, and the residue was purified by means of a silica gel column chromatography (carrier 20 g, developing solvent: ethylacetate-hexane=1:2)' to afford O-chloroacetylcarbamoyl fumagillol (318 mg: yield 71%) as colorless powder.

NMR spectrum (δ value; CDCl$_3$) : 1.10(1H,m), 1.21(3H,s), 1.66(3H,s), 1.75(3H,s), 1.93(1H,d,11Hz), 1.8 to 2.5(5H,m), 2.57(1H,d,4Hz), 2.58(1H,m), 2.99(1H,d,4Hz), 3.47(3H,s), 3.58(1H,dd,11Hz,3Hz), 4.44(2H,s), 5.20(1H,m), 5.61(1H,m), 8.33(1H,br s).

REFERENCE EXAMPLE 3

O-(p-toluenesulfonyl)fumagillol

To a solution of fumagillol (3.00 g) and dimethylamino pyridine (3.24 g) in anhydrous dichloromethane (30 ml) was added p-toluenesulfonyl chloride (3.04 g), and the mixture was stirred at room temperatures overnight. The reaction mixture was diluted with dichloromethane, washed with a saturated aqueous saline solution, followed by drying over anhydrous magnesium sulfate. The solvent was distilled off under reduced pressure, then the residue was purified by means of a silica gel column chromatography (carrier 150 g, developing solvent:ethyl acetatehexane = 1:2). The resulting crude crystals were recrystallization from diisopropylether to afford O-(p-toluenesulfonyl)fumagillol as colorless crystals (2.88 g:yield 62%). m.p.: 123° to 124° C.

NMR spectrum ($\delta$ value; $CDCl_3$):1.14(1H,m), 1.16(3H,s), 1.67(3H,s), 1.70(3H,s), 1.84(1H,m), 1.95(1H,d,11Hz), 2.04 to 2.47(4H,m), 2.44(3H,s), 2.55(1H,d,4Hz), 2.56(1H,t,6Hz), 2.94(1H,d,4Hz), 3.02(3H,s), 3.50(1H,dd,10Hz),2Hz), 5.07(1H,m), 5.19(1H,m), 7.33(2H,d,8Hz), 7.87(2H,d,8Hz).

REFERENCE EXAMPLE 4

O-phenoxycarbonyl fumagillol

Fumagillol (133 mg) and dimethylaminopyridine (115 mg) were dissolved in dichloromethane (3 ml). To the solution was added phenyl chloroformate (111 mg), and the mixture was stirred for 30 minutes at room temperatures. To the resultant was added water, which was diluted with dichloromethane (30 ml), followed by washing with water and a saturated aqueous solution of sodium chloride. The solvent was distilled off under reduced pressure. The residue was purified by means of a silica gel column chromatography (carrier 10 g, developing solvent:n-hexane-ethyl acetate = 5:1) to afford O-phenoxycarbonyl fumagillol (174 mg:yield 92%) as a colorless oily product.

NMR spectrum ($\delta$ value; $CDCl_3$):1.10(1H,m), 1.22(3H,s), 1.66(3H,s), 1.75(3H,s), 1.8 to 2.45(6H,m), 2.56(1H,d,4Hz), 2.59(1H,t,6Hz), 2.99(1H,d,4Hz), 3.50(3H,s), 3.69(1H,dd,11Hz,3Hz), 5.18(1H,m), 5.58(1H,br s), 7.15 to 7.45(5H,m).

REFERENCE EXAMPLE 5

6-O-formyl-6-epifumagillol

Fumagillol (4.0 g), triphenylphosphine (11.2 g) and formic acid (1.1 ml) were dissolved in tetrahydrofuran (100 ml). To the solution was added dropwise a solution of diethylazocarboxylate (7.4 g) in tetrahydrofuran (20 ml). The mixture was stirred overnight, which was then diluted with ethyl acetate (300 ml), followed by washing with a saturated aqueous solution of sodium chloride, then with a saturated aqueous solution of sodium hydrogencarbonate and further with a saturated aqueous solution of sodium chloride. The resultant was dried over anhydrous magnesium sulfate, then the solvent was distilled off under reduced pressure. The residue was purified by means of a silica gel chromatography (carrier 200 g, developing solvent:ethyl acetate-hexane = 1:3) to afford 6-O-formyl-6-epifumagillol (2.6 g: yield 59%).

NMR spectrum ($\delta$ value; $CDCl_3$): 1.21(1H,m), 1.27(3H,s), 1.61(1H,d,11Hz), 1.66(3H,s), 1.75(3H,s), 1.70 to 2.25(4H,m), 2.38(1H,m), 2.56(1H,m), 2.59(1H,d,4Hz), 2.98(1H,d,4Hz), 3.56(3H,s), 3.83(1H,dd,9Hz,11Hz), 5.00(1H,m), 5.20(1H,m), 8.17(1H,s).

REFERENCE EXAMPLE 6

6-Epifumagillol

6-O-formyl-6-epifumagillol (2.5 g) was dissolved in methanol (20 ml), to which was added conc. ammoniacal water (5 ml), and the mixture was stirred for 15 minutes. The solvent was distilled off under reduced pressure, then the residue was dissolved in ethyl acetate (100 ml), which was washed with a saturated aqueous solution of sodium chloride. The resultant was dried over anhydrous magnesium sulfate, then the solvent was distilled off under reduced pressure. The residue was purified by means of a silica gel chromatography (carrier 100 g, developing solvent:ethyl acetate-hexane = 2:1) to afford 6-epifumagillol (1.8 g: yield 79%).

NMR spectrum ($\delta$ value; $CDCl_3$): 1.22(1H,m), 1.30(3H,s), 1.54(1H,d,11Hz), 1.66(3H,s), 1.75(3H,s), 1.70 to 2.25(4H,m), 2.38(1H,m), 2.54(1H,d,4Hz), 2.57(1H,t,7Hz), 2.91(1H,d,4Hz), 3.54 to 3.80(2H,m), 3.61(3H,s), 5.20(1H,m).

REFERENCE EXAMPLE 7

6-O-phenoxycarbonyl-6-epifumagillol

6-Epifumagillol (0.53 g) and dimethylaminopyridine (0.46 g) were dissolved in dichloromethane (8 ml), to which was added phenyl chloroformate (0.45 g), followed by stirring at room temperatures for 30 minutes. To the resultant was added water, which was then diluted with dichloromethane (40 ml). The resultant was washed with water and a saturated aqueous solution of sodium chloride, which was dried over magnesium sulfate. The solvent was distilled off under reduced pressure, and the residue was purified by means of a silica gel chromatography (carrier 25 g, developing solvent:ethyl acetate - hexane = 1:5), followed by crystallization from ethanol to give 6-O-phenoxycarbonyl-6-epifumagillol (0.55 g; yield 82%). m.p. 118° to 119° C.

NMR spectrum ($\delta$ value; $CDCl_3$):1.22(1H,m), 1.28(3H,s), 1.63(1H,d,11Hz), 1.66(3H,s), 1.75(3H,s), 1.6 to 2.5(5H,m), 2.57(1H,t,7Hz), 2.59(1H,d,4Hz), 2.98(1H,d,4Hz), 3.65(3H,s), 3.84(1H,dd,9Hz,11Hz), 4.88(1H,m), 5.20(1H,m), 7.1 to 7.5(5H,m).

REFERENCE EXAMPLE 8

6-O-morpholinocarbonyl-6-epifumagillol

6-O-phenoxycarbonyl-6-epifumagillol (0.17 g) was dissolved in dichloromethane (4 ml), to which was added morpholine (1 ml), and the mixture was stirred at room temperatures for one day. The reaction mixture was diluted with ethyl acetate (30 ml), which was washed with a saturated aqueous solution of ammonium chloride and a saturated aqueous solution of sodium chloride. The resultant was dried over magnesium sulfate, then the solvent was distilled off under reduced pressure. The residue was purified by means of a silica gel chromatography (carrier 20 g, developing solvent-,:ethyl acetate - hexane = 1:2) to afford 6-O-morpholinocarbonyl-6-epifumagillol (0.13 g:yield 74%). m.p.:139° to 140° C.

NMR spectrum ($\delta$ value; $CDCl_3$): 1.20(1H,m), 1.26(3H,s), 1.66(3H,s), 1.75(3H,s), 1.6 to 2.6(7H,m), 2.58(1H,d,4Hz), 2.97(1H,d,4Hz), 3.50(4H,m), 3.54(3H,s), 3.67(4H,m), 3.80(1H,dd,9Hz,11Hz), 4.87(1H,m), 5.21(1H,m).

REFERENCE EXAMPLE 9

6β-Phthalimido-6-desoxyfumagillol

Fumagillol (1.0 g), triphenylphosphine (1.22 g) and phthalimide (0.57 mg) were dissolved in tetrahydrofuran (THF, 30 ml), to which was added dropwise a solution of diethyl azodicarboxylate (0.88 g) in THF (5 ml). The mixture was stirred for 30 minutes, which was then diluted with ethyl acetate (100 ml). The resultant was washed with a saturated aqueous solution of sodium chloride, then with a saturated aqueous solution of sodium carbonate and, further, with a saturated aqueous solution of sodium chloride once again, followed by drying over anhydrous magnesium sulfate. The solvent was distilled off under reduced pressure, and the residue was purified by means of a silica gel column chromatography (carrier 50 g, developing solvent:ethyl acetate-hexane=1:3) to afford 6β-phthalimido-6-desoxyfumagillol (0.99 g: yield 68%).

NMR spectrum (δ value; CDCl₃) 1.27(1H,m), 1.32(3H,s), 1.65 to 2.70(7H,m), 1.67(3H,s), 1.73(3H,m), 2.58(1H,d,4Hz), 2.99(1H,d,4Hz), 3.33(3H,s), 4.36(1H,m), 4.71(1H,t,10Hz), 5.23(1H,m), 7.73(2H,m), 7.88(2H,m).

REFERENCE EXAMPLE 10

6β-Amino-6-6-desoxyfumagillol

6β-Phthalimido-6-desoxyfumagillol (2.0 g) was dissolved in methanol (40 ml), to which was added hydrazine-hydrate (1.4 g), and the mixture was stirred for 20 minutes. The solvent was distilled off under reduced pressure, and the residue was subjected to azeotropic distillation with ethanol to remove the excess amount of hydrazine-hydrate. The residue was dissolved in water (20 ml), to which was added acetic acid (1.5 ml), and the mixture was stirred overnight. Resulting precipitates were filtered off. To the filtrate was added conc. ammoniacal water (4 ml), then the product was extracted with chloroform. The extract solution was dried over anhydrous magnesium sulfate, then the solvent was distilled off under reduced pressure. The residue was purified by means of a silica gel column chromatography (carrier 100 g, developing solvent: chloroform-methanol-conc. ammoniacal water=30:1:0.03) to afford 6β-amino-6-desoxyfumagillol (0.9 g: yield 40%).

NMR spectrum (δ value; CDCl₃): 1.17(1H,m), 1.29(3H,s), 1.50 to 1.95(4H,m), 1.66(3H,s), 1.79(3H,m), 2.27(1H,m), 2.37(1H,m), 2.52(1H,d,4Hz), 2.55(1H,t,6Hz), 2.90(1H,m), 2.92(1H,d,4Hz), 3.47(1H,dd,9Hz,11Hz), 3.56(3H,s), 5.22(1H,m).

REFERENCE EXAMPLE 11

6β-Hexylamino-6-desoxyfumagillol

6β-Amino-6-desoxyfumagillol (3.0 g), hexanal (1.4 ml) and acetic acid (1.5 ml) were dissolved in methanol (60 ml). To the solution was added sodium cyanoborohydride (0.67 g). The mixture was stirred for one hour, and the resulting reaction mixture was diluted with ethyl acetate (100 ml), followed by washing with a saturated aqueous solution of sodium hydrogencarbonate and with a saturated aqueous solution of sodium chloride. The resultant was dried over anhydrous magnesium sulfate, followed by distilling off the solvent under reduced pressure. The residue was purified by means of a silica gel column chromatography (carrier 150 g, developing solvent: chloroformmethanol-conc. ammoniacal water=30:1:0.03) to afford 6β-hexylamino-6-desoxyfumagillol (2.35 g: yield 60%).

NMR spectrum (δ value; CDCl₃): 0.89(3H,m), 1.10 to 2.35(12H,m), 1.66(3H,s), 1.74(3H,m), 2.51(1H,d,4Hz), 2.92(1H,d,4Hz), 3.50(3H,s), 3.69(1H,dd,9Hz,11Hz), 5.22(1H,m).

REFERENCE EXAMPLE 12

2-(1,2-epoxy-1,5-dimethyl-4-hexenyl)-3-methoxy-1-methylthiomethyl-4-oxo-1-cyclohexanol 6-Oxo-6-desoxyfumagillol (870 mg) was dissolved in DMF (2 ml), to which was added thiomethoxide (652 mg). The mixture was stirred for 30 minutes, followed by addition of water thereto to suspend the reaction. The product was extracted with isopropylether. The extract solution was washed with a saturated aqueous solution of sodium hydrogencarbonate and a saturated aqueous saline solution, which was then dried over anhydrous magnesium sulfate. The solvent was distilled off under reduced pressure. The residue was purified by means of a silica gel column chromatography (carrier 50 g, developing solvent: ethyl acetate-hexane=1 2) to afford 2-(1,2-epoxy-1,5-dimethyl-4-hexenyl)-3-methoxy-4-oxo-1-methylthiomethyl-1-cyclohexanol (693 mg: yield 70%).

NMR spectrum (δ value; CDCl₃): 1.46(3H,s), 1.67(3H,s), 1.75(3H,s), 1.88(1H,m), 2.05 to 2.60(4H,m), 2.20(3H,s), 2.30(1H,d,12Hz), 2.80(1H,m), 2.91(1H,d,13Hz), 2.99(1H,d,13Hz), 3.30(1H,t,6Hz), 3.41(3H,s), 3.88(1H,d,12Hz), 5.20(1H,m).

EXAMPLE 1a 2-(1,2-Epoxy-1,5-dimethyl-4-hexenyl)-3-methoxy-1-bromomethyl-1,4-cyclohexanediol To a solution of fumagillol (230 mg) in ethanol (2 ml) was added a 5% aqueous solution of hydrobromic acid (1 ml), and the mixture was stirred for one hour at room temperatures. The reaction mixture was neutralized with a saturated aqueous solution of sodium hydrogencarbonate, followed by concentration under reduced pressure. The concentrate was purified by means of a silica gel column chromatography (carrier 10 g, developing solvent: hexane-ethyl acetate=7:3) to afford 2-(1,2-epoxy-1,5-dimethyl-4-hexenyl)-3-methoxy1-bromomethyl-1,4-cyclohexanediol (242 mg: yield 80%) as a colorless oily product.

NMR spectrum (δ value; CDCl₃): 1.40(1H,m), 1.50(3H,s), 1.67(3H,s), 1.74(3H,s), 1.5 to 2.6(7H,m), 3.00(1H,t,6Hz), 3.2 to 3.4(1H,m), 3.35(3H,s), 3.49(1H,d,10Hz), 3.70(1H,d,10Hz), 3.90(1H,br s), 4.22(1H,m), 5.19(1H,m).

EXAMPLE 1b 2-(1,2-Epoxy-1,5-dimethyl-4-hexenyl)-3-methoxy-1-iodomethyl-1,4-cyclohexanediol Sodium iodide (398 mg) and sodium acetate (36.3 mg) were dissolved in a mixture of acetic acid (0.5 ml) and propionic acid (1 ml). To the solution was added, under ice-cooling, fumagillol (500 mg). The mixture was stirred for 20 minutes, which was then poured into a concentrated ammoniacal water (10 ml) to suspend the reaction. The product was extracted with ethyl acetate. The extract solution was washed with a saturated aqueous solution of sodium hydrogen carbonate and a saturated aqueous saline solution, followed by drying over anhydrous magnesium sulfate. The solvent was distilled off under reduced pressure, and the residue was purified by means of a silica gel column chromatography (carrier 20 g, developing solvent: ethyl acetate-hexane=1:2), followed by crystallization from isopropylether to afford 2-(1,2-epoxy-1,5-dimethyl-4-hexenyl)-3-methoxy-1-iodomethyl-1,4-cyclohexanol mg: yield 92%) as colorless crystals, m.p. 86° to 88° C.

NMR spectrum (δ value; CDCl₃) 1.48(1H,m), 1.51(3H,s), 1.67(3H,s), 1.75(3H,s), 1.70 to 2.55(6H,m), 3.01(1H,t,7Hz), 3.26(1H,m), 3.35(3H,s), 3.50(1H,d,10Hz), 3.57(1H,d,10Hz), 4.20(1H,m), 5.19(1H,m).

EXAMPLE 1c

4-O-(Chloroacetylcarbamoyl)-2-(1,2-epoxy-1,5-dimethyl-4-hexenyl)-3-methoxy-1-chloromethyl-1,4-cyclohexanediol To a solution of O-(chloroacetylcarbamoyl)fumagillol (100 mg) in methanol (2 ml) was added 0.4N hydrochloric acid (1 ml), which was stirred for one hour at room temperatures. Resulting precipitates were collected by filtration and recrystallized from methanol-water to afford 4-O-(chloroacetylcarbamoyl)-2(1,2-epoxy-1,5-dimethyl-4-hexenyl)-3-methoxy-1-chloromethyl-1,4-cyclohexanediol (96 mg, yield 90%) colorless crystals.

NMR spectrum (δ value; CDCl₃) 1.43(1H,m), 1.50(3H,s), 1.74(3H,s), 1.5 to 2.6(6H,m), 1.95(1H,t,6Hz), 3.30(1H,m), 3.32(3H,s), 3.49(1H,d,11Hz), 3.87(1H,d,11Hz), 4.12(1H,br s), 4.52(2H,s), 5.18(1H,m), 5.45(1H,m), 8.06(1H,br s).

EXAMPLE 2

4-O-(Acryloylcarbamoyl)-2-(1,2-epoxy-1,5-dimethyl-4-hexenyl)-3-methoxy-1-chloromethyl-1,4-cyclohexanediol To a solution of 2-(1,2-epoxy-1,5-dimethyl-4-hexenyl)-3-methoxy-1-chloromethyl-1,4-cyclohexanediol (418 mg) in dichloromethane (5 ml) was added dropwise acryloylisocyanate (300 mg). The mixture was stirred for 30 minutes at room temperatures. To the reaction mixture was added water, which was subjected to extraction with ethyl acetate. The extract solution was washed with a saturated aqueous solution of sodium hydrogencarbonate and a saturated aqueous saline solution, followed by drying over anhydrous magnesium sulfate. The solvent was distilled off under reduced pressure, and the residue was purified by means of a silica gel column chromatography (carrier 20 g, developing solvent: hexane-ethyl acetate=4:1) to afford 4-O-(acryloylcarbamoyl)-2-(1,2-epoxy-1,5-dimethyl-4-hexenyl)-3-methoxy-1-chloromethyl-1,4-cyclohexanediol (200 mg, yield 38%) as colorless crystals.

NMR spectrum (δ value; CDCl₃): 1.50(3H,s), 1.66(3H,s), 1.74(3H,s), 1.35 to 2.6(7H,m), 2.96(1H,t,7Hz), 3.30(1H,m), 3.33(3H,s), 3.48(1H,d,11Hz), 3.87(1H,d,11Hz), 4.12(1H,br s), 5.18(1H,m),5.45(1H,m), 5.91(1H,dd,11Hz,2Hz), 6.55(1H,dd,17Hz,2Hz), 7.08(1H,dd,17Hz,11Hz), 7.64(1H,br s).

EXAMPLE 3

4-O-(methacryloylcarbamoyl)-2-(1,2-epoxy-1,5-dimethyl-4-hexenyl)-3-methoxy-1-chloromethyl-1,4-cyclohexanediol As in Example 2, a mixture of 2-(1,2-epoxy-1,5-dimethyl-4-hexenyl)-3-methoxy-1-chloromethyl-1,4-cyclohexanediol (1.13 g) and methacryloylisocyanate (800 mg) was stirred for 30 minutes at room temperatures. The reaction mixture was purified by means of a silica gel column chromatography (carrier 50 g, developing solvent:hexane-ethyl acetate=3:1) to afford 4-O-(methacryloylcarbamoyl)-2-(1,2-epoxy-1,5-dimethyl-4-hexenyl)-3-methoxy-1-chloromethyl-1,4-cyclohexanediol (520 mg, yield 34%) as colorless crystals.

NMR spectrum (δ value; CDCl₃):1.51(3H,s), 1.66(3H,s), 1.74(3H,s), 2.02(3H,s), 1.2 to 2.6(7H,m), 2.97(1H,t,6Hz), 3.3 to 3.4(1H,m), 3/34(3H,s), 3.54(1H,d,11Hz), 3.86(1H,d,11Hz), 4.11(1H,br s), 5.18(1H,m), 5.50(1H,d,3Hz), 5.60(1H,d,2Hz), 5.78(1H,s), 7.81(1H,s).

EXAMPLE 4

4-O-(3-Chloro-2-methyl-propionylcarbamoyl)-2-(1,2-epoxy-1,5-dimethyl-4-hexenyl)-3-methoxy-1-chloromethyl-1,4-cyclohexanediol As in Example 2, 2-(1,2-epoxy-1,5-dimethyl-4-hexenyl)-3-methoxy-1-chloromethyl-1,4-cyclohexanediol (1.13 g) and methacryloylisocyanate (800 mg) were stirred for 30 minutes at room temperatures. The resultant product was purified by means of a silica gel column chromatography (carrier 50 g, developing solvent-:hexane-ethyl acetate=4:1) to afford 4-O-(3-chloro-2-methyl-propionylcarbamoyl)-2-(1,2-epoxy-1,5-dimethyl-4-hexenyl)-3-methoxy-1-chloromethyl-1,4-cyclohexanediol (281 mg, yield 17%) as colorless crystals.

NMR spectrum (δ value;CDCl₃): 1.31(3H,d,7Hz), 1.50(3H,s), 1.75(3H,s), 1.2 to 2.55(7H,m), 2.97(1H,t,6Hz), 3.33(3H,s), 3.49(1H,d,11Hz), 3.87(1H,d,11Hz), 3.25 to 4.3(4H,m), 4.11(1H,br s), 5.18(1H,m), 5.45(1h,d,3Hz), 7.82(1H,br s).

EXAMPLE 5

4-O-Phenylthioacetylcarbamoyl)-2-(1,2-epoxy-1,5-dimethyl-4-hexenyl)-3-methoxy-1-phenylthiomethyl-1,4-cyclohexanediol To a solution of O-chloroacetylcarbamoylfumagillol (122 mg) in DMF (2 ml) was added thiophenol.sodium salt (400 mg), and the mixture was stirred for 30 minutes at room temperatures. The reaction mixture was diluted with ethyl acetate, and the organic layer was washed with water and a saturated aqueous saline solution, followed by drying over magnesium sulfate. The solvent was distilled off under reduced pressure, then the residue was purified by means of a silica gel column chromatography (carrier 10 g, developing solvent:hexane-ethyl acetate=5:1) to afford 4-O-(phenylthioacetylcarbamoyl)-2-(1,2-epoxy-1,5-dimethyl4-hexenyl)-3-methoxy-1-phenylthiomethyl-1,4-cyclohexanediol (181 mg, yield 99%) as colorless powder.

NMR spectrum (δ value; CDCl₃): 1.45(3H,s), 1.65(3H,s), 1.72(3H,s), 1.2 to 2.5(7H,m), 2.96(1H,t,7Hz), 3.31(3H,s), 3.39(3H,m), 3.98(1H,d,14Hz), 4.00(1H,br s), 4.08(1H,d,14Hz), 5.18(1H,br s,7Hz), 5.44(1H,br s), 7.1 to 7.5(10H,m), 8.29(1H,br s).

EXAMPLE 6

4-O-(1-naphthylthioacetylcarbamoyl)-2-(1,2-epoxy-1,5-dimethyl-4-hexenyl)-3-methoxy-1-(1-naphthylthuiomethyl)-1,4-cyclohexanediol As in Example 5, 0-chloroacetylcarbamoyl fumagillol (129 mg) and 1-naphthylthiol.sodium salt (302 mg) were stirred for 10 minutes at room temperatures, and the resultant was purified by means of a silica gel column chromatography (carrier 10 g, developing solvent:hexane-ethyl acetate=4:1) to afford 4-O-(1-naphthylthioacetylcarbamoyl)-2-(1,2-epoxy-1,5-dimethyl-4-hexenyl)-3-methoxy-1-(1-napthylthiomethyl)-1,4-cyclohexanediol (207 mg, yield 94%) as colorless powder.

NMR spectrum (δ value; CDCl$_3$): 1.46(3H,s), 1.64(3H,s), 1.72(3H,s), 1.2 to 1.95(4H,m), 2.05 to 2.55(3H,m), 2.96(1H,t,6Hz), 3.11(3H,s], 3.2 to3.4(1H,m), 3.40(1H,d,13Hz), 3.43(1H,d,13Hz),4.02(1H,d,15Hz), 4.05(1H,br s), 4.13(1H,d,15Hz), 5.17(1H,m), 5.42(1H,m), 7.3 to 7.95(13H,m), 8.44(2H,m).

EXAMPLE 7

4-O-(8-Quinolylthioacetylcarbamoyl)-2-(1,2-epoxy-1,5-dimethyl-4-hexenyl]-3-methoxy-1-(8-quinolylthiomethyl)-1,4-cyclohexanediol As in Example 5, O-chloroacetylcarbamoyl fumagillol (119 mg) and 8-mercaptoquinoline.sodium salt (357 mg) were stirred for 30 minutes at room temperatures. The resultant product was purified by means of a silica gel column chromatography (carrier 10 g, developing solvent:hexane-ethyl acetate=7:3) to afford 4-O-(8-quinolylthioacetylcarbamoyl)-2-(1,2-epoxy-1,5-dimethyl-4-hexenyl)-3-methoxy-1-(8-quinolylthiomethyl)-1,4-cyclohexanediol (181 mg, yield 89%) as colorless powder.

NMR spectrum (δ value; CDCl$_3$): 1.48(3H,s), 1.82(3H,br s), 1.93(3H,br s), 1.2 to 2.6(7H,m), 2.97(1H,m), 3.39(3H,s), 3.3 to 3.6(3H,m), 3.93(1H,d,15Hz), 4.01(1H,d,15Hz), 4.28(1H,br s), 5.12(1H,m), 5.56(1H,m), 7.4 to 7.95(8H,m), 8.1 to 8.25(2H,m), 8.86(1H,m), 9.17(1H,dd,4Hz,2Hz), 10.94(1H,br s).

EXAMPLE 8

4-O-carbamoyl-2-(1,2-epoxy-1,5-dimethyl-4-hexenyl)-3-methoxy-1-(8-quinolylthiomethyl)-1,4-cyclohexanediol As in Example 5, O-carbamoyl fumagillol (200 mg) and 8-mercaptoquinoline.sodium salt (300 mg) were stirred for one hour at room temperatures. The resultant product was purified by means of a silica gel column chromatography (carrier 10 g, developing solvent: hexane - ethyl acetate=1:2) to afford 4-O-carbamoyl-2-(1,2-epoxy-1,5-dimethyl-4-hexenyl)-3-methoxy-1-(8-quinolylthiomethyl)-1,4-cyclohexanediol (233 mg, yield 78%) as colorless powder.

NMR spectrum (δ value; CDCl$_3$): 1.48(3H,s), 1.62(6H,br s), 1.2 to 2.6(7H,m), 2.95(1H,m), 3.39(3H,s), 3.3 to 3.4(2H,m), 3.47(1H,d,12Hz), 4.26(1H,m), 4.79(1H,br s), 4.85(2H,br s), 5.15(1H,br s), 5.39(1H,m), 7.4 to 7.5(2H,m), 7.55 to 7.8(2H,m), 8.18(1H,d,8Hz), 8.95(1H,dd,4Hz,2Hz).

EXAMPLE 9

4-O-Carbamoyl-2-(1,2-epoxy-1,5-dimethyl-4-hexenyl)-3-methoxy-1-methylthiomethyl-1,4-cyclohexanediol To a solution of O-chloroacetylcarbamoyl fumagillol (209 mg) in ethanol (2 ml) was added a 15% aqueous solution of methanethiol.sodium salt (500 μl), and the mixture was stirred for one hour at room temperatures. The reaction mixture was concentrated, to which was added ethyl acetate. The organic layer was washed with water and a saturated aqueous solution of sodium chloride, followed by drying over anhydrous magnesium sulfate. The solvent was distilled off under reduced pressure, and the residue was purified by means of a silica gel column chromatography (carrier 10 g, developing solvent: hexane-ethyl acetate=2:1) to afford 4-O-carbamoyl-2-(1,2-epoxy-1,5-dimethyl-4-hexenyl) -3-methoxy-1-methylthiomethyl-1,4-cyclohexanediol (136 mg: yield 70%) as colorless powder.

NMR spectrum (δ value; CDCl$_3$): 1.48(3H,s), 1.67(3H,s), 1.74(3H,s), 1.2 to 1.9(5H,m), 2.18(1H,m), 2.21(3H,s), 2.46(1H,m), 2.85(1H,d,14Hz), 2.96(1H,m), 2.98(1H,d,14Hz), 3.31(1H,m), 3.33(3H,s), 4.71(2H,br s), 5.20(1H,m), 5.33(1H,m).

EXAMPLE 10

2-(1,2-Epoxy-1,5-dimethyl-4-hexenyl)-3-methoxy-1-methylthiomethyl-1,4-cyclohexanediol Fumagillol (3.00 g) was dissolved in DMF (6 ml), to which was added thiomethoxide (2.23 g). The mixture was stirred for 30 minutes, to which was added water to suspend the reaction. The product was extracted with isopropylether. The extract solution was washed with a saturated aqueous solution of sodium hydrogencarbonate and a saturated aqueous saline solution, followed by drying over anhydrous magnesium sulfate. The solvent was distilled off under reduced pressure, then the residue was purified by means of a silica gel column chromatography (carrier 150 g, developing solvent : ethyl acetate - hexane=1:2), followed by recrystallization from hexane to afford 2-(1,2-epoxy-1,5-dimethyl-4-hexenyl)-3-methoxy-1-methylthiomethyl-1,4-cyclohexanediol (2.43 g:yield 69%) as colorless powder, m.p. 52° to 53° C.

NMR spectrum (δ value; CDCl$_3$): 1.45(3H,s), 1.55(1H,m), 1.66(3H,s), 1.74(3H,s), 1.65 to 1.90(4H,m), 2.08 to 2.55(2H,m), 2.80 to 3.02(3H,m), 3.30(1H,m), 3.35(3H,s), 4.22(1H,m), 5.19(1H,m).

$[\alpha]_D^{26}$ −57.5° (c 0.20, CHCl$_3$).

Elemental analysis:C$_{17}$H$_{30}$O$_4$S
Calcd. C:61.78%, H:9.15%,
Found C:61.66%, H:9.30%.

EXAMPLE 11

4-O-Acetyl-2-(1,2-epoxy-1,5-dimethyl-4-hexenyl)-3-methoxy-1-methylthiomethyl-1,4-cyclohexanediol In dichloromethane (5 ml) was dissolved 2-(1,2-epoxy-1,5-dimethyl-4-hexenyl)-3-methoxy-1-methylthiomethyl-1,4-cyclohexanediol (620 mg). To the solution were added dimethylaminopyridine (252 mg) and acetic anhydride (0.20 ml), then the mixture was stirred for one hour. The reaction mixture was diluted with ethyl acetate (70 ml), which was washed with water, a 10% aqueous solution of citric acid and a saturated aqueous saline solution, followed by drying over anhydrous magnesium sulfate. The solvent was distilled off under reduced pressure. The residue was purified by means of a silica gel column chromatography (carrier 30 g, developing solvent: ethyl acetate - hexane=1:2), followed by crystallization from hexane to afford 4-O-acetyl-2-(1,2-epoxy-1,5-dimethyl-4-hexenyl)-3-methoxy-1-mothylthiomethyl-1,4-cyclohexanediol (730 mg: yield 100%) as colorless crystals, m.p. 73° to 74° C.

NMR spectrum (δ value; CDCl$_3$): 1.48(3H,s), 1.66(3H,s), 1.74(3H,s), 1.60 to 1.90(4H,m), 2.00 to 2.55(3H,m), 2.12(3H,s), 2.21(3H,s), 2.85 to 3.00(3H,m), 3.29(3H,s), 3.34(1H,m), 5.20(1H,m), 5.47(1H,m).

$[\alpha]_D^{26}$ −71.8° (c 0.22, CHCl$_3$).

Elemental analysis:C$_{19}$H$_{32}$O$_5$S: Calcd. C:61.26%, H:8.66%, Found C:61.35%, H:8.86.

EXAMPLE 12

4-O-(Chloroacetylcarbamoyl)-2-(1,2-epoxy-1,5-dimethyl-4-hexenyl)-3-methoxy-1-methylthiomethyl-1,4-cyclohexanediol In dichloromethane (15 ml) was dissolved 2-(1,2-epoxy-1,5-dimethyl-4-hexenyl)-5-methoxy-1-methylthiomethyl-1,4-cyclohexanediol (1.50 g). To the solution was added dropwise, under ice-cooling, chloroacetyl isocyanate (0.46 ml). The mixture was stirred for 20 minutes, which was diluted with ethyl acetate (60 ml) and washed with a saturated aqueous solution of sodium hydrogencarbonate and a saturated aqueous saline solution, followed by drying over anhydrous magnesium sulfate. The solvent was distilled off under reduced pressure, and the residue was purified by means of a silica gel column chromatography (carrier 75 g, developing solvent : ethyl acetate - hexane = 1:2), followed by crystallization from ether-hexane to afford 4-O-(chloroacetylcarbamoyl)-2-(1,2-epoxy-1,5-dimethyl-4-hexenyl)-3-methoxy-1-methylthiomethyl-1,4-cyclohexanediol (1.70 g: yield 83%) as colorless crystals, m.p. 101° to 102° C.

NMR spectrum ($\delta$ value; $CDCl_3$): 1.46(3H,s), 1.66(3H,s), 1.74(3H,s), 1.60 to 1.92(4H,m), 2.05 to 2.55(3H,m), 2.21(3H,s), 2.84(1H,d,13Hz), 2.93(1H,t,7Hz), 2.99(1H,d,13Hz), 3.32(3H,s), 3.34(1H,m), 4.51(2H,s), 5.19(1H,m), 5.45(1H,m).

$[\alpha]_D^{26} -81.5°$ (c 0.20, $CHCl_3$).

Elemental analysis for $C_{20}H_{32}NO_6SCl$: Calcd. C:53.38%, H:7.17%, N:3.11% Found C:53.34%, H:7.14%, N:3.03%

EXAMPLE 13

4-O-(Chloroacetylcarbamoyl)-2-(1,2-epoxy-1,5-dimethyl-4-hexenyl)-3-methoxy-1-dimethylsulfoniomethyl-1,4-cyclohexanediol iodide In acetonitrile (2 ml) was dissolved 4-O-(chloroacetylcarbamoyl)-2-(1,2-epoxy-1,5-dimethyl-4-h-exenyl)-3-methoxy-1-methylthiomethyl-1,4-cyclohexanediol (500 mg). To the solution was added methyl iodide (0.82 ml), and the mixture was stirred for 8 hours. The solvent was distilled off under reduced pressure. The residue was pulverized by the addition of ether to afford 4-O-(N-chloroacetylcarbamoyl)- 2-(1,2-epoxy-1,5-dimethyl-4-hexenyl)-3-methoxy-1-dimethylsulfoniomethyl-1,4-cyclohexanediol iodide (701 mg: yield 100%) as pale yellow powder.

NMR spectrum ($\delta$ value; $CD_3OD$): 1.47(3H,s), 1.69(3H,s), 1.75(3H,s), 1.65 to 1.95(4H,m), 2.10 to 2.60(3H,m), 3.01(3H,s), 3.07(3H,s), 3.12(1H,t,6Hz), 3.46(1H,m), 3.70(1H,d,13Hz), 4.03(2H,s), 4.05(1H,d,13Hz), 5.24(1H,m), 5.48(1H,m).

$[\alpha]_D^{26} -49.0°$ (c 0.20, $CHCl_3$).

Elemental analysis for $C_{21}H_{35}NO_6SCII.4H_2O$: Calcd. C:37.99%, N:2.11%, Found C:38.07%, N:2.16%

EXAMPLE 14

4-O-acetyl-2-(1,2-epoxy-1,5-dimethyl-4-hexenyl)-3-methoxy-1-dimethylsulfoniomethyl-1,4-cyclohexanediol iodide As in Example 13, 4-acetoxy-2-(1,2-epoxy-1,5-dimethyl-4-hexenyl)-3-methoxy-1-dimethylsulfoniomethyl-1,4-cyclohexanediol iodide (558 mg: yield 82%) was obtained as pale yellow powder from 4-O-acetyl-2-(1,2-epoxy-1,5-dimethyl-4-hexenyl)-3-methoxy-1-methylthiomethyl-1,4-cyclohexanediol (490 mg).

NMR spectrum ($\delta$ value; $CD_3OD$): 1.46(3H,s), 1.69(3H,s), 1.75(3H,s), 1.65 to 1.85(4H,m), 2.05 to 2.60(3H,m), 2.08(3H,s), 2.98(3H,s), 3.06(3H,s), 3.12(1H,t,6Hz), 3.30(3H,s), 3.44(1H,m), 3.74(1H,d,13Hz), 4.03(1H,d,13Hz), 5.24(1H,m), 5.51(1H,m).

$[\alpha]_D^{26} -58.6°$ (c 0.22, $CHCl_3$).

EXAMPLE 15

4-O-(Chloroacetylcarbamoyl)-2-(1,2-epoxy-1,5-dimethyl-4-hexenyl)-3-methoxy-1-ethylmethylsulfoniomethyl-1,4-cyclohexanediol iodide As in Example 13, 4-O-(chloroacetyl-carbamoyl)-2-(1,2-epoxy-1,5-dimethyl-4-hexenyl)-3-methoxy-1-ethylmethylsulfoniomethyl-1,4-cyclohexanediol iodide (59 mg: yield 44%) was obtained as pale yellow powder from 4-O-(chloroacetylcarbamoyl)-2-(1,2-epoxy-1,5-dimethyl-4-hexenyl)-3-methoxy-1-methylthiomethyl-1,4-cyclohexanediol (150 mg).

NMR spectrum ($\delta$ value; $CD_3OD$): 1.35 tol.50(6H,m), 1.69(3H,s), 1.75(3H,s), 1.65 to 1.95(4H,m), 2.05 to 2.60(3H,m), 2.97(1.5H,s), 3.06(1.5H,s), 3.12(1H,m), 4.03(2H,m), 4.45(1H,m), 5.25(1H,m), 5.45(1H,m).

$[\alpha]_D^{26} -62.7°$ (c 0.22, $CHCl_3$).

Elemental analysis for $C_{22}H_{37}NO_6SCII$: Calcd. C:43.61%, H:6.15%, N:2.31%, Found C:43.83%, H:6.19%, N:2.39%.

EXAMPLE 16

4-O-(N-chloroacetylcarbamoyl)-2-(1,2-epoxy-1,5-dimethyl-4-hexenyl)-3-methoxy-1-benzylmethylsulfoniomethyl-1,4-cyclohexanediol bromide As in Example 13, 4-O-(N-chloroacetyl-carbamoyl)-2-(1,2-epoxy-1,5-dimethyl-4-hexenyl)-3-methoxy-1-benzylmethylsulfoniomethyl-1,4-cyclohexanediol bromide (152 mg: yield 73%) was obtained as colorless powder from 4-O-(N-chloroacetylcarbamoyl)-2-(1,2-epoxy-1,5-dimethyl-4-hexenyl)-3-methoxy-1-methylthiomethyl-1,4-cyclohexanediol (150 mg).

NMR spectrum ($\delta$ value; $CD_3OD$): 1.42(3H,m), 1.68(3H,s), 1.65 to 2.00(4H,m), 2.10 to 2.60(3H,m), 2.82(1.5H,s), 3.00(1.5H,s), 3.12(1H,m), 3.30 to 3.75(8H,m), 4.03(1H,m), 4.45 to 5.05(4H,m), 5.25(1H,m), 5.45(1H,m).

$[\alpha]_D^{26} -43.0°$ (c 0.22, $CHCl_3$).

Elemental analysis for $C_{27}H_{39}NO_6SBrCl.2.5H_2O$: Calcd. C:48 69%, H:6.66%, N:2.10% Found C:48.66%, H:6.35%, N:2.29%.

EXAMPLE 17

4-O-(Chloroacetylcarbamoyl)-2-(1,2-epoxy-1,5-dimethyl-4-hexenyl)-3-methoxy-1-(2-propinyl)-methylsulfoniomethyl-1,4-cyclohexanediol bromide As in Example 13, from 4-O-(chloroacetyl-carbamoyl)-2-(1,2-epoxy-1,5-dimethyl-4-hexenyl)-3-methoxy-1-methylthiomethyl-1,4-cyclohexanediol (150 mg) was obtained 4-O-0-(chloroacetylcarbamoyl)-2-(1,2-epoxy-1,5-dimethyl-4-hexenyl)-3-methoxy-1-(2-propinyl)methylsulfoniomethyl-1,4-cyclohexanediol bromide (97 mg: yield 51%) as pale yellow powder.

NMR spectrum ($\delta$ value; $CD_3OD$): 1.40(1.5H,s), 1.45(1.5H,s), 1.68(3H,s), 1.74(3H,s), 1.65 to 2.00(4H,m), 2.10 to 2.60(3H,m), 2.90 to 3.90(9H,m), 4.18(2H,m), 4.44(1H,s), 5.25(1H,m), 5.45(1H,m).

$[\alpha]_D^{26}$ −43.0° (c 0.20, CHCl$_3$).

Elemental analysis for C$_{23}$H$_{35}$NO$_6$SBrCl: Calcd. C:48.55%, H:6.20%, N:2.46%, Found C:48.48% H:6.21%, N:2.59%.

EXAMPLE 18

4-O-(1-Naphthyl)carbamoyl-2-(1,2-epoxy-1,5-dimethyl-4-hexenyl)-5-methoxy-1-methylthiomethyl-1,4-cyclohexanediol As in Example 12, 4-O-(1-naphthyl)carbamoyl-2-(1,2-epoxy-1,5-dimethyl-4-hexenyl)-5-methoxy-1-methylthiomethyl-1,4-cyclohexanediol (378 mg: yield 83%) was obtained as colorless powder from 2-(1,2-epoxy-1,5-dimethyl-4-hexenyl)-3-methoxy-1-methylthiomethyl-1,4-cyclohexanediol (300 mg).

NMR spectrum (δ value; CDC$_3$): 1.45(3H,br s), 1.67(3H,s), 1.75(3H,s), 1.65 to 2.00(4H,m), 2.05 to 2.55(3H,m), 2.17(3H,br s), 2.75 to 3.05(2H,m), 3.32(1H,m), 3.37(3H,m), 5.21(1H,m), 5.51(1H,m), 7.44 to 8.00(7H,m)

$[\alpha]_D^{26}$ −85.5° (c 0.22, CHCl$_3$).

EXAMPLE 19

4-O-(1-Naphthyl)carbamoyl-2-(1,2-epoxy-1,5-dimethyl-4-hexenyl)-3-methoxy-1-dimethylsulfoniomethyl-1,4-cyclohexanediol iodide As in Example 13, from 4-O-(1-naphthyl)-carbamoyl-2-(1,2-epoxy-1,5-dimethyl-4-hexenyl)-3-methoxy-1-methylthiomethyl-1,4-cyclohexanediol (150 mg) was obtained 4-O-(1-naphthyl)carbamoyl-2-(1,2-epoxy-1,5-dimethyl-4-hexenyl)-3-methoxy-1-dimethylsulfoniomethyl-1,4-cyclohexanediol iodide (177 mg: yield 92%) as pale yellow powder.

NMR spectrum (δ value; CD$_3$OD): 1.44(3H,br s), 1.69(3H,s), 1.76(3H,s), 1.70 to 2.00(4H,m), 2.10 to 2.60(3H,m), 2.98(3H,s), 3.06(3H,s), 3.12(1H,m), 3.39(3H,s), 3.45(2H,m), 4.02(1H,m), 5.27(1H,m), 5.45(1H,m).

$[\alpha]_D^{26}$ −51.0° (c 0.22, CHCl$_3$).

Elemental analysis for C$_{29}$H$_4$ONO$_5$SI: Calcd. C:54.29%, H:6.28%, N:2.18%, Found C:54.17%, H:6.35%, N:2.08%

EXAMPLE 20

4-O-(2-benzothiazoyl)thioacetylcarbamoyl-2-(1,2-epoxy-1,5-dimethyl-4-hexenyl)-3-methoxy-1-dimethylsulfoniomethyl-1,4-cyclohexanediol iodide In methanol (1 ml) was dissolved 4-O-(chloroacetylcarbamoyl)-2-(1,2-epoxy-1,5-dimethyl-4-hexenyl)-3-methoxy-1-dimethylsulfoniomethyl-1,4-cyclohexanediol iodide (200 mg). To the solution was added 2-mercaptobenzothiazol.sodium salt (127 mg), and the mixture was stirred for 30 minutes. The reaction mixture was diluted with ethyl acetate (70 ml), then washed with water, a saturated aqueous solution of sodium hydrogencarbonate and a saturated aqueous saline solution,followed by drying over anhydrous magnesium sulfate. The solvent was distilled off under reduced pressure, then the residue was purified by means of a silica gel column chromatography (carrier 10 g, developing solvent: chloroform-methanol=10:1) to afford 4-O-(2-benzothiazoyl)thioacetylcarbamoyl-2-(1,2-epoxy-1,5-dimethyl-4-hexenyl)-3-methoxy-1sulfoniomethyl-1,4-cyclohexanediol iodide (65.8 mg: yield 26%) as colorless powder.

NMR spectrum (δ value: CD$_3$OD): 1.48(3H,s), 1.64(3H,s), 1.73(3H,s), 1.65 to 1.90(5H,m), 2.00 to 2.55(2H,m), 2.96(1H,m), 3.06(3H,s), 3.20(1H,m), 3.27(3H,s), 3.31(3H,s), 3.81(1H,d,14Hz), 4.40 to 4.70(3H,m), 5.14(1H,m), 5.42(1H,m), 7.25 to 7.50(2H,m), 7.15(1H,d,7Hz), 7.89(1H,d,8Hz).

$[\alpha]_D^{26}$ −4.7° (c 0.10, CHCl$_3$).

EXAMPLE 21

2-(1,2-epoxy-1,5-dimethyl-4-hexenyl)-3-methoxy-1-phenylthiomethyl-1,4-cyclohexanediol To methanol (5 ml) was added, under ice-cooling, 60% sodium hydride (213 mg), and the mixture was stirred for 5 minutes at room temperatures, to which was then added thiophenol (0.55 ml), followed by stirring for 15 hours. To the resultant mixture was added fumagillol (500 mg), which was stirred for 30 minutes, followed by adding water to suspend the reaction. The product was extracted with ethyl acetate, and the extract solution was washed with a saturated aqueous solution of sodium hydrogencarbonate and a saturated aqueous saline solution, followed by drying over anhydrous magnesium sulfate. The solvent was distilled off under reduced pressure, and the residue was purified by means of a silica gel column chromatography (carrier 25 g, developing solvent: ethyl acetate-hexane=1:2), followed by crystallization from isopropylether to afford 2-(1,2-epoxy-1,5-dimethyl-4-hexenyl)- 3-methoxy-1-phenylthiomethyl-1,4-cyclohexanediol (660 mg: yield 95%) as colorless crystals, m.p. 94° to 96° C.

NMR spectrum (δ value; CDCl$_3$) 1.45(3H,s), 1.45 to 1.95(4H,m), 1.66(3H,s), 1.73(3H,s), 2.05 to 2.55(3H,m), 2.99(1H,m), 3.20 to 3.45(3H,m), 3.35(3H,s), 4.22(1H,m), 5.19(1H,m], 7.10 to 7.45(5H,m).

$[\alpha]_D^{26}$ −41.4° (c 0.21, CHCl$_3$)

Elemental analysis for C$_{22}$H$_{32}$O$_4$S: Calcd. C:67.31%, H:8.22%, Found C:67.36%, H:8.30%.

EXAMPLE 22

4-O-(Chloroacetylcarbamoyl)-2-(1,2-epoxy-1,5-dimethyl-4-hexenyl)-3-methoxy-1-phenylthiomethyl-1,4-cyclohexanediol As in Example 12, from 2-(1,2-epoxy-1,5-dimethyl-4-hexenyl)-3-methoxy-1-phenylthiomethyl-1,4-cyclohexanediol (450 mg) was obtained 4-O-(chloroacetylcarbamoyl)-2-(1,2-epoxy-1,5-dimethyl-4-hexenyl)-3-methoxy-1-phenylthiomethyl-1,4-cyclohexanediol (541 mg: yield 92%) as colorless powder.

NMR spectrum (δ value; CDCl$_3$): 1.46(3H,s), 1.66(3H,s), 1.73(3H,s), 1.50 to 1.92(4H,m), 2.00 to 2.55(3H,m), 2.96(1H,t,6Hz), 3.23(3H,s), 3.38(2H,s), 3.25 to 3.50(1H,m), 4.52(2H,s), 5.18(1H,m), 5.45(1H,m), 7.15 to 7.45(5H,m).

$[\alpha]_D^{26}$ −56.0° (c 0.21, CHCl$_3$).

Elemental analysis for C$_{25}$H$_{34}$NO$_6$SCl: Calcd. C:58.64%, H:6.69%, N:2.74%, Found C:58.41%, H:6.69%, N:2.79%

EXAMPLE 23

4-O-(Chloroacetylcarbamoyl)-2-(1,2-epoxy-1,5-dimethyl-4-hexenyl)-3-methoxy-1-phenylsulfinylmethyl-1,4-cyclohexanediol In dichloromethane (2 ml) was dissolved 4-O-(chloroacetylcarbamoyl)-2-(1,2-epoxy-1,5-dimethyl-4- h-exenyl)-3-methoxy-1-phenylthiomethyl-1,4-cyclohexanediol (200 mg). To the solution was added, under ice-cooling, m-chloroperbenzoic acid (80.9 mg), and the mixture was stirred for 30 minutes. The reaction mixture was diluted with ethyl acetate (70 ml), which was washed with a saturated aqueous solution of sodium hydrogencarbonate and a saturated aqueous saline solution, followed by drying over anhydrous magnesium sulfate. The solvent was distilled off under reduced pressure. The residue was then purified by means of a silica gel column chromatography (carrier 10 g, developing solvent: ethyl acetate - hexane=1:2) to afford 4-O-(chloroacetylcarbamoyl)-2-(1,2-epoxy-1,5-dimethyl-4-hexenyl)-3-methoxy-1-phenylsulfinylmethyl-1,4-cyclohexanediol (175 mg: yield 85%) as colorless powder.

NMR spectrum ($\delta$ value; CDCl$_3$): 1.49(3H,s), 1.65(3H,s), 1.73(3H,s), 1.55 to 2.55(7H,m), 2.98(1H,t,6Hz), 3.31(1H,d,14Hz), 3.25 to 3.45(5H,m), 4.47(2H,s), 5.05 to 5.25(1H,m), 5.49(1H,m), 7.50 to 7.70(5H,m).

$[\alpha]_D^{26}$ −88.6° (c 0.22, CHCl$_3$).

Elemental analysis for C$_{25}$H$_{34}$NO$_7$SCl.0.5H$_2$O: Calcd. C:55.91%, H:6.57%, N:2.61%, Found C:55.18%, H:6.39%, N:2.68%.

EXAMPLE 24

4-O-(chloroacetylcarbamoyl)-2-(1,2-epoxy-1,5-dimethyl-4-hexenyl)-3-methoxy-1-iodomethyl-1,4-cyclohexanediol As in Example 12, from 2-(1,2-epoxy-1,5-dimethyl-4-hexenyl)-3-methoxy-1-iodomethyl-1,4-cyclohexanediol (200 mg) was obtained 4-O-(N-chloro-acetylcarbamoyl)-2-(1,2-epoxy-1,5-dimethyl-4-hexenyl)-3-methoxy-1-iodomethyl-1,4-cyclohexanediol (222 mg: yield 86%) as colorless crystals, m.p. 140° to 141° C.

NMR spectrum ($\delta$ value; CDCl$_3$): 1.45 to 2.00(4H,m), 1.53(3H,s), 1.67(4H,s), 1.75(3H,s), 2.10 to 2.55(3H,m), 3.30(1H,m), 3.32(3H,s), 3.51(1H,d,10Hz), 3.58(1H,d,10Hz), 4.51(2H,s), 5.18(1H,m), 5.44(1H,m).

$[\alpha]_D^{26}$ −74.5° (c 0.22, CHCl$_3$).

Elemental analysis for C$_{19}$H$_{29}$NO$_6$ClI: Calcd. C:43.07%, H:5.52%, N:2.64%, Found C:42.81%, H:5.45%, N:2.65%.

EXAMPLE 25

4-O-Acetyl-2-(1,2-epoxy-1,5-dimethyl-4-hexenyl)-1-iodomethyl-3-methoxy-1,4-cyclohexanediol In dichloromethane (5 ml) was dissolved 2-(1,2-epoxy-1,5-dimethyl-4-hexenyl)-3-methoxy-1-iodomethyl-1,4-cyclohexanediol (2.08 g). To the solution were added dimethylaminopyridine (0.74 g) and acetic anhydride (0.58 ml). The mixture was stirred for 30 minutes. The reaction mixture was diluted with ethyl acetate (50 ml), which was washed with a saturated aqueous solution of sodium hydrogencarbonate and a saturated aqueous saline solution, followed by drying over anhydrous magnesium sulfate. The solvent was distilled off under reduced pressure, then the solvent was purified by means of a silica gel column chromatography (carrier 100 g, developing solvent: ethyl acetate - hexane=1:3) to afford 4-O-acetyl-2-(1,2-epoxy-1,5-dimethyl-4-hexenyl)-1-iodomethyl-3-methoxy-1,4-cyclohexanediol (2.19 g: yield 95%) as a colorless oily product.

NMR spectrum ($\delta$ value; CDCl$_3$): 1.52(3H,s), 1.53(1H,m), 1.66(3H,s), 1.74(3H,s), 1.65 to 2.00(4H,m), 2.12(3H,s), 2.10 to 2.60(3H,m), 2.98(1H,t,6Hz), 3.26(1H,m), 3.55(2H,s), 5.18(1H,m), 5.44(1H,m).

$[\alpha]_D^{26}$ −66.5° (c 0.20, CHCl$_3$).

EXAMPLE 26

4-(N'-Chloroacetylureido)-2-(1,2-epoxy-1,5-dimethyl-4-hexenyl)-3-methoxy-1-methylthiomethyl-1-cyclohexanol In methanol (5 ml) were dissolved 2-(1,2-epoxy-1,5-dimethyl-4-hexenyl)-3-methoxy-1-methylthiomethyl-4-oxy-1-cyclohexanol (200 mg) and ammonium acetate mg). To the solution was added sodium cyanoborohydride (40 mg), and the mixture was stirred for one hour. The solvent was distilled off under reduced pressure, and the residue was dissolved in ethyl acetate (50 ml). The solution was washed with a saturated aqueous solution of sodium hydrogencarbonate and a saturated aqueous solution of sodium chloride, followed by drying over anhydrous magnesium sulfate. The solvent was distilled off under reduced pressure, and the residue was dissolved in dichloromethane (2 ml). To the solution was added dropwise at 0° C. chloroacetylisocyanate (0.08 ml). The mixture was stirred for 15 minutes at the same temperature, which was then diluted with ethyl acetate (50 ml). The solution was washed with a saturated aqueous solution of sodium hydrogencarbonate and a saturated aqueous solution of sodium chloride, followed by drying over anhydrous magnesium sulfate. The solvent was distilled off under reduced pressure, and the residue was purified by means of a silica gel column chromatography (carrier 25 g, developing solvent: ethyl acetate-hexane=1:3) to afford 4-(N,-chloroacetylureido)-2-(1,2-epoxy-1,5-dimethyl-4-hexenyl)-3-methoxy-1-methylthiomethyl-1-cyclohexanol (129 mg: yield 45%) as colorless powder.

NMR spectrum ($\delta$ value; CDCl$_3$): 1.48(3H,s), 1.40 to 2.55(7H,m), 1.66(3H,s), 1.73(3H,s), 2.20(3H,s), 2.85(1H,d,13Hz), 2.99(1H,t,6Hz), 2.96(1H,d,13Hz), 3.32(3H,s), 3.40(1H,dd,4Hz,12Hz), 4.14(2H,s), 4.51(1H,m), 5.18(1H,m).

$[\alpha]_D^{26}$ −60.8° (c 0.21,CHCl$_3$).

Elemental analysis for C$_{20}$H$_{33}$N$_2$O$_5$Cl.0.2H$_2$O: Calcd. C:53.07%, H:7.44%, N:6.19%, Found C:52.81%, H:7.42%, N:6.57%.

EXAMPLE 27

4-(N'-chloroacetylureido)-2-(1,2-epoxy-1,5-dimethyl-4-hexenyl)-3-methoxy-1-dimethylsulfoniomethyl-1-cyclohexanol iodide As in Example 13, from 4-(N'-chloro-acetylureido)-2-(1,2-epoxy-1,5-dimethyl-4-hexenyl)-3-methoxy-1-methylthiomethyl-1-cyclohexanol (132 mg) was obtained 4-(N'-chloroacetylureido)-2-(1,2-epoxy-1,5-dimethyl-4-hexenyl)-3-methoxy-1-dimethylsulfoniomethyl-1-cyclohexanol iodide (180 mg: yield 100%) as a pale yellow powdery product.

NMR spectrum ($\delta$ value; CD$_3$OD): 1.40' to2.55(7H,m), 1.47(3H,s), 1.69(3H,s), 1.75(3H,s), 2.97(3H,s), 3.04(3H,s), 3.14(1H,t,6Hz), 3.31(3H,s), 3.51(1H,m), 3.67(1H,d,13Hz), 3.83(2H,s), 4.03(1H,d,13Hz), 4.41(1H,m), 5.24(1H,m).

Elemental analysis for C$_{21}$H$_{38}$N$_2$O$_5$SClI.4H$_2$O: Calcd. C:38.04%, N:4.23%, Found C:37.91%, N:4.41%.

EXAMPLE 28

4-O-(Chloroacetylcarbamoyl)-2-(1,2-epoxy-1,5-dimethyl-4-hexenyl)-3-methoxy-1-methylsulfinylmethyl-1,4-cyclohexanediol As in Example 23, from 2-(1,2-epoxy-1,5-dimethyl-4-hexenyl)-3-methoxy-1-methylthiomethyl-1,4-cyclohexanediol (156 mg) was obtained 4-O-(chloroacetylcarbamoyl)-2-(1,2-epoxy-1,5-dimethyl-4-hexenyl)-3-methoxy-1-methylsulfinylmethyl-1,4-cyclohexanediol (156 mg: yield 100%) as colorless powder.

NMR spectrum (δ value; CDCl$_3$): 1.45(1.5H,s), 1.50(15H,s), 1.67(3H,s), 1.74(3H,s), 1.70 to 2.60(7H,m), 2.68(1.5H,s), 2.72(1.5H,s), 2.95(1H,t,6Hz), 3.15 to 3.28(3H,m), 3.31(1.5H,s), 3.37(1.5H,s), 4.48(2H,s), 5.20(1H,m), 5.46(1H,m).

$[\alpha]_D^{26}$ −90° (c 0.20,CHCl$_3$).

Elemental analysis for C$_{20}$H$_{32}$NO$_7$SCl.H$_2$O:
Calcd. C:49.63%, H:7.08%, N:2.89%, Found C:49.49%, H:6.73%, N:2.89%.

EXAMPLE 29

4-O-(Chloroacetylcarbamoyl)-2-(1,2-epoxy-1,5-dimethyl-4-hexenyl)-3-methoxy-1-methylsulfonylmethyl-1,4-cyclohexanediol 4-O-(chloroacetylcarbamoyl)-2-(1,2-epoxy-1,5-dimethyl-4-hexenyl)-3-methoxy-1-methylsulfinylmethyl-1,4-cyclohexanediol (300 mg) was dissolved in dichloromethane (2 ml), to which was added, under ice-cooling, m-chloroperbenzoic acid (179 mg), and the mixture was stirred for one hour. The reaction mixture was diluted with ethyl acetate (70 ml), which was washed with a saturated aqueous solution of sodium hydrogencarbonate and a saturated aqueous saline solution, followed by drying over anhydrous magnesium sulfate. The solvent was distilled off under reduced pressure. The residue was purified by a silica gel column chromatography (carrier 15 g, developing solvent: ethyl acetate - hexane 2:1) to afford 4-O-(chloroacetylcarbamoyl)-2-(1,2-epoxy-1,5-dimethyl-4-h-exenyl)-3-methoxy-1-phenylsulfonylmethyl-1,4-cyclohexanediol (91 mg: yield 30%) as colorless powder.

NMR spectrum (δ value: CDCl$_3$): 1.47(3H,s), 1.67(3H,s), 1.75(3H,s), 1.70 to 2.60(7H,m), 3.00(1H,m), 3.05(3H,s), 3.25 to 3.45(2H,m), 3.33(3H,s), 3.80(1H,d,15Hz), 4.47(2H,s), 5.17(1H,m), 5.46(1H,m).

$[\alpha]_D^{26}$ −96.5° (c 0.20, CHCl$_3$).

Elemental analysis for C$_{20}$H$_{32}$NO$_8$SCl.0.7H$_2$O:
Calcd. C:48.57%, H:6.81%, N:2.83%, Found C:48.62%, H:6.57%, N:2.86%.

EXAMPLE 30

2-(1,2-Epoxy-1,5-dimethyl-4-hexenyl)-3-methoxy-1-(4-pyridyl)thiomethyl-1,4-cyclohexanediol As in Example 21, from fumagillol (1.00 g) was obtained 2-(1,2-epoxy-1,5-dimethyl)-4-hexenyl)-3-methoxy-1-(4-pyridyl)thiomethyl-1,4-cyclohexanediol (1.15 g: yield 81%) as a pale yellow oily product.

NMR spectrum (δ value; CDCl$_3$): 1.47(3H,s), 1.50 to 1.90(4H,m), 1.67(3H,s), 1.74(3H,s), 2.05 to 2.60(3H,m), 3.04(1H,t,6Hz), 3.28(1H,d,13Hz), 3,29(1H,m), 3.35(3H,s), 3.50(1H,d,13Hz), 4.23(1H,m), 5.20(1H,m), 7.19(2H,m), 8.38(2H,m).

EXAMPLE 31

4-O-(Chloroacetylcarbamoyl)-2-(1,2-epoxy-1,5-dimethyl-4-hexenyl)-1-(4-pyridyl)thiomethyl-3-methoxy-1,4-cyclohexanediol As in Example 12, from 2-(1,2-epoxy-1,5-dimethyl-4-hexenyl)-3-methoxy-1-(4-pyridyl)thiomethyl-1,4-cyclohexanediol (911 mg) was obtained 4-O-(chloroacetylcarbamoyl)-2-(1,2-epoxy-1,5-dimethyl-4-h-exenyl)-1-(4-pyridyl)thiomethyl-3-methoxy-1,4-cyclohexanediol (1.02 g: yield 83%) as colorless powder.

NMR spectrum (δ value; CDCl$_3$): 1.46(3H,s), 1.55 to 2.00(4H,m), 1.66(3H,s), 1.74(3H,s), 2.05 to 2.60(3H,m), 2.99(1H,t,6Hz), 3.25 to 3.40(2H,m), 3.33(3H,s), 3.50(1H,d,12Hz), 4.51(2H,s), 5.18(1H,m), 5.47(1H,m), 7.21(2H,m), 8.42(2H,m).

Elemental analysis for C$_{24}$H$_{33}$N$_2$O$_6$SCl.0.5H$_2$O:
Calcd. C:55.22%, H:6.55%, N:5.37%, Found C:55.07%, H:6.19%, N:5.59%.

EXAMPLE 32

4-O-(Chloroacetylcarbamoyl)-2-(1,2-epoxy-1,5-dimethyl-4-hexenyl)-3-methoxy-1-(N-methyl-4-pyridinio)-thiomethyl-1,4-cyclohexanediol iodide As in Example 13, from 4-O-(chloroacetylcarbamoyl)-2-(1,2-epoxy-1,5-dimethyl-4-hexenyl)-1-(4-pyridyl)thiomethyl-3-methoxy-1,4-cyclohexanediol (165 mg) was obtained 4-O-(chloroacetylcarbamoyl)-2-(1,2-epoxy-1,5-dimethyl-4-hexenyl)-3-methoxy-1-(N-methyl-4-pyridinio)thiomethyl-1,4-cyclohexanediol iodide (212 mg: yield 100%) as pale yellow powder.

NMR spectrum (δ value; CD$_3$OD): 1.49(3H,s), 1.55 to 2.60(7H,m), 1.68(3H,s), 1.70(3H,s), 3.13(1H,m), 3.20 to 3.60(2H,m), 3.99(1H,m), 4.03(2H,s), 4.23(3H,s), 5.25(3H,s), 5.47(1H,m), 7.99(2H,m), 8.52(2H,m).

EXAMPLE 33

2-(1,2-Epoxy-1,5-dimethyl-4-hexenyl)-3-methoxy-1-(pyrimidin-2-yl)thiomethyl-1,4-cyclohexanediol As in Example 21, from fumagillol (500 mg) was obtained 2-(1,2-epoxy-1,5-dimethyl-4-hexenyl)-3-methoxy-1-(pyrimidin-2-yl)thiomethyl-1,4cyclohexanediol (426 mg: yield 61%) as an oily product.

NMR spectrum (δ value; CDCl$_3$): 1.40 to 2.10(4H,m), 1.60(6H,s), 1.71(3H,s), 2.65(1H,d,14Hz)), 2.70 to 2.90(3H,m), 3.53(3H,s), 4.10 to 4.32(2H,m), 4.16(1H,d,15Hz), 5.23(1H,m), 6.92(1H,t,5Hz), 8.48(2H,d,5Hz).

EXAMPLE 34

4-O-(Chloroacetylcarbamoyl)-2-(1,2-epoxy-1,5-dimethyl-4-hexenyl)-3-methoxy-1-(pyrimidin-2-yl)thiomethyl-1,4-cyclohexanediol As in Example 12, from 2-(1,2-epoxy-1,5-dimethyl-4-hexenyl)-1-(pyrimidin-2-yl)thiomethyl-3-methoxy-1,4-cyclohexanediol (300 mg) was obtained 4-O-(chloroacetylcarbamoyl)- 2-(1,2-epoxy-1,5-dimethyl-4-h-exenyl)-3-methoxy-1-(pyrimidin-2-yl)thiomethyl-1,4-cyclohexanediol (344 mg: yield 88%) as pale yellow powder.

NMR spectrum (δ value; CDCl$_3$): 1.57(3H,s), 1.55 to 2.05(4H,m), 1.60(3H,s), 1.71(3H,s), 2.67(1H,d,15Hz), 2.75 to 2.95(3H,m), 3.51(3H,m), 4.10(1H,d,15Hz), 4.26(1H,dd,1Hz,11Hz), 4.45(3H,s), 5.23(1H,m), 5.52(1H,m), 6.95(2H,t,5Hz), 8.49(1H,d,5Hz).

EXAMPLE 35

2-(1,2-Epoxy-1,5-dimethyl-4-hexenyl)-3-methoxy-1-ethylthiomethyl-1,4-cyclohexanediol As in Example 21, from fumagillol (1.00 g), was obtained. 2-(1,2-epoxy-1,5-dimethyl-4-hexenyl)-3-methoxy-1-ethylthiomethyl-1,4-cyclohexanediol (991 mg: yield 81%) as a pale yellow product.

NMR spectrum (δ value; CDCl$_3$) 1.27(3H,t,7Hz), 1.46(3H,s), 1.50(1H,m), 1.67(3H,s), 1.74(3H,s), 1.60 to 1.90(3H,m), 2.05 to 2.55(3H,m), 2.61(2H,q,7Hz), 2.80 to 3.00(3H,m), 3.35(3H,s), 4.22(1H,m), 5.20(1H,m).

EXAMPLE 36

4-O-(Chloroacetylcarbamoyl)-2-(1,2-epoxy-1,5-dimethyl-4-hexenyl)-3-methoxy-1-ethylthiomethyl-1,4cyclohexanediol As in Example 12, from 2-(1,2-epoxy-1,5-dimethyl-4-hexenyl)-1-ethylthiomethyl-3-methoxy-1,4-cyclohexanediol (300 mg) was obtained 4-O-(chloroacetylcarbamoyl)-2-(1,2-epoxy-1,5-dimethyl-4-h-exenyl)-3-methoxy-1-ethylthiomethyl-1,4-cyclohexanediol (385 mg: yield 95%) as colorless powder.

NMR spectrum (δ value; CDCl$_3$): 1.29(3H,t,7Hz), 1.48(3H,s), 1.60(1H,m), 1.66(3H,s), 1.74(3H,s), 1.60 to 1.95(3H,m), 2.05 to 2.60(3H,m), 2.62(2H,q,7Hz), 2.84(1H,d,13Hz), 2.93(1H,m), 3.01(1H,d,13Hz), 3.32(3H,s), 3.35(1H,m), 4.52(2H,s), 5.19(1H,m), 5.44(1H,m).

EXAMPLE 37

2-(1,2-Epoxy-1,5-dimethyl-4-hexenyl)-3-methoxy-1-benzylthiomethyl-1,4-cyclohexanediol As in Example 21, from fumagillol (500 mg) was obtained 2-(1,2-epoxy-1,5-dimethyl-4-hexenyl)-3-methoxy-1-benzylthiomethyl-1,4-cyclohexanediol (652 mg: yield 90%) as a colorless oily product.

NMR spectrum (δ value; CDCl$_3$): 1.38(3H,s), 1.48(1H,m), 1.66(3H,s), 1.74(3H,s), 1.55 to 1.90(3H,m), 2.05 to 2.55(3H,m), 2.75 to 3.00(3H,m), 3.30(1H,m), 3.33(3H,s), 3.74(1H,d,12Hz), 3.80(1H,d,12Hz), 5.19(1H,m), 7.15 to 7.40(5H,m).

Elemental Analysis for C$_{23}$H$_{34}$O$_4$S.0.3$_2$O: Calcd. C:67.05%, H:8.45%, Found C:67.03%, H:8.54%.

EXAMPLE 38

4-O-(Chloroacetylcarbamoyl)-2-(1,2-epoxy-1,5-dimethyl-4-hexenyl)-3-methoxy-1-benzylthiomethyl-1,4cyclohexanediol As in Example 12, from 2-(1,2-epoxy-1,5-dimethyl-4-hexenyl)-1-benzylthiomethyl-3-methoxy-1,4cyclohexanediol (461 mg) was obtained 4-O-(chloroacetylcarbamoyl)-2-(1,2-epoxy-1,5-dimethyl-4-h-exenyl)-3-methoxy-1-benzylthiomethyl-1,4cyclohexanediol (544 mg: yield 91%) as colorless powder.

NMR spectrum (δ value; CDCl$_3$): 1.40(3H,s), 1.45 to 1.90(4H,m], 1.65(3H,s), 1.73(3H,s), 2.05 to 2.60(3H,m), 2.77(1H,d,13Hz), 2.88(1H,m), 2.93(1H,d,13Hz), 4.50(3H,s), 3.76(1H,d,13Hz), 3.80(1H,d,13Hz), 4.50(2H,s), 5.17(1H,m), 5.42(1H,m), 7.20 to 7.40(5H,m).

EXAMPLE 39

2-(1,2-Epoxy-1,5-dimethyl-4-hexenyl)-3-methoxy-1-allylthiomethyl-1,4-cyclohexanediol As in Example 21, from fumagillol (500 mg) was obtained 2-(1,2-epoxy-1,5-dimethyl-4-hexenyl)-3-methoxy-1-allylthiomethyl-1,4-cyclohexanediol (555 mg: yield 88%) as a colorless oily product.

NMR spectrum (δ value; CDCl$_3$): 1.45(3H,s), 1.52(1H,m), 1.66(3H,s), 1.74(3H,s), 1.60 to 1.95(3H,m), 2.05 to 2.55(3H,m), 2.83(2H,s), 2.95(1H,t,6Hz), 3.19(2H,d,7Hz), 3.30(1H,m), 3.34(3H,s), 4.22(1H,m), 5.05 to 5.25(3H,m), 5.57 to 5.92(1H,m).

Elemental Analysis for C$_{19}$H$_{22}$O$_4$S: Calcd. C:64.01%, H:9.05%, Found C:63.71%, H:9.23%

EXAMPLE 40

4-O-(Chloroacetylcarbamoyl)-2-(1,2-epoxy-1,5-dimethyl-4-hexenyl)-3-methoxy-1-allylthiomethyl-1,4-cyclohexanediol As in Example 12, from 2-(1,2-epoxy-1,5-dimethyl-4-hexenyl)-1-allylthiomethyl-3-methoxy-1,4cyclohexanediol (374 mg) was obtained 4-O-(chloroacetylcarbamoyl)-2-(1,2-epoxy-1,5-dimethyl-4-h-exenyl)-3-methoxy-1-allylthiomethyl-1,4-cyclohexanediol (441 mg: yield 88%) as colorless powder.

NMR spectrum (δ value; CDCl$_3$): 1.47(3H,s), 1.55 to 1.95(4H,m), 1.66(3H,s), 1.74(3H,s), 2.05 to 2.55(3H,m), 2.80(1H,d,13Hz), 2.91(1H,d,13Hz), 2.92(1H,m), 3.20(3H,d,7Hz), 3.32(3H,s), 3.35(1H,m), 4.51(2H,s), 5.10 to 5.25(3H,m), 5.44(1H,m), 5.72 to 7.93(1H,m).

EXAMPLE 41

4-O-(N-Chloroacetylcarbamoyl)-2-(1,2-epoxy-1,5-dimethyl-4-hexenyl)-3-methoxy-1-allylmethylsulfoniomethyl-1,4-cyclohexanediol bromide As in Example 13, from 4-O-(N-chloroacetylcarbamoyl)-2-(1,2-epoxy-1,5-dimethyl-4-hexenyl)-3-methoxy-1-methylthiomethyl-1,4-cyclohexanediol (120 mg) was obtained 4-O-(N-chloroacetylcarbamoyl)-2-(1,2-epoxy-1,5-dimethyl-4-hexenyl)-3-methoxy-1-allylmethylsulfoniomethyl-1,4-cyclohexanediol bromide (126 mg: yield 82%) as colorless powder.

NMR spectrum (δ value; CD$_3$OD): 1.35 to 1.50(6H,m), 1.69(3H,s), 1.75(3H,s), 1.60 to 2.60(7H,m), 2.90(1.5H,s), 3.02(1.5H,s), 2.95 to 3.70(6H,m), 4.18(2H,m), 4.44(1H,m), 5.15 to 6.15(5H,m).

EXAMPLE 42

4-O-Phenoxycarbonyl-2-(1,2-epoxy-1,5-dimethyl-4hexenyl)-3-methoxy-1-methylthionmethyl-1,4-cyclohexanediol In dichloromethane (2 ml) were dissolved 2-(1,2-epoxy-1,5-dimethyl-4-hexenyl)-3-methoxy-1-methylthiomethyl-1,4-cyclohexanediol (200 mg) and dimethylaminopyridine (115 mg). To the solution was added, under ice-cooling, phenyl chloroformate (95 μl ), and the mixture was stirred for 16 hours. The reaction mixture was diluted with ethyl acetate (70 ml), washed with a saturated aqueous solution of sodium hydrogencarbonate and a saturated aqueous saline solution, followed by drying over anhydrous magnesium sulfate. The solvent was distilled off under reduced pressure, and the residue was purified by means of a silica gel column chromatography (carrier 10 g, developing solvent: ethyl acetate - hexane=1:4) to afford 4-O-phenoxycarbonyl-2-(1,2-epoxy-1,5-dimethyl-4-hexenyl)-3-methoxy-1-methylthiomethyl-1,4-cyclohexanediol (222mg: yield 81%) as a colorless oily product.

NMR spectrum (δ value; CDCl$_3$): 1.48(3H,s), 1.67(3H,s), 1.74(3H,s), 1.65 to a.95(4H,m), 2.10 to 2.55(3H,m), 2.2)(3H,s), 2.87(1H,d,13Hz), 2.95(1H,t,7Hz), 2.96(1H,d,13Hz), 3.35(3H,s), 3.35(1H,m), 5.20(1H,m), 5.39(1H,m), 7.15 to 7.45(5H,m).

EXAMPLE 43

4-O-Phenoxycarbonyl-2-(1,2-epoxy-1,5-dimethyl-4-hexenyl)-3-methoxy-1-dimethylsulfoniomethyl-1,4-cyclohexanediol iodide As in Example 13, from 4-O-phenoxycarbonyl-2-(1,2-epoxy-1,5-dimethyl-4-hexenyl)-3-methoxy-1-methylthiomethyl-1,4-cyclohexanediol (145 mg) was obtained 4-O-phenoxycarbonyl-2-(1,2-epoxy-1,5-dimethyl-4-hexenyl)-3-methoxy-1-dimethylsulfoniomethyl-1,4-cyclohexanediol iodide (165 mg: yield 87%) as pale yellow powder.

NMR spectrum ($\delta$ value; $CD_3OD$): 1.49(3H,s), 1.69(3H,s), 1.76(3H,s), 1.65 to 2.05(4H,m), 2.10 to 2.60(3H,m), 3.01(3H,s), 2.99(3H,s), 3.07(3H,s), 3.13(1H,t,6Hz), 3.38(3H,s), 3.52(1H,dd,3Hz,12Hz), 3.67(1H,d,14Hz), 4.04(1H,14Hz), 4.86(2H,s), 5.26(1H,m), 7.12 to 7.47(5H,m).

EXAMPLE 44

4-O-Benzoyl-2-(1,2-epoxy-1,5-dimethyl-4-hexenyl)-3-methoxy-1-methylthiomethyl-1,4-cyclohexanediol As in Example 42, from 2-(1,2-epoxy-1,5-dimethyl-4-hexenyl)-3-methoxy-1-methylthiomethyl-1,4-cyclohexanediol (100 mg) was obtained 4-O-benzoyl-2-(1,2-epoxy-1,5-dimethyl-4-hexenyl)-3-methoxy-1-methylthiomethyl-1,4-cyclohexanediol (91 mg: yield 69as a colorless oily product.

NMR spectrum ($\delta$ value; $CDCl_3$): 1.50(3H,s), 1.66(3H,s), 1.73(3H,s), 1.60 to 2.60(7H,m), 2.24(3H,s), 2.85(1H,d,13Hz), 3.00(1H,t,6Hz), 3.09(1H,d,13Hz), 3.33(3H,s), 3.40(1H,m), 5.19(1H,m), 5.74(1H,m), 7.40 to 7.65(3H,m), 8.08(2H,m).

EXAMPLE 45

4-O-Tosyl-2-(1,2-epoxy-1,5-dimethyl-4-hexenyl)-3-methoxy-1-methylthiomethyl-1,4-cyclohexanediol As in Example 42, from 2-(1,2-epoxy-1,5-dimethyl-4-hexenyl)-3-methoxy-1-methylthiomethyl-1,4-cyclohexanediol (200 mg) was obtained 4-O-tosyl-2-(1,2-epoxy-1,5-dimethyl-4-hexenyl)-3-methoxy-1-methylthiomethyl-1,4-cyclohexanediol (57 mg: yield 19%) as a colorless oily product.

NMR spectrum ($\delta$ value; $CDCl_3$): 1.40(3H,s), 1.64(3H,s), 1.72(3H,s), 1.60 to 1.95(4H,m), 2.05 to 2.50(3H,m), 2.13(3H,s), 2.45(3H,m), 2.85(1H,d,13Hz), 2.86(1H,t,6Hz), 2.93(1H,d,13Hz), 3.06(3H,s), 3.20(1H,m), 5.02(1H,m), 5.16(1H,m), 7.34(2H,d,8Hz), 7.84(2H,d,8Hz).

EXAMPLE 46

4-O-Mesyl-2-(1,2-epoxy-1,5-dimethyl-4-hexenyl)-3-methoxy-1-iodomethyl-1,4-cyclohexanediol As in Example 42, from 2-(1,2-epoxy-1,5-dimethyl-4-hexenyl)-3-methoxy-1-iodomethyl-1,4-cyclohexanediol (300 mg) was obtained 4-O-mesyl-2-(1,2-epoxy-1,5-dimethyl-4-hexenyl)-3-methoxy-1-iodomethyl-1,4-cyclohexanediol (314 mg: yield 88%) as a colorless oily product.

NMR spectrum ($\delta$ value; $CDCl_3$) 1.51(3H,s), 1.60(1H,m), 1.66(3H,s), 1.74(3H,s), 1.80 to 2.55(6H,m), 2.95(1H,t,6Hz), 3.11(3H,s), 3.30(1H,m), 3.38(3H,s), 3.53(1H,d,11Hz), 3.56(1H,d,11Hz), 5.19(1H,m), 5.22(1H,m).

EXAMPLE 47

4-O-Mesyl-2-(1,2-epoxy-1,5-dimethyl-4-hexenyl)-3-methoxy-1-methylthiomethyl-1,4-cyclohexanediol As in Example 10, from 4-O-mesyl-2-(1,2-epoxy-1,5-dimethyl-4-hexenyl)-3-methoxy-1-methylthiomethyl-1,4-cyclohexanediol (179 mg) was obtained 4-O-mesyl-2-(1,2-epoxy-1,5-dimethyl-4-hexenyl)-3-methoxy-1-methylthiomethyl-1,4-cyclohexanediol (112 mg: yield 74%) as a colorless oily product.

NMR spectrum ($\delta$ value; $CDCl_3$): 1.46(3H,s), 1.67(3H,s), 1.74(3H,s), 1.65 to 2.55(7H,m), 2.20(3H,s), 2.91(3H,m), 3.11(3H,s), 3.34(1H,m), 3.38(3H,s), 5.h9(1H,m), 5.24(1H,m).

EXAMPLE 48

2-(1,2-Epoxy-1,5-dimethyl-4-hexenyl)-3-methoxy-1-(pyrrolidin-1-yl)methyl-1,4-cyclohexanediol N-oxide Fumagillol (500 mg) was dissolved in pyrrolidine (1 ml), and the solution was stirred at 50° C. overnight. Excess volume of pyrrolidine was distilled off under reduced pressure to leave 2-(1,2-epoxy-1,5-dimethyl-4-hexenyl)-3-methoxy-1-(pyrrolidin-1-yl)methyl-1,4-cyclohexanediol as a crude product. This crude product was dissolved in chloroform (5 ml), to which was added m-chloroperbenzoic acid (458 mg), and the mixture was stirred for 30 minutes. The solvent was distilled off under reduced pressure, and the residue was purified by means of a silica gel column chromatography (carrier 25 g, developing solvent: chloroform - methanol - ammoniacal water=15:1:0.1) to obtain 2-(1,2-epoxy-1,5-dimethyl-4-hexenyl)-3-methoxy-1-(pyrrolidin-1-yl)methyl-1,4-cyclohexanediol N-oxide (554 mg: yield 84%) as colorless powder.

NMR spectrum ($\delta$ value; $CDCl_3$): 1.43(1H,d,9Hz), 1.51(3H,s), 1.68(3H,s), 1.71(3H,s), 1.65 to 2.65(6H,m), 2.95(1H,d,13Hz), 3.15 to 3.55(4H,m), 3.48(3H,s), 3.88(3H,m), 4.28(1H,m), 5.24(1H,m).

$[\alpha]_D^{26} -20.5°$ (c 0.21,$CHCl_3$).

Elemental Analysis for $C_{20}H_{35}NO_5 \cdot H_2O$: Calcd. C:61.99%, H:9.62%, N:3.61%, Found C:62.02%, H:9.60%, N:3.60%.

EXAMPLE 49

4-O-Chloroacetylcarbamoyl-2-(1,2-epoxy-1,5-dimethyl-4-hexenyl)-3-methoxy-1-(pyrrolidin-1-yl)methyl-1,4-cyclohexanediol N-oxide As in Example 12, from 2-(1,2-epoxy-1,5-dimethyl-4-hexenyl)-3-methoxy-1-(pyrrolidin-1-yl)methyl-1,4-cyclohexanediol N-oxide (350 mg) was obtained 4-O-chloroacetylcarbamoyl-2-(1,2-epoxy-1,5-dimethyl-4-hex-enyl)-3-methoxy-1-pyrrolidin-1-yl)methyl-1,4-cyclohexanediol N-oxide (74 mg: yield 16%) as colorless powder.

NMR spectrum ($\delta$ value; $CDCl_3$): 1.47(3H,s), 1.20 to 2.80(11H,m), 1.68(3H,s), 1.72(3H,s), 3.20 to 410(7H,m), 3.42(3H,s), 4.49(2H,s), 5.22(1H,m), 5.48(1H,m).

$[\alpha]_D^{26} -41.0°$ (c 0.20, $CHCl_3$).

Elemental Analysis for $C_{23}H_{37}O_7Cl \cdot H_2O$: Calcd. C:54.49%, H:7.75%, Found C:54.17%, H:7.33%.

EXAMPLE 50

2-(1,2-Epoxy-1,5-dimethyl-4-hexenyl)-3-methoxy-(N-methylpyrrolidin-1-ylio)methyl-1,4-cyclohexanediol iodide Fumagillol (500 mg) was dissolved in pyrrolidine (1 ml), and the solution was stirred at 50° C. overnight. Excess volume of pyrrolidine was distilled off under reduced pressure to leave 2-(1,2-epoxy-1,5-dimethyl-4-hexenyl)-3-methoxy-1-(pyrrolidin-1-yl)methyl-1,4-cyclohexanediol as a crude product. This crude product was dissolved in dichloromethane (5 ml), to which was added methyl iodide (1.1 ml), and the mixture was stirred overnight. The solvent was distilled off under reduced pressure, and the residue was purified by means of a silica gel column chromatography (developing solvent: chloroform-methanol-ammoniacal water=0:1:0.1), followed by pulverizing with ether to obtain 2-(1,2-epoxy-1,5-dimethyl-4-hexenyl)-3-methoxy-1-(N-methylpyrrolidin-1-ylio)methyl-1,4-cyclohexanediol iodide (446 mg: yield 50%) as colorless powder.

NMR spectrum ($\delta$ value; $CD_3OD$): 1.45(3H,s), 1.68(3H,s), 1.75(3H,s), 1.65 to 2.60(11H,m), 3.05 to 3.45(2H,m), 3.23(3H,s), 3.34(3H,s), 3.55 to 3.90(4H,m), 3.62(1H,d,14Hz), 3.92(1H,d,14Hz), 4.25(1H,m), 5.25(1H,m).

EXAMPLE 51

4-O-Chloroacetylcarbamoyl-2-(1,2-epoxy-1,5-dimethyl-4-hexenyl)-3-methoxy-1-(N-methylpyrrolidin-1-ylio)-methyl-1,4-cyclohexanediol iodide As in Example 12, from 2-(1,2-epoxy-1,5-dimethyl-4-hexenyl)-3-methoxy-1-(N-methylpyrrolidin-1-ylio)-methyl-1,4-cyclohexanediol iodide (200 mg), was obtained 4-O-chloroacetylcarbamoyl-2-(1,2-epoxy-1,5-dimethyl-4-hexenyl)-3-methoxy-1-(N-methylpyrrolidin-1-ylio)methyl-1,4-cyclohexanediol iodide (76 mg: yield 0%) as colorless powder.

NMR spectrum ($\delta$ value; $CD_3OD$): 1.46(3H,s), 1.68(3H,s), 1.75(3H,s), 1.80 to 2.60(11H,m), 3.14(1H,t,6Hz), 3.25(3H,s), 3.34(3H,s), 3.46(1H,m), 3.60 to 3.90(4H,m), 3.69(1H,d,14Hz), 3.95(1H,d,14Hz), 3.46(2H,s), 5.24(1H,m), 5.46(1H,m).

EXAMPLE 52

4$\beta$-(Morpholino)carbonyloxy-2-(1,2-epoxy-1,5-dimethyl-4-hexenyl)-3-methoxy-1-methylthiomethyl cyclohexanol As in Example 10, from 4$\beta$-(morpholino)-carbonyloxy-6-epifumagillol (110 mg) was obtained 4$\beta$-O-(morpholino)carbonyl-2-(1,2-epoxy-1,5-dimethyl-4-hexen-yl)-3-methoxy-1-methylthiomethylcyclohexanol (81 mg: yield 64%) as a colorless oily product.

NMR spectrum ($\delta$ value; $CDCl_3$): 1.47(3H,s), 1.66(3H,s), 1.74(3H,s), 1.50 to 2.45(7H,m), 2.83(1H,d,13Hz), 2.94(1H,d,13Hz), 3.05(1H,t,6Hz), 3.35 to 3.80(8H,m), 4.69(1H,m), 5.22(1H,m).

EXAMPLE 53

4$\beta$-Hexylamino-2-(1,2-epoxy-1,5-dimethyl-4-hexenyl)-3-methoxy-1-methylthiomethylcyclohexanol As in Example 10, from 6$\beta$-hexylamino-6-desoxyfumagillol (110 mg) was obtained 4$\beta$-hexylamino-2-(1,2-epoxy-1,5-dimethyl-4-hexenyl)-3-methoxy-1-methylthiomethylcyclohexanol (110 mg: yield 88%) as a colorless oily product.

NMR spectrum ($\delta$ value; $CDCl_3$): 0.88(3H,m), 1.20 to 1.90(12H,m), 1.48(3H,s), 1.65(3H,s), 1.73(3H,s), 2.17(3H,s), 2.32(2H,m), 2.50(2H,m), 2.71(1H,m), 2.78(1H,d,13Hz), 2.91(1H,d,13Hz), 3.03(1H,m), 3.40(2H,m), 3.48(3H,s), 5.23(1H,m).

EXAMPLE 54

1-(4-Bromobenzyl)methylsulfoniomethyl-2-(1,2-epoxy-1,5-dimethyl-4-hexenyl)-3-methoxy-1,4-cyclohexanediol bromide In chloroform (0.5 ml) were dissolved 2-(1,2-epoxy-1,5-dimethyl-4-hexenyl)-3-methoxy-1-methylthiomethyl-1,4-cyclohexanediol (200 mg) and 4-bromobenzyl bromide (756 mg). To the solution was added silver bromide (11.4 mg), and the mixture was stirred for 28 hours. Insolubles were filtered off, and the solvent was distilled off. The residue was pulverized by the addition of ether. The resulting powder was dissolved in methanol (2 ml). Insolubles were filtered off, then the solvent was distilled off under reduced pressure. The residue was pulverized by the addition of ether to give 1-(4-bromobenzyl)methylsulfoniomethyl-2-(1,2-epoxy- 1,5-dimethyl-4-hexenyl)-3-methoxy-1,4cyclohexanediol bromide (176 mg: yield 50%) as colorless powder.

NMR spectrum ($\delta$ value; $CD_3OD$): 1.43(3H,s), 1.68(3H,s), 1.55 to 1.90(4H,m), 2.10 to 2.55(3H,m), 2.82(1.5,s), 3.10(1H,t,6Hz), 3.27(1H,m), 3.33(1.5H,s), 3.35(1.5H,s), 3.54(1H,m), 3.86 to 4.12(1H,m), 4.24(1H,m), 4.50 to 4.92(2H,m), 5.24(1H,h), 7.48(2H,m), 7.69(2H,m).

EXAMPLE 55

1-(4-Chlorobenzyl)methylsulfoniomethyl-2-(1,2-epoxy-1,5-dimethyl-4-hexenyl)-3-methoxy-1,4-cyclohexanediol bromide As in Example 54, 2-(1,2-epoxy-1,5-dimethyl-4-hexenyl)-3-methoxy-1-methylthiomethyl-1,4-cyclohexanediol (200 mg) was allowed to react with 4-chlorobenzyl bromide (1.24 g) to give 1-(4-chlorobenzyl)methylsulfoniomethyl-2-(1,2-epoxy-1,5-dimethyl-4-hexenyl)-3-methoxy-1,4-cyclohexanediol bromide (228 mg: yield 70%) as colorless powder.

NMR spectrum ($\delta$ value; $CD_3OD$): 1.43(3H,s), 1.68(3H,s), 1.75(3H,s), 1.55 to 1.90(4H,m), 2.10 to 2.55(3H,m), 2.82(1.5H,s), 2.99(1.5H,s), 3.09(1H,t,6Hz), 3.27(1H,m), 3.33(1.5H,s), 3.35(1.5H,s), 3.54(1H,m), 3.88 to 4.11(1H,m), 4.24(1H,m), 4.50(0.5H,d,18Hz), 4.71(1H,s), 4.91(0.5H,d,18Hz), 5.23(1H,m), 7.53(3H,m).

EXAMPLE 56

2-(1,2-epoxy-1,5-dimethyl-4-hexenyl)-1-(4-fluorobenzyl)methylsulfoniomethyl-3-methoxy-1,4cyclohexanediol bromide As in Example 54, 2-(1,2-epoxy-1,5-dimethyl-4-hexenyl)-3-methoxy-1-methylthiomethyl-1,4-cyclohexanedeiol (200 mg) was allowed to react with 4fluorobenzyl bromide (1.14 g) to give 2-(1,2-epoxy-1,5-dimethyl- 4-hexenyl)-1-(4-fluorobenzyl)methylsulfoniomethyl-3-methoxy-1,4-cyclohexanediol bromide (223 mg: yield 71%) as colorless powder.

NMR spectrum ($\delta$ value; $CD_3OD$): 1.43(3H,s), 1.68(3H,s), 1.74(3H,s), 1.55 to 1.90(4H,m), 2.10 to 2.55(3H,m), 2.80(1.5H,s), 2.98(1.5H,s), 3.10(1H,t,6Hz), 3.25(1H,m), 3.33(1.5H,s), 3.35(1.5H,s), 3.53(1H,m), 3.85 to 4.12(1H,m), 4.24(1H,m), 4.60(0.5H,d,17Hz), 4.71(1H,s), 4.92(0.5H,d,17Hz), 5.23(1H,m), 7.25(2H,m), 7.59(2H,m).

EXAMPLE 57

2-(1,2-Epoxy-1,5-dimethyl-4-hexenyl)-3-methoxy-1-(4-methylbenzyl)methylsulfoniomethyl-1,4-cclohexanediol bromide As in Example 54, 2-(1,2-epoxy-1,5-dimethyl-4-hexenyl)-3-methoxy-1-methylthiomethyl-1,4-cyclohexanediol (200 mg) was allowed to react with 4-methylbenzyl bromide (1.12 g) to give 2-(1,2-epoxy-1,5-dimethyl-4-hexenyl)-3-methoxy-1-(4-methylbenzyl)methylsulfoniomethyl-1,4-cyclohexanediol bromide (198 mg: yield 56%) as colorless powder.

NMR spectrum (δ value; CD$_3$OD): 1.42(1,5H,s), 1.44(1.5H,s),1.68(3H,s), 1.74(3H,s), 1.55 to 1.90(4H,m), 2.39(3H,s), 2.10 to 2.55(3H,m), 2.75(1.5H,s), 2.94(1.5H,s), 3.08(1H,t,6Hz), 3.27(1H,m), 3.33(1.5H,s), 3.35(1.5H,s), 3.49(1H,d,12Hz), 3.80 to 4.10(1H,m), 4.24(1H,m), 4.61(0.5H,d,13Hz), 4.66(1H,s), 4.87(0.5H,d,13Hz), 5.23(1H,m), 7.37(4H,m).

EXAMPLE 58

1-(3-Bromobenzyl)methylsulfoniomethyl-2-(1,2-epoxy-1,5-dimethyl-4-hexenyl)-3-methoxy-1,4-cyclohexanediol bromide As in Example 54, 2-(1,2-epoxy-1,5-dimethyl-4-hexenyl)-3-methoxy-1-methylthiomethyl-1,4-cyclohexanediol (200 mg) was allowed to react with 3-bromobenzyl bromide (1.51 g) to give 1-(3-bromobenzyl)methylsulfoniomethyl-2-(1,2-epoxy-1,5-dimethyl-4-hexenyl)-3-methoxy-1,4-cyclohexanediol bromide (184 mg: yield 52%) as colorless powder.

NMR spectrum (δ value; CD$_3$OD): 1.44(3H,s), 1.68(3H,s), 1.74(3H,s), 1.55 to 1.90(4H,m), 2.10 to 2.55(3H,m), 2.83(1.5H,s), 3.10(1H,t,6Hz), 3.25(1H,m), 4.12(1H,m), 4.24(1H,m), 4.60(0.5H,d,17Hz), 4.69(1H,s), 4.83(0.5H,d,17Hz), 5.23(1H,m), 7.35 to 7.85(4H,m).

EXAMPLE 59

1-(2-Bromobenzyl)methylsulfoniomethyl-2-(1,2-epoxy-1,5-dimethy-4-hexenyl)-3-methoxy-1,4-cyclohexanediol bromide As in Example 54, 2-(1,2-epoxy-1,5-dimethyl-4-hexenyl)-3-methoxy-1-methylthiomethyl-1,4-cyclohexanediol (200 mg) was allowed to react with 2-bromobenzyl bromide (1.51 g) to give 1-(2-bromobenzyl)methylsulfoniomethyl-2-(1,2-epoxy-1,5-dimethyl-4-hexenyl)-3-methoxy-1,4-cyclohexanediol bromide (29 mg: yield 8%) as colorless powder.

NMR spectrum (δ value; CD$_3$OD): 1.46(3H,s), 1.69(3H,s), 1.75(3H,s), 1.55 to 1.95(4H,m), 2.10 to 2.55(3H,m), 2.90(1.5H,s), 3.08(1.5H,s), 3.11(1H,t,6Hz), 3.25(1H,m), 3.31(1.5H,s), 3.35(1.5H,s), 3.63 to 4.05(2H,m), 4.24(1H,m), 4.66(1H,s), 4.78(0.5H,d,13Hz), 5.18(0.5H,d,13Hz), 5.23(1H,m), 7.15 to 7.83(4H,m).

EXAMPLE 60

1-(4-Bromobenzyl)methylsulfoniomethyl-4-(N-chloroacetylcarbamoyloxy)-2-(1,2-epoxy-1,5-dimethyl-4-hexenyl)-3-methoxycyclohexanol bromide To a solution of 1-(2-bromobenzyl)methylsulfoniomethyl-2-(1,2-epoxy-1,5-dimethyl-4-hexenyl)-3-methoxy- 1,4-cyclohexanediol bromide (150 mg) in dichloromethane (2 ml) was added dropwise, under ice-cooling, chloroacetylisocyanate (40 ml), then the mixture was stirred for 30 minutes. To the reaction mixture was added water to suspend the reaction. The product was extracted with ethyl acetate. The organic layer was washed with a saturated aqueous saline solution, followed by drying over anhydrous magnesium sulfate. The solvent was distilled off under reduced pressure. The residue was purified by means of a silica gel column chromatography (carrier 10 g, developing solvent : chloroform-methanol=20:1) to give 1-(4-bromobenzyl)methylsulfoniomethyl-4-(N-chloroacetylcarbamoyloxy)-2-(1,2-epoxy-1,5-dimethyl-4-hexenyl)-3-methoxycyclohexanol bromide (80 mg: yield 44%).

NMR spectrum (δ value; CD$_3$OD): 1.43(3H,s), 1.68(3H,s), 1.74(3H,s), 1.50 to 2.00(4H,m), 2.10 to 2.55(3H,m), 2.86(1.5H,s), 3.01(1.5H,s), 3.10(1H,t,6Hz), 3.34(1.5H,s), 3.37(1.5H,s), 3.45(1H,m), 3.57(1H,m), 3.90 to 4.15(1H,m), 4.43(2H,s), 4.60(0.5H,d,13Hz), 4.73(1H,s), 4.91(0.5H,d,13Hz), 5.23(1H,m), 5.45(1H,m), 7.49(2H,m), 7.69(2H,m).

$[\alpha]_D^{26} -43.5°$ (c 0.20, CHCl$_3$).

EXAMPLE 61

4-(N-Chloroacetylcarbamoyloxy)-1-(4-chlorobenzyl)-methylsulfoniomethyl-2-(1,2-epoxy-1,5-dimethyl-4-hexenyl)-3-methoxycyclohexanol bromide As in Example 60, from 1-(4-chlorobenzyl)methylsulfoniomethyl-2-(1,2-epoxy-1,5-dimethyl-4-hexenyl)-3-methoxy-1,4-cyclohexanediol (183 mg) was obtained 4-(N-chloroacetylcarbamoyloxy)-1-(4-chlorobenzyl)-methylsulfoniomethyl-2-(1,2-epoxy-1,5-dimethyl-4-hexenyl)-3-methoxycyclohexanol bromide (123 mg: yield 55%) as colorless powder.

NMR spectrum (δ value; CD$_3$OD): 1.43(3H,s), 1.68(3H,s), 1.74(3H,s), 1.60 to 1.95(4H,m), 2.10 to 2.55(3H,m), 2.85(1.5H,s), 3.01(1.5H,s), 3.09(1H,t,6Hz), 3.33(1.5H,s), 3.34(1.5H,s), 3.45(1H,m), 3.58(1H,m), 3.90 to 4.18(1H,m), 4.43(1H,m), 4.44(1H,s), 4.66 to 4.98(2H,m), 5.23(1H,m), 5.46(1H,m), 7.55(4H,m).

$[\alpha]_D^{24} -45.2°$ (c 0.22, CHCl$_3$).

EXAMPLE 62

4-(N-Chloroacetylcarbamoyloxy)-2-(1,2-epoxy-1,5-dimethyl-4-hexenyl)-1-(4-fluorobenzyl)methylsulfoniomethyl-3-methoxycyclohexanol bromide As in Example 60, from 2-(1,2-epoxy-1,5-dimethyl-4-hexenyl)-1-(4-fluorobenzyl)methyl-sulfoniomethyl-3-methoxy-1,4-cyclohexanediol (181 mg) was obtained 4-(N-chloroacetylcarbamoyloxy)-2-(1,2-epoxy-1,5-dimethyl-4-hexenyl-1-(4-fluorobenzyl)-methylsulfoniomethyl-3-methoxycyclohexanol bromide (118 mg: yield 52%) as colorless powder.

NMR spectrum (δ value; CD$_3$OD): 1.43(3H,s), 1.68(3H,s), 1.74(3H,s), 1.50 to 1.95(4H,m), 2.10 to 2.55(3H,m), 2.84(1.5H,s), 3.00(1.5H,s), 3.10(1H,t,6 Hz), 3.33(1.5H,s), 3.35(1.5H,s), 3.45(1.5H,m), 3.58(1H,m), 3.90 to 4.18(1H,m), 4.43(1H,m), 4.44(1H,s), 4.70(0.5H,d,13 Hz), 4.87(1H,s), 4.99(0.5H,d,13 Hz), 5.23(1H,m), 5.46(1H,m), 7.26(2H,m), 7.61(2H,m).

$[\alpha]_D^{24} -53.3°$ (c 0.22, CHCl$_3$).

EXAMPLE 63

4-(N-Chloroacetylcarbamoyloxy)-2-(1,2-epoxy-1,5-dimethyl-4-hexenyl-3-methoxy-1-(4-methylbenzyl)methylsulfoniomethylcyclohexanol bromide As in Example 60, from 2-(1,2-epoxy-1,5-dimethyl-4-hexenyl)-3-methoxy-1-(4-methylbenzyl)methylsulfoniomethyl-1,4-cyclohexanediol (165 mg) was obtained 4-(N-chloroacetylcarbamoyloxy)-2-(1,2-epoxy-1,5-dimethyl-4-hexenyl)-3-methoxy-1-(4-methylbenzyl)methylsulfoniomethylcyclohexanol bromide (107 mg: yield 52%) as colorless powder.

NMR spectrum ($\delta$ value; $CD_3OD$): 1.42(1.5H,s), 1.43(1.5H,s), 1.68(3H,s), 1.74(3H,s), 1.50 to 1.95(4H,m), 2.39(3H,s), 2.10 to 2.55(3H,m), 2.79(1.5H,s), 2.97(1.5H,s), 3.09(1H,t,6 Hz), 3.32(1.5H,s), 3.35(1.5H,s), 3.45(1H,m), 3.52(1H,m), 3.85 to 4.15(1H,m), 4.43(1H,m), 4.44(1H,s), 4.63(0.5H,d,13 Hz), 4.69(1H,s), 4.92(0.5H,d,13 Hz), 5.22(1H,m), 5.46(1H,m), 7.33(3H,m), 7.43(2H,m). $[\alpha]_D^{24} -46.4°$ (c 0.22, $CHCl_3$).

EXAMPLE 64

1-(3-Bromobenzyl)methylsulfoniomethyl-4-(N-chloroacetylcarbamoyloxy)-2-(1,2-epoxy-1,5-dimethyl-4-hexenyl)-3-methoxycyclohexanol bromide As in Example 60, from 2-(1,2-epoxy-1,5-dimethyl-4-hexenyl)-3-methoxy-1-(4-methylbenzyl)-methylsulfoniomethyl-1,4-cyclohexanediol (222 mg) was obtained 1-(3-bromobenzyl)methylsulfoniomethyl-4-(N-chloroacetylcarbamoyloxy)-2-(1,2-epoxy-1,5-dimethyl-4-hexenyl)-3-methoxycyclohexanol bromide (171 mg: yield 64%) as colorless powder.

NMR spectrum ($\delta$ value; $CD_3OD$): 1.43(3H,s), 1.68(3H,s), 1.73(3H,s), 1.50 to 1.95(4H,m), 2.10 to 2.60(3H,m), 2.87(1.5H,s), 3.01(1.5H,s), 3.11(1H,t,6 Hz), 3.32(1.5H,s), 3.34(1.5H,s), 3.45(1H,m), 3.57(1H,m), 3.90 to 4.15(1H,m), 4.64(0.5H,d,10 Hz), 4.73(1H,s), 4.92(0.5H,d,10 Hz), 5.22(1H,m), 5.46(1H,m), 7.35 to 7.90(4H,m).

$[\alpha]_D^{24} -38.3°$ (c 0.20, $CHCl_3$).

EXAMPLE 65

Separation of stereoisomers of 1-(3-bromobenzyl)methylsulfoniomethyl-4-(N-chloroacetylcarbamoyloxy)-2-(1,2-epoxy-1,5-dimethyl-4-hexenyl)-3-methoxycyclohexanol bromide By subjecting 1-(3-bromobenzyl)methylsulfoniomethyl-4-(N-chloroacetylcarbamoyloxy)-2-(1,2-epoxy-1,5-dimethyl-4-hexenyl)-3-methoxycyclohexanol bromide (150 mg) obtained in substantially the same manner as Example 64 to a silica gel column chromatography (carrier 10 g, developing solvent: dichloromethanemethanol-water=20:1:0.2), a steroisomer showing relatively high Rf value in TLC (developing solvent:-chloroform-methanol=20:1) (isomer A:60 mg) was successfully separated from a stereoisomer showing relatively low RF value in the same TLC (isomer B:62 mg), the respective isomers being as colorless powder.

Isomer A:

NMR spectrum ($\delta$ value; $CD_3OD$): 1.43(3H,s), 1.67(3H,s), 1.73(3H,s), 1.50 to 1.95(4H,m), 2.10 to 2.55(3H,m), 3.01(3H,s), 3.11(1H,m), 3.32(3H,s), 3.43(1H,m), 3.54(1H,d,13 Hz), 3.98(1H,d,13 Hz), 4.42(2H,s), 4.72(2H,s), 5.21(1H,m), 5.44(1H,m), 7.40 to 7.89(4H,m).

Isomer B:

NMR spectrum ($\delta$ value; $CD_3OD$): 1.43(3H,s), 1.68(3H,s), 1.74(3H,s), 1.50 to 1.95(4H,m), 2.10 to 2.60(3H,m), 2.86(3H,s), 3.11(1H,m), 3.34(3H,s), 3.43(1H,m), 3.53(1H,d,14 Hz), 4.12(1H,d,14 Hz), 4.43(2H,s), 4.69(1H,d,13 Hz), 4.73(1H,d,21 Hz), 4.91(1H,d,13 Hz), 5.01(1H,d,21 Hz), 5.22(1H,m), 5.47(1H,m), 7.40 to 7.90(4H,m).

EXAMPLE 66

1-Diallylsulfoniomethyl-2-(1,2-epoxy-1,5-dimethyl-4-hexenyl)-3-methoxy-1,4-cyclohexanediol perchlorate To a mixture of 1-allylthiomethyl-2-(1,2-epoxy-1,5-dimethyl-4-hexenyl)-3-methoxy-1,4-cyclohexanediol (300 mg) and allyl bromide (0.73 ml) was added silver perchlorate (192 mg) under ice-cooling, which was stirred for 30 minutes at room temperature. Insolubles were filtered off, and the solvent was distilled off under reduced pressure. The residue was purified by means of a silica gel column chromatography (carrier 30 g, developing solvent : chloroform-methanol=20:1) to give 1-diallylsulfoniomethyl-2-(1,2-epoxy-1,5-dimethyl-4-hexenyl)-3-methoxy-1,4-cyclohexanediol perchlorate (160 mg: yield 37%) as colorless powder.

NMR spectrum ($\delta$ value; $CD_3OD$): 1.45(3H,s), 1.68(3H,s), 1.75(3H,s), 1.60 to 2.60(7H,m), 3.11(1H,t,6 Hz), 3.29(1H,m), 3.34(3H,s), 3.90 to 4.35(7H,m), 5.25(1H,m), 5.55 to 6.15(6H,m).

EXAMPLE 67

1-Diallylsulfoniomethyl-4-(N-chloroacetylcarbamoyloxy)-2-(1,2-epoxy-1,5-dimethyl-4-hexenyl)-3-methoxycyclohexanol perchloroate To a solution of 1-diallylsulfoniomethyl-2-(1,2-epoxy-1,5-dimethyl-4-hexenyl)-3-methoxy-1,4-cyclohexanediol perchlorate (143 mg) in dichloromethane (2 ml) was added dropwise, which was stirred for 30 minutes. To the reaction mixture was added water to suspend the reaction, which was subjected to extraction with ethyl acetate. The organic layer was washed with a saturated aqueous saline solution and dried over anhydrous magnesium sulfate. The solvent was distilled off under reduced pressure. The residue was purified by means of a silica gel column chromatography (carrier 15 g, developing solvent: chloroform-methanol=20:1) to give 1-diallylsulfoniomethyl-4-(N-chloroacetylcarbamoyloxy)-2-(1,2-epoxy-1,5-dimethyl-4-hexenyl)-3-methoxycyclohexanol perchlorate (100 mg: yield 56%).

NMR spectrum ($\delta$ value; $CD_3OD$): 1.45(3H,s), 1.69(3H,s), 1.75(3H,s), 1.55 to 2.60(7H,m), 3.11(1H,m), 3.34(3H,s), 3.45(1H,m), 3.90 to 4.40(6H,m), 4.43(2H,s), 5.25(1H,m), 5.47(1H,m), 5.55 to 6.20(6H,m).

$[\alpha]_D^{24} -10.7°$ (c 0.21, $CHCl_3$).

Elemental Analysis for $C_{25}H_{39}NO_{10}SCl_2$: Calcd. C:48.70%, H:6.38%, N:2.27%, Found C:48.46%, H:6.67%, N:2.03%.

EXAMPLE 68

1-Dibenzylsulfoniomethyl-2-(1,2-epoxy-1,5-dimethyl-4-hexenyl)-3-methoxy-1,4-cyclohexanediol perchlorate As in Example 66, from 1-benzylthiomethyl-2-(1,2-epoxy-1,5-dimethyl-4-hexenyl)-3-methoxy-1,4-cyclohexanediol (300 mg) was obtained 1-dibenzylsulfoniomethyl-2-(1,2-epoxy-1,5-dimethyl-4-hexenyl)-3-methoxy-1,4-cyclohexanediol perchlorate (145 mg: yield 33%) as colorless powder.

NMR spectrum (δ value; CD₃OD): 1.41(3H,s), 1.69(3H,s), 1.75(3H,s), 1.45 to 2.60(7H,m), 3.13(1H,m), 3.22(2H,m), 3.31(3H,s), 4.15(2H,m), 4.47(1H,d,13 Hz), 4.71(1H,d,13 Hz), 4.76(1H,d,13 Hz), 4.98(1H,d,13 Hz), 5.23(1H,m), 7.47(10H,m).

EXAMPLE 69

1-Dibenzylsulfoniomethyl-4-(N-chloromethylcarbamoyloxy)-2-(1,2-epoxy-1,5-dimethyl-4-hexenyl)-3-methoxycyclohexanol perchlorate As in Example 67, from 1-dibenzylsulfonio-methyl-2-(1,2-epoxy-1,5-dimethyl-4-hexenyl)-3-methoxy-1,4-cyclohexanediol perchlorate (120 mg) was obtained 1-dibenzylsulfoniomethyl-4-(N-chloromethylcarbamoyloxy)-2-(1,2-epoxy-1,5-dimethyl-4-hexenyl)-3-methoxycyclohexanol perchlorate (100 mg: yield 69%) as colorless powder.

NMR spectrum (δ value; CD₃OD): 1.41(3H,s), 1.69(3H,s), 1.74(3H,s), 1.55 to 1.90(4H,m), 2.10 to 2.60(3H,m), 3.04(1H,t,6 Hz), 3.30(3H,s), 3.36(2H,m), 4.15(1H,d,12 Hz), 4.41(2H,s), 4.55(1H,d,13 Hz), 4.74(1H,d,13 Hz), 4.80(1H,d,13 Hz), 4.98(1H,d,13 Hz), 5.22(1H,m), 5.36(1H,m), 7.48(10H,m).

$[α]_D^{23} - 36.4°$ (c 0.20, CHCl₃)

Elemental Analysis for C₃₃H₄₃NO₁₀SCl₃: Calcd. C:55.31%, H:6.05%, N:1.95%, Found C:55.66%, H:6.17%, N:2.12%.

EXAMPLE 70

4-Carbamoyloxy-2-(1,2-epoxy-1,5-dimethyl-4-hexenyl)-3-methoxy-1-dimethylsulfoniomethyl-cyclohexanol iodide As in Example 13, from 4-O-carbamoyl-2-(1,2-epoxy-1,5-dimethyl-4-hexenyl)-3-methoxy-1-methyl-thiomethyl-1,4-cyclohexanediol (240 mg) was obtained 4-carbamoyloxy-2-(1,2-epoxy-1,5-dimethyl-4-hexenyl)-3-methoxy-1-dimethylsulfoniomethyl-cyclohexanol iodide (282 mg: yield 85%) as colorless powder.

NMR spectrum (δ value; CD₃OD): 1.46(3H,s), 1.69(3H,s), 1.75(3H,s), 1.65 to 1.90(4H,m), 2.10 to 2.60(3H,m), 3.00(3H,s), 3.06(3H,s), 3.10(1H,t,6 Hz), 3.34(3H,s), 3.41(1H,m), 3.73(1H,d,13 Hz), 4.04(1H,d,13 Hz), 5.25(2H,m).

$[α]_D^{26} - 43.3°$ (c 0.21, CHCl₃).

Elemental Analysis for C₁₉H₃₄NO₅SI: Calcd. C:44.27%, H:6.65%, N:2.72%, Found C:44.58%, H:6.87%, N:2.77%.

EXAMPLE 71

1-Benzylmethylsulfoniomethyl-4-carbamoyloxy-2-(1,2-epoxy-1,5-dimethyl-4-hexenyl)-3-methoxycyclohexanol bromide As in Example 13, from 4-O-carbamoyl-2-(1,2-epoxy-1,5-dimethyl-4-hexenyl)-3-methoxy-1-methyl-thiomethyl-1,4-cyclohexanediol (200 mg) was obtained 1-benzylmethylsulfoniomethyl-4-carbamoyloxy-2-(1,2-epoxy-1,5-dimethyl-4-hexenyl)-3-methoxycyclohexanol bromide (240 mg: yield 82%) as colorless powder.

NMR spectrum (δ value; CD₃OD): 1.43(1.5H,s), 1.44(1.5H,s), 1.68(3H,s), 1.74(3H,s), 1.50 to 1.90(4H,m), 2.10 to 2.60(3H,m), 2.81(1.5H,s), 2.98(1.5H,s), 3.08(1H,t,6 Hz), 3.31(1.5H,s), 3.33(1.5H,s), 3.40(1H,m), 3.57(0.5H,d,13 Hz), 3.59(0.5H,d,13 Hz), 4.67(0.5H,d,13 Hz), 4.74(1H,s), 4.95(0.5H,d,13 Hz), 5.23(2H,m).

$[α]_D^{23} - 36.4°$ (c 0.20, CHCl₃).

Elemental Analysis for C₂₅H₃₈NO₅SBr: Calcd. C:55.14%, H:7.03%, N:2.57%, Found C:55.16%, H:7.32%, N:2.63%.

EXAMPLE 72

4-(2-Chloroethylcarbamoyloxy)-2-(1,2-epoxy-1,5-dimethyl-4-hexenyl)-3-methoxy-1-methylthiomethylcyclohexanol To a solution of 2-(1,2-epoxy-1,5-dimethyl-4-hexenyl)-1-methylthiomethyl-1,4-cyclohexanediol (1.00 g) and dimethylaminopyridine (185 ml) in dichloromethane (10 ml) was added dropwise 2-chloroethylisocyanate (0.52 ml), which was stirred overnight. To the reaction mixture was added water to suspend the reaction, then the product was extracted with ethyl acetate. The organic layer was washed with a saturated aqueous saline solution, followed by drying over anhydrous magnesium sulfate. The solvent was distilled off under reduced pressure, then the residue was purified by means of a silica gel column chromatography (carrier 50 g, developing solvent:ethyl acetate - hexane = 1:4) to give 4-(2-chloroethylcarbamoyloxy)-2-(1,2-epoxy-1,5-dimethyl-4-hexenyl)-3-methoxy-1-methylthiomethylcyclohexanol (912 mg: yield 69%) as colorless powder.

NMR spectrum (δ value; CDCl₃): 1.47(3H,s), 1.66(3H,s), 1.74(3H,s), 1.55 to 1.90(4H,m), 2.20(3H,s), 2.05 to 2.60(3H,m), 2.95(3H,m), 3.30(1H,m), 3.32(3H,s), 3.45 to 3.70(4H,m), 5.20(2H,m).

EXAMPLE 73

4-(2-Chloroethylcarbamoyloxy)-2-(1,2-epoxy-1,5-dimethyl-4-hexenyl)-3-methoxy-1-dimethylsulfoniomethylcyclohexanol iodide As in Example 13, from 4-(2-chloroethylcarbamoyloxy)-2-(1,2-epoxy-1,5-dimethyl-4-hexenyl)-3-methoxy-1-methylthiomethylcyclohexanol (150 mg) was obtained 4-(2-chloroethylcarbamoyloxy)-2-(1,2-epoxy-1,5-dimethyl-4-hexenyl)-3-methoxy-1-dimethylsulfoniomethylcyclohexanol iodide (140 mg: yield 70%) as colorless powder.

NMR spectrum (δ value; CD₃OD): 1.46(3H,s), 1.69(3H,s), 1.75(3H,s), 1.65 to 1.90(4H,m), 2.10 to 2.60(3H,s), 2.99(3H,s), 3.06(3H,s), 3.10(1H,m), 3.33(3H,s), 3.35 to 3.65(5H,m), 3.71(1H,d,14 Hz), 4.04(1H,d,14 Hz), 5.25(1H,m), 5.31(1H,m).

EXAMPLE 74

1-Benzylmethylsulfoniomethyl-4-chloroacetylcarbamoyloxy-2-(1,2-epoxy-1,5-dimethyl-4-hexenyl)-3-methoxycyclohexanol tetrafluoroborate In dichloromethane (1 ml) were dissolved 1-benzylthiomethyl-4-chloroacetylcarbamoyloxy-2-(1,2-epoxy-1,5-dimethyl-4-hexenyl)-3-methoxy-1,4-cyclohexanediol (200 mg) and methyl iodide (0.24 ml). To the solution was added silver tetrafluoroborate, and the mixture was stirred for 8 hours at room temperature. Insolubles were filtered off, and the solvent was distilled off under reduced pressure. The residue was pulverized with ether to give 1-benzylmethylsulfoniomethyl-4-chloroacetylcarbamoyloxy-2-(1,2-epoxy-1,5-dimethyl-4-hexenyl)-3-methoxycyclohexanol tetrafluoroborate (73 mg: yield 30%) as colorless powder.

NMR spectrum (δ value; CD₃OD): 1.41)1.5H,s), 1.42(1.5H,s), (1.68(1.5H,s), 1.75(3H,s), 1.60 to 2.60(7H,m), 2.80(1.5H,s), 3.00(1.5H,s), 3.11(1H,t,6 Hz), 3.32(1.5H,s), 3.34(1.5H,s), 3.45(2H,m), 2.90 to 4.15(1H,m), 4.42(1H,s), 4.43(1H,s), 4.66(0.5H,d,13 Hz), 4.70(1H,s), 4.94(0.5H,d,13 Hz), 5.22(1H,m), 5.45(1H,m).
$[\alpha]_D^{23} -23.3°$ (c 0.21, CHCl$_3$).

EXAMPLE 75

1-Benzylmethylsulfoniomethyl-4-chloroacetylcarbamoyloxy-2-(1,2-epoxy-1,5-dimethyl-4-hexenyl)-3-methoxycyclohexanol tosylate Silver oxide (37 mg) was suspended in acetonitrile (1 ml), to which was added p-toluenesulfonic acid . monohydrate (61 ml), and the mixture was stirred for 5 minutes. To the resultant was then added 1-benzylmethylsulfoniomethyl-4-chloroacetylcarbamoyloxy-2-(1,2-epoxy-1,5-dimethyl-4-hexenyl)-3-methoxycyclohexanol bromide (200 mg). The mixture was stirred for further 30 minutes, then insolubles were filtered off. The solvent was distilled off under reduced pressure. The residue was purified by means of a silica gel column chromatography (carrier 4 g, developing solvent : chloroform-methanol=20:1) to give 1-benzylmethylsulfoniomethyl-4-chloroacetylcarbamoyloxy-2-(1,2-epoxy-1,5-dimethyl-4-hexenyl)-3-methoxycyclohexanol tosylate (67 mg: yield 29%) as colorless powder.

NMR spectrum (δ value; CD$_3$OD): 1.41(1,5H,s), 1.42(1.5H,s), 1.68(1.5H,s), 1.75(3H,s), 2.37(3H,s), 1.60 to 2.60(7H,m), 2.80(1.5H,s), 3.00(1.5H,s), 3.11(1H,t,6 Hz), 3.32(1.5H,s), 3.34(1.5H,s), 3.45(2H,m), 3.90 to 4.15(1H,m), 4.42(1H,s), 4.43(1H,s), 4.66(0.5H,d,13 Hz), 4.70(1H,s), 4.94(0.5H,d,13 Hz), 5.22(1H,m), 5.45(1H,m), 7.23(2H,d,8 Hz), 7.72(2H,d,8 Hz).

EXAMPLE 76

1-Benzylmethylsulfoniomethyl-4-chloroacetylcarbamoyloxy-2-(1,2-epoxy-1,5-dimethyl-4-hexenyl)-3-methoxycyclohexanol hydrogen L-tartrate As in Example 75, from 1-benzylmethylsulfoniomethyl-4-chloroacetylcarbamoyloxy-2-(1,2-epoxy-1,5-dimethyl-4-hexenyl)-3-methoxycyclohexanol bromide (200 mg) was obtained 1-benzylmethylsulfoniomethyl-4-chloroacetylcarbamoyloxy-2-(1,2-epoxy-1,5-dimethyl-4-hexenyl)-3-methoxycyclohexanol hydrogen L-tartrate (126 mg: yield 56%) as colorless powder.

NMR spectrum (δ value; CD$_3$OD): 1.42(1,5H,s), 1.43(1.5H,s), 1.67(1.5H,s), 1.74(3H,s), 1.60 to 2.60(7H,m), 2.81(1.5H,s), 3.00(1.5H,s), 3.11(1H,t,6 Hz), 3.33(15H,s), 3.35(1.5H,s), 3.45(2H,m), 3.90 to 4.15(1H,s), 4.41(2H,s), 4.43(1H,s), 4.44(1H,s), 4.66(0.5H,d,13 Hz), 4.70(1H,s), 4.94(0.5H,d,13 Hz), 5.22(1H,m), 5.45(1H,m).
$[\alpha]_D^{24} -28.4°$ (c 0.20, CHCl$_3$).

Elemental Analysis for C$_{31}$H$_{44}$NO$_{12}$SCl.1.5H$_2$O Calcd. C:51.91%, H:6.61%, N:1.95%, Found C:51.91%, H:6.70%, N:1.99%.

EXAMPLE 77

1-Benzylmethylsulfoniomethyl-4-chloroacetylcarbamoyloxy-2-(1,2-epoxy-1,5-dimethyl-4-hexenyl)-3-methoxycyclohexanol hydrogen succinate As in Example 75, from 1-benzylmethylsulfoniomethyl-4-Chloroacetylcarbamoyloxy-2-(1,2-epoxy-1,5-dimethyl-4-hexenyl)-3-methoxycyclohexanol bromide (200 mg) was obtained 1-benzylmethylsulfoniomethyl-4-chloroacetylcarbamoyloxy-2-(1,2-epoxy-1,5-dimethyl-4-hexenyl)-3-methoxycyclohexanol hydrogen succinate (102 mg: yield 48%) as colorless powder.

NMR spectrum (δ value: CD$_3$OD): 1.42(1.5H,s), 1.43(1.5H,s), 1.68(1.5H,s), 1.74(3H,s), 2.51(4H,s), 1.60 to 2.60(7H,m), 2.80(1.5H,s), 3.00(1.5H,s), 3.11(1H,t,6 Hz), 3.32(1.5H,s), 3.34(1.5H,s), 3.45(2H,m), 3.90 to 4.15(1H,m), 4.42(2H,s), 4.42(1H,s), 4.43(1H,s), 4.66(0.5H,d,13 Hz), 4.70(1H,s), 4.94(0.5H,d,13 Hz), 5.22(1H,m), 5.45(1H,m).
$[\alpha]_D^{24} -29.7°$ (c 0.22, CHCl$_3$).

Elemental Analysis for C$_{31}$H$_{44}$NO$_{10}$SCl.H$_2$O : Calcd. C:55.06%, H:6.86%, N:2.07%, Found C:55.28%, H:6.65%, N:1.84%.

EXAMPLE 78

1-Benzylmethylsulfoniomethyl-4-chloroacetylcarbamoyloxy-2-(1,2-epoxy-1,5-dimethyl-4-hexenyl)-3-methoxycyclohexanol hydrogen oxalate As in Example 75, from 1-benzylmethylsulfoniomethyl-4-chloroacetylcarbamoyloxy-2-(1,2-epoxy-2-(1,2-epoxy-1,5-dimethyl-4-hexenyl)-3-methoxycyclohexanol bromide (200 mg) was obtained 1-benzylmethylsulfoniomethyl-4-chloroacetylcarbamoyloxy-2-(1,2-epoxy-1,5-dimethyl-4-hexenyl)-3-methoxycyclohexanol hydrogen oxalate (151 mg: yield 74%) as colorless powder.

NMR spectrum (δ value; CD$_3$OD): 1.42(1.5H,s), 1.43(1.5H,s), 1.68(1.5H,s), 1.74(3H,s), 1.60 to 2.60(7H,m), 2.80(1.5H,s), 3.00(1.5H,s), 3.11(1H,t,6 Hz), 3.32(1.5H,s), 3.34(1.5H,s), 3.45(2H,m), 3.90 to 4.15(1H,m), 4.42(2H,s), 4.42(1H,s), 4.43(1H,s), 4.66(0.5H,d,13 Hz), 4.70(1H,s), 4.94(0.5H,d,13 Hz), 5.22(1H,m), 5.45(1H,m).
$[\alpha]_D^{24} -28.4°$ (c 0.21, CHCl$_3$).

Elemental Analysis for C$_{29}$H$_{40}$NO$_{10}$SCl.H$_2$O: Calcd. C:53.74%, H:6.53%, N:2.16%, Found C:54.49%, H:6.41%, N:2.10%.

EXAMPLE 79

2-(1,2-Epoxy-1,5-dimethyl-4-hexenyl)-1-(2-hydroxymethylbenzyl)thiomethyl-3-methoxy-1,4-cyclohexanediol To an about 14% methanol solution (6 ml) of sodium methoxide were added, under ice-cooling, 2-mercaptomethylbenzylalcohol (655 mg) and fumagillol (1.00 g). The mixture was stirred for one hour at room temperature, to which was added water to suspend the reaction. The product was extracted with ethyl acetate, The extract solution was washed with a saturated aqueous solution of sodium chloride, then dried over anhydrous magnesium sulfate. The solvent was distilled off under reduced pressure, and the residue was purified by means of a silica gel column chromatography (carrier 30 g, developing solvent : ethyl acetate - hexane=2:1) to give 2-(1,2-epoxy-1,5-dimethy-4-hexenyl)-1-(2-hydroxymethylbenzyl)thiomethyl-3-methoxy-1,4-cyclohexanediol (1.43 g : yield 92%) as a colorless oily substance.

NMR spectrum (δ value; CDCl$_3$) 1.39(3H,s), 1.66(3H,s), 1.75(3H,s), 1.55 to 1.85(4H,m), 2.00 to 2.55(3H,m), 2.84(1H,d,13 Hz), 2.93(1H,d,13 Hz), 2.94(1H,t,6 Hz), 3.28(1H,m), 3.32(3H,s), 3.86(1H,d,13 Hz), 3.96(1H,d,13 Hz), 4.20(1H,m), 4.77(2H,br d,6 Hz), 5.19(1H,m), 7.20 to 7.50(4H,m).

EXAMPLE 80

2-(1,2-Epoxy-1,5-dimethyl-4-hexenyl)-1-(2-methanesulfonyloxymethylbenzyl)thiomethyl-3-methoxy-1,4-cyclohexanediol In dichloromethane (0.5 ml) were dissolved 2-(1,2-epoxy-1,5-dimethyl-4-hexenyl)-1-(2-hydroxymethylbenzyl)thiomethyl-3-methoxy-1,4-cyclohexanediol (100 mg) and triethylamine (64 μl). To the solution was added dropwise, under ice-cooling, methanesulfonylchloride (20 μl ). The mixture was stirred for 15 minutes, to which was added water to suspend the reaction. The product was extracted with ethyl acetate. The extract solution was washed with a saturated aqueous solution of sodium chloride, which was then dried over anhydrous magnesium sulfate. The solvent was distilled off under reduced pressure. The residue was purified by means of a silica gel column chromatography (carrier 10 g, developing solvent: ethyl acetate - hexane=2:1) to give 2-(1,2-epoxy-1,5-dimethyl-4-hexenyl)-1-(2-methanesulfonyloxymethylbenzyl)thiomethyl-3-methoxy-1,4-cyclohexanediol (98 mg: yield 83%) as a colorless oily product.

NMR spectrum (δ value; CDCl$_3$) 1.40(3H,s), 1.67(3H,s), 1.74(3H,s), 1.45 to 1.90(4H,m), 2.00 to 2.55(3H,m), 2.89(2H,s), 2.93(1H,t,6 Hz), 2.95(3H,s), 3.27(1H,s), 3.33(3H,s), 3.85(1H,d,13 Hz), 3.96(1H,d,13 Hz), 4.21(1H,m), 5.20(1H,m), 5.42(1H,d,12 Hz), 5.49(1H,d,12 Hz), 7.25 to 7.50(4H,m).

EXAMPLE 81

2-(1,2-Epoxy-1,5-dimethyl-4-hexenyl)-(1,3-dihydrobenzo[c]thiophen-2-ylio)methyl-3-methoxy-1,4-cyclohexanediol mesylate In dichloromethane (1 ml) was dissolved 2-(1,2-epoxy-1,5-dimethyl-4-hexenyl)-1-(2-methanesulfonyloxymethylbenzyl)thiomethyl-3-methoxy-1,4cyclohexanediol (900 mg). The solution was stirred for 24 hours at 30° C. The solvent was distilled off under reduced pressure. The residue was pulverized with ether to give 2-(1,2-epoxy-1,5-dimethyl-4-hexenyl)-1-(1,3-dihydrobenzo[c]thiophen-2-ylio)methyl-3-methoxy-1,4-cyclohexanediol mesylate (889 mg: yield 98%) as colorless powder.

NMR spectrum (δ value; CD$_3$OD): 1.28(3H,s), 1.63(3H,s), 1.72(3H,s), 1.50 to 2.45(7H,m), 2.70(3H,s), 3.02(1H,m), 3.34(3H,s), 3.40(1H,m), 3.45(1H,d,13 Hz), 3.89(1H,d,13 Hz), 4.78(1H,d,14 Hz), 4.95 to 5.25(4H,m), 5.49(1H,m), 7.40 to 7.60(4H,m).

EXAMPLE 82

4-(N-Chloroacetylcarbamoyloxy)-2-(1,2-epoxy-1,5-dimethyl-4-hexenyl)-1-(1,3-dihydrobenzo[c]thiophen-2-ylio)methyl-3-methoxycyclohexanol chloride In dichloromethane (2 ml) was dissolved 2-(1,2-epoxy-1,5-dimethyl-4-hexenyl)-1-(1,3dihydrobenzo[c]thiophen-2-ylio)methyl-3-methoxy-1,4cyclohexanediol mesylate (500 mg). To the solution was added dropwise, under ice-cooling, chloroacetylisocyanate (0.25 ml). The mixture was stirred for 15 minutes, to which was added water to suspend the reaction. The product was extracted with ethyl acetate. The extract solution was dried over anhydrous magnesium sulfate, then the solvent was distilled off under reduced pressure. The residue was purified by means of a silica gel column chromatography (carrier 40 g, developing solvent : chloroform-methanol=20:1) to give 4-(N-chloroacetylcarbamoyloxy)-2-(1,2-epoxy-1,5-dimethyl-4-hexenyl)-1-(1,3dihydrobenzo[c]thiophen-2-ylio)methyl-3-methoxycyclohexanol chloride (88 mg: yield 13%) as colorless powder.

NMR spectrum (δ value; CD$_3$OD): 1.28(3H,s), 1.63(3H,s), 1.71(3H,s), 1.50 to 2.45(7H,m), 3.02(1H,m], 3.33(3H,s), 3.51(1H,m), 3.52(1H,d,13 Hz), 3.93(1H,d,13 Hz), 4.23(2H,s), 4.86(1H,d,16 Hz), 5.00 to 5.25(4H,m), 5.49(1H,m), 7.40 to 7.60(4H,m).

[α]$_D^{22}$ −36.8° (c 0.22,CHCl$_3$).

Elemental Analysis for C$_{27}$H$_{37}$NO$_6$SCl$_2$. H$_2$O: Calcd. C:54.73%, H:6.63%, N:2.36%, Found C:54.65%, H:6.64%, N:2.40%:

EXAMPLE 83

2-(1,2-Epoxy-1,5-dimethyl-4-hexenyl)-1-(4-hydroxybutylyl)thiomethyl-3 -methoxy-1,4-cyclohexanediol As in Example 79, 2-(1,2-epoxy-1,5-dimethyl-4-hexenyl)-1-(2-hydroxybutylyl)thiomethyl-3-methoxy-1,4-cyclohexanediol was obtained as a colorless oily product (yield 79%).

NMR spectrum (δ value; CDCl$_3$): 1.46(3H,s), 1.67(3H,s), 1.75(3H,s), 1.45 to 1.90(8H,m), 2.00 to 2.70(5H,m), 2.89(2H,s), 2.97(1H,t,6 Hz), 3.28(1H,m), 3.35(3H,s), 3.66(2H,m), 4.21(1H,m), 5.20(1H,m).

EXAMPLE 84

2-(1,2-Epoxy-1,5-dimethyl-4-hexenyl)-1-(4-methanesulfonyloxybutylyl)thiomethyl-3-methoxy-1,4-cyclohexanediol As in Example 80, 2-(1,2-epoxy-1,5-dimethyl-4-hexenyl)-1-(4-methanesulfonyloxybutylyl)thiomethyl-3-methoxy-1,4-cyclohexanediol as a colorless oily product (yield 92%)

NMR spectrum (δ value; CDCl$_3$): 1.46(3H,s), 1.67(3H,s), 1.74(3H,s), 1.45 to 1.95(4H,m), 2.00 to 2.55(3H,m), 2.64(2H,t,7 Hz), 2.90(2H,s), 2.99(1H,t,6 Hz), 3.02(3H,s), 3.27(1H,m), 3.34(3H,s), 4.23(1H,m), 4.25(2H,t,6 Hz), 5.19(1H,m).

EXAMPLE 85

2-(1,2-Epoxy-1,5-dimethyl-4-hexenyl)-3-methoxy-1-(1-tetrahydrothienylio)methyl-1,4-cyclohexanediol mesylate As in Example 81, 2-(1,2-epoxy-1,5-dimethyl-4-hexenyl)-3-methoxy-1-(1-tetrahydrothienylio)methyl-1,4-cyclohexanediol mesylate was obtained as colorless powder (yield 100%).

NMR spectrum (δ value; CD$_3$OD): 1.43(3H,s), 1.69(3H,s), 1.75(3H,s), 1.55 to 2.55(11H,m), 2.70(3H,s), 3.13(1H,m), 3.35(3H,s), 3.40 to 4.00(7H,m), 4.27(1H,m), 5.24(1H,m).

EXAMPLE 86

4-(N-Chloroacetylcarbamoyloxy)-2-(1,2-epoxy-1,5-dimethyl-4-hexenyl)-3-methoxy-1-(1-tetrahydrothienylio)methylcyclohexanol chloride As in Example 82, 4-(N-chloroacetyl-carbamoyloxy)-2-(1,2-epoxy-1,5-dimethyl-4-hexenyl)-3-methoxy-1-(1-tetrahydrothienylio)methylcyclohexanol chloride was obtained as colorless powder (yield 95%).

NMR spectrum (δ value; CD$_3$OD): 1.43(3H,s), 1.68(3H,s), 1.75(3H,s), 1.60 to 2.55(11H,m), 3.12(1H,t,6 Hz), 3.34(3H,s), 3.40 to 4.05(7H,m), 4.44(2H,s), 5.23(1H,m), 5.47(1H,m).

[α]$_D^{22}$ −46.8° (c 0.20, CHCl$_3$).

Elemental Analysis for C$_{23}$H$_{37}$NO$_8$SCl$_2$.1.5H$_2$O Calcd. C:49.91%, H:? .28%, N:2.58%, Found C:50.07%, H:7.29%, N:2.85%.

EXAMPLE 87

1-(2-Chloromethylbenzyl)thiomethyl-2-(1,2-epoxy-1,5-dimethyl-4-hexenyl)-3-methoxy-1,4-cyclohexanediol In dimethylformamide (0.5 ml) were dissolved 2-(1,2-epoxy-1,5-dimethyl-4-hexenyl)-1-(2-hydroxymethylbenzyl)thiomethyl-3-methoxy-1,4cyclohexanediol (100 mg) and triethylamine (64 μl). To the solution was added, under ice-cooling, lithium chloride (21 mg). To the mixture was added dropwise methanesulfonyl chloride (20 μl), which was stirred for hours, then the reaction was suspended by the addition of water. The product was extracted with ether, and the extract solution was washed with a saturated aqueous solution of sodium chloride, followed by drying over anhydrous magnesium sulfate. The solvent was distilled off under reduced pressure, and the residue was purified by means of a silica gel column chromatography (carrier 10 g, developing solvent : ethyl acetate - hexane=1:2) to give 1-(2-chloromethylbenzyl)thiomethyl-2 -(1,2-epoxy-1,5-dimethyl-4-hexenyl)-3-methoxy-1,4-cyclohexanediol (70 mg: yield 67%) as a colorless oily product.

NMR spectrum (δ value; CDCl$_3$): 1.40(3H,s), 1.66(3H,s), 1.74(3H,s), 1.45 to 1.90(4H,m), 2.00 to 2.55(3H,m), 2.89(2H,s), 2.96(1H,t,6 Hz), 3.27(1H,m), 3.33(3H,s), 3.90(1H,d,13 Hz), 3.99(1H,d,13 Hz), 4.21(1H,m), 4.76(1H,d,12 Hz), 4.83(1H,d,12 Hz), 5.20(1H,m), 7.20 to 7.40(4H,m).

EXAMPLE 88

4-(N-Chloroacetylcarbamoyloxy)-1-(2-chloromethylbenzyl)thiomethyl-2-(1,2-epoxy-1,5-dimethyl-4-hexenyl)-3-methoxycyclohexanol In dichloromethane (1.5 ml) was dissolved 1-(2-chloromethylbenzyl)thiomethyl-2-(1,2-epoxy-1,5-dimethyl-4-hexenyl)-3-methoxy-1,4-cyclohexanediol (300 mg). To the solution was added dropwise, under ice-cooling, chloroacetylisocyanate (84 μl). The mixture was stirred for 15 minutes, to which was added water to suspend the reaction. The product was extracted with ethyl acetate. The extract solution was washed with a saturated aqueous solution of sodium chloride, followed by drying over anhydrous magnesium sulfate. The solvent was distilled off under reduced pressure. The residue was purified by means of a silica gel column chromatography (carrier 30 g, developing solvent : methyl acetate - hexane=1:2) to give 4-(N-chloroacetylcarbamoyloxy)-1-(2-chloromethylbenzyl)thiomethyl-2-(1,2-epoxy-1,5-dimethyl-4-hexenyl)-3-methoxycyclohexanol (302 mg: yield 79%) as colorless powder.

NMR spectrum (δ value; CDCl$_3$): 1.41(3H,s), 1.66(3H,s), 1.73(3H,s), 1.50 to 1.90(4H,m), 2.00 to 2.55(3H,m), 2.87(1H,d,13 Hz), 2.92(1H,t,6 Hz), 2.98(1H,d,13 Hz), 3.29(1H,m), 3.30(3H,s), 3.91(1H,d,13 Hz), 4.50(2H,s), 4.76(1H,d,12 Hz), 4.84(1H,d,12 Hz), 5.17(1H,m), 5.43(1H,m), 7.20 to 7.40(4H,m).

[α]$_D^{22}$ −33.4° (c 0.20, CHCl$_3$).

Elemental Analysis for C$_{27}$H$_{37}$NO$_6$SCl$_2$ Calcd. C:56.44%, H:6.49%, N:2.44%, Found C:56.23%, H:6.55%, N:2.19%

EXAMPLE 89

4-Carbamoyloxy-1-(2-chloromethylbenzyl)thiomethyl-2-(1,2-epoxy-1,5-dimethyl-4-hexenyl)-3-methoxycyclohexanol In methanol (2 ml) was dissolved 4-(N-chloroacetylcarbamoyloxy)-1-(2-chloromethylbenzyl)-thiomethyl-2-(1,2-epoxy-1,5-dimethyl-4-hexenyl)-3-methoxycyclohexanol (193 mg). To the solution was added a standard buffer solution (2 ml) of pH 10, and the mixture was stirred for 5 hours. To the reaction mixture was added water, then the product was extracted with ethyl acetate. The extract solution was washed with a saturated aqueous solution of sodium chloride, which was then dried over anhydrous magnesium sulfate. The solvent was distilled off under reduced pressure, then the residue was purified by means of a silica gel column chromatography (carrier 30 g, developing solvent: methyl acetate - hexane=1:2) to give 4-(carbamoyloxy-1-(2-chloromethylbenzyl)thiomethyl-2-(1,2-epoxy-1,5-dimethyl-4-hexenyl)-3-methoxycyclohexanol (139 mg : yield 83%) as a colorless oily product.

NMR spectrum (δ value; CDCl$_3$): 1.42(3H,s), 1.66(3H,s), 1.74(3H,s), 1.45 to 1.90(4H,m), 2.00 to 2.55(3H,m), 2.87(1H,d,13 Hz), 2.94(1H,t,6 Hz), 2.98(1H,d,13 Hz), 3.27(1H,m), 3.32(3H,s), 3.91(1H,d,13 Hz), 4.01(1H,d,13 Hz), 4.66(2H,br s), 4.76(1H,d,12 Hz), 4.84(1H,d,12 Hz), 5.18(1H,m), 5.31(1H,m), 7.20 to 7.40(4H,m).

[α]$_D^{22}$ −24.7° (c 0.20, CHCl$_3$).

EXAMPLE 90

1-Benzylmethylsulfoniomethyl-4-chloroacetylcarbamoyloxy-2-(1,2-epoxy-1,5-dimethyl-4-hexenyl)-3-methoxycyclohexanol hydrogen L-malate As in Example 75, from 1-benzylmethylsulfoniomethyl-4-chloroacetylcarbamoyloxy-2-(1,2-epoxy-1,5-dimethyl-4-hexenyl)-3-methoxycyclohexanol bromide (200 mg) was obtained 1-benzylmethylsulfoniomethyl-4-chloroacetylcarbamoyloxy-2-(1,2-epoxy-1,5-dimethyl-4-hexenyl)-3-methoxycyclohexanol hydrogen L-malate (220 mg: yield 55%) as colorless powder.

NMR spectrum (δ value; CD$_3$OD): 1.42(1.5H,s), 1.43(1.5H,s), 1.68(1.5H,s), 1.74(3H,s), 1.60 to 2.60(7H,m), 2.52(1H,dd,7 Hz,16 Hz), 2.79(1H,dd,6 Hz,16 Hz), 2.80(1.5H,s), 3.00(1.5H,s), 3.11(1H,t,6 Hz), 3.33(1.5H,s), 3.35(1.5H,s), 3.45(2H,m), 3.90 to 4.15(1H,m), 4.29(1H,dd,6 Hz,7 Hz), 4.42(1H,s), 4.43(1H,s), 4.66(0.5H,d,13 Hz), 4.72(1H,s), 4.94(0.5H,d,13 Hz), 5.22(1H,m), 5.45(1H,m).

[α]$_D^{22}$ −11.3° (c 0.21, CHCl$_3$).

Elemental Analysis for C$_{31}$H$_{44}$NO$_{11}$SCl.1.5H$_2$O: Calcd. C:53.10%, H:6.76%, N:2.00% Found C:53.21%, H:6.55%, N:2.30%

EXAMPLE 91

4-(2-Benzothiazolylthio)thioacetylcarbamoyl-1-chloromethyl-2-(1,2-epoxy-1,5-dimethyl-4-hexenyl)-3-methoxycyclohexanol O-Chloroacetylcarbamoyl fumagillol (200 mg) was dissolved in dimethylformamide (2 ml). To the solution was added 2-mercaptobenzothiazol.sodium salt (141 mg), and the mixture was stirred for 30 minutes. To the reaction mixture was diluted with isopropylether (50 ml), which was washed with a saturated aqueous solution of sodium hydrogencarbonate and a saturated aqueous solution of sodium chloride, followed by drying over anhydrous magnesium sulfate. The solvent was distilled off under reduced pressure. The residue was dissolved in methanol (5 ml), to which was added 1N HCl (1 ml), and the mixture was stirred for 30 minutes. The reaction mixture was diluted with ethyl acetate (50 ml), which was diluted with a saturated aqueous solution of sodium chloride, a saturated aqueous solution of sodium hydrogen carbonate and further with a saturated aqueous solution of sodium chloride, followed by drying over anhydrous magnesium sulfate. The solvent was distilled off under reduced pressure. The residue was purified by means of a silica gel column chromatography (carrier 20 g, developing solvent: ethyl acetate - hexane=1:1) to give 4-(2-benzothiazolylthio)thioacetylcarbamoyl-1-chloromethyl-2-(1,2-epoxy-1,5-dimethyl-4-hexenyl)-3-methoxychlorohexanol (185 mg: yield 65%) as a colorless oily product.

NMR spectrum ($\delta$ value; CDCl$_3$): 1.42(3H,s), 1.65(3H,s), 1.74(3H,s), 1.45 to 1.90(4H,m), 2.00 to 2.55(3H,m), 2.94(1H,t,6 Hz), 3.30(1H,m), 3.33(3H,s), 3.49(1H,d,11Hz), 3.73(1H,d,11Hz), 4.15(1H,d,15 Hz), 4.24(1H,d,15 Hz), 5.18(1H,m), 5.50(1H,m), 7.30 to 7.55(2H,m), 7.79(1H,d,8 Hz), 7.94(1H,d,7 Hz).

Elemental Analysis for C$_{26}$H$_{33}$N$_2$O$_6$S$_2$Cl: Calcd. C:54.87%, H:5.84%, N:4.92%, Found C:54.78%, H:5.75%, N:4.72%.

EXAMPLE 92

2-(1,2-Epoxy-1,5-dimethyl-4-hexenyl)-1-(2-hydroxyethyl)thiomethyl-3-methoxy-1,4-cyclohexanediol As in Example 79, 2-(1,2-epoxy-1,5-dimethyl-4-hexenyl)-1-(2-hydroxyethyl)thiomethyl-3-methoxy-1,4-cyclohexanediol (yield 51%) was obtained as colorless powder.

NMR spectrum ($\delta$ value; CDCl$_3$): 1.46(3H,s), 1.67(3H,s), 1.75(3H,s), 1.50 to 1.90(4H,m), 2.00 to 2.55(3H,m), 2.75 to 3.05(5H,m), 3.29(1H,m), 3.34(3H,s), 3.76(1H,q,6 Hz), 4.22(1H,m), 5.20(1H,m).

EXAMPLE 93

1-(4-Chlorobenzyl)thiomethyl-2-(1,2-epoxy-1,5-dimethyl-4-hexenyl)-3-methoxy-1,4-cyclohexanediol As in Example 21, 1-(4-chlorobenzyl)thiomethyl-2-(1,2-epoxy-1,5-dimethyl-4hexenyl)-3-methoxy-1,4-cyclohexanediol was obtained (yield 86%) as a colorless oily product.

NMR spectrum ($\delta$ value; CDCl$_3$): 1.39(3H,s), 1.66(3H,s), 1.74(3H,s), 1.45 to 1.90(4H,m), 2.00 to 2.55(3H,m), 2.80(2H,s), 3.23(1H,t,6 Hz), 3.29(1H,m), 3.33(3H,s), 3.71(1H,d,13 Hz), 3.75(1H,d,13 Hz), 4.20(1H,m), 5.18(1H,m), 7.26(4H,m).

EXAMPLE 94

2-(1,2-Epoxy-1,5-dimethyl-4-hexenyl)-3-methoxy-4-methylthioacetylcarbamoyloxy-1-methylthiomethylcyclohexanol In dimethylformamide (3 ml) was dissolved 4-O-chloroacetylcarbamoyl-2-(1,2-epoxy-1,5-dimethyl-4-hexenyl)-3-methoxy-1-methylthiomethyl-1,4-cyclohexanediol (500 mg). To the solution was added thiomethoxide (156 mg), and the mixture was stirred for one hour. The reaction mixture was diluted with ether (50 ml), which was washed with a saturated aqueous solution of sodium chloride, followed by drying over anhydrous magnesium sulfate. The solvent was distilled off under reduced pressure. The residue was purified by means of a silica gel column chromatography (carrier 25 g, developing solvent: ethyl acetate - hexane=2:1) to give 2-(1,2-epoxy-1,5-dimethyl-4-hexenyl)-3-methoxy-4-methylthioacetylcarbamoyloxy-1-methylthiomethylcyclohexanol (407 mg: yield 79%) as colorless powder.

NMR spectrum ($\delta$ value; CDCl$_3$): 1.47(3H,s), 1.66(3H,s), 1.73(3H,s), 1.45 to 1.95(4H,m), 2.00 to 2.55(3H,m), 2.19(3H,s), 2.21(3H,s), 2.86(1H,d,13 Hz), 2.90(1H,t,6 Hz), 2.98(1H,d,13 Hz), 3.32(3H,s), 3.33(1H,m), 3.52(1H,d,15 Hz), 3.63(1H,d,15 Hz), 5.19(1H,m), 5.45(1H,m).

EXAMPLE 95

4-Benzylthioacetylcarbamoyloxy-2-(1,2-epoxy-1,5-dimethyl-4-hexenyl)-3-methoxy-1-methylthiomethylcyclohexanol In dimethylformamide (2 ml) was suspended 60% sodium hydride (67 mg), to which was added dropwise benzylmercaptan (0.16 ml). The mixture was stirred for 15 minutes, to which was then added 4-O-chloroacetylcarbamoyl-2-(1,2-epoxy-1,5-dimethyl-4-hexenyl)-3-methoxy-1-methylthiomethyl-1,4-cyclohexanediol (500 mg). The mixture was stirred for further one hour. To the reaction mixture was added water to suspend the reaction, and the product was extracted with ether. The extract solution was washed with a saturated aqueous solution of sodium chloride, followed by drying over anhydrous magnesium sulfate. The solvent was distilled off under reduced pressure, and the residue was purified by means of a silica gel column chromatography (carrier 25 g, developing solvent: ethyl acetate - hexane=1:2) to give 4-benzylthioacetylcarbamoyloxy-2-(1,2-epoxy-1,5-dimethyl-4-hexenyl)-3-methoxy-1-methylthiomethylcyclohexanol (397 mg: yield 66%) as a colorless oily product.

NMR spectrum ($\delta$ value; CDCl$_3$): 1.47(3H,s), 1.66(3H,s), 1.73(3H,s), 1.50 to 1.90(4H,m), 2.00 to 2.55(3H,m), 2.21(3H,s), 2.86(1H,d,13 Hz), 2.94(1H,t,6 Hz), 2.98(1H,d,13 Hz), 3.32(3H,s), 3.33(1H,m), 3.44(1H,d,15 Hz), 3.52(1H,d,15 Hz), 3.79(2H,s), 5.19(1H,m), 5.43(1H,m), 7.20 to 7.45(5H,m).

EXAMPLE 96

1-Bromomethyl-4-chloroacetylcarbamoyloxy-2-(1,2-epoxy-1,5-dimethyl-4-hexenyl)-3-methoxycyclohexanol As in Example 2, from 1-bromomethyl-2-(1,2-epoxy-1,5-dimethyl-4-hexenyl)-3-methoxy-1,4-cyclohexanediol (200 mg) was obtained 1-bromomethyl-4-chloroacetylcarbamoyloxy-2-(1,2-epoxy-1,5-dimethyl-4-hexenyl)-3-methoxycyclohexanol (178 mg : yield 63%) as colorless crystals, m.p. 111° to 112° C.

NMR spectrum ($\delta$ value; CDCl$_3$): 1.47(1H,m), 1.51(3H,s), 1.66(3H,s), 1.74(3H,s), 1.70 to 2.55(7H,m), 2.96(1H,d,6 Hz), 3.29(1H,m), 3.32(3H,s), 3.45(1H,d,10 Hz), 3.75(1H,d,10 Hz), 4.51(2H,s), 5.18(1H,m), 5.45(1H,m).

$[\alpha]_D^{22}$ −97.5° (c 0.20, CHCl$_3$).

Elemental Analysis for C$_{19}$H$_{29}$NO$_6$SBrCl: Calcd. C:47.27%, H:6.05%, N:2.90% Found C:47.18%, H:6.07%, N:2.84%

EXAMPLE 97

4-Amino-2-(1,2-epoxy-1,5-dimethyl-4-hexenyl)-1-(2-hydroxymethylbenzyl)thiomethyl-3-methoxycyclohexanol To an about 7% methanol solution (2.01 ml) of sodium methoxide were added, under ice-cooling, a methanol solution (0.5 ml) of 2-mercaptomethylbenzylalcohol (165 mg) and a methanol solution (0.5 ml) of 6-oxo-6-desoxyfumagillol (300 mg). The mixture was stirred for one hour at room temperature, followed by addition of water to suspend the reaction. The reaction mixture was subjected to extraction with ethyl acetate. The extract solution was washed with a saturated aqueous solution of sodium chloride, then dried over anhydrous magnesium sulfate. The solvent was distilled off under reduced pressure, and the residue was purified by means of a silica gel column chromatography (carrier 30 g, developing solvent: ethyl acetate - hexane =2:1) to give 2-(1,2-epoxy-1,5-dimethyl-4-hexenyl)-1-(2-hydroxymethylbenzyl)thiomethyl-3-methoxy-4-oxocyclohexanol (397 mg: yield 85%) as a colorless oily product.

NMR spectrum ($\delta$ value; $CDCl_3$): 1.39(3H,s), 1.66(3H,s), 1.73(1H,m), 1.74(3H,s), 2.00 to 2.55(4H,m), 2.40(1H,t,6 Hz), 2.65 to 3.05(3H,m), 2.95(1H,d,6 Hz), 3.39(3H,s), 3.84(1H,d,12 Hz), 3.92(2H,d,6 Hz), 4.01(1H,d, 4.77(2H,d,6 Hz), 5.18(1H,m), 7.20 to 7.45(4H,m).

2-(1,2-Epoxy-1,5-dimethyl-4-hexenyl)-1-(2-hydroxymethylbenzyl)thiomethyl-3-methoxy-4oxocyclohexanol (1.07 g) and ammonium acetate (1.86 g) were dissolved in methanol (25 ml). To the solution was added sodium cyanoborohydride (304 mg), and the mixture was stirred for one hour. The solvent was distilled off under reduced pressure, and the residue was dissolved in ethyl acetate (100 ml). The solution was washed with a saturated aqueous solution of sodium hydrogencarbonate and a saturated aqueous solution of sodium chloride, followed by drying over anhydrous magnesium sulfate. The solvent was distilled off under reduced pressure, and the residue was purified by means of a silica gel column chromatography (carrier 40 g, developing solvent: chloroform-methanol-$NH_4OH$=20:1:0.1) to obtain 4-amino-2-(1,2-epoxy-1,5-dimethyl-4-hexenyl)-1-(2-hydroxymethylbenzyl)thiomethyl-3-methoxycyclohexanol (629 mg; yield 58%) as a colorless oily product.

NMR spectrum ($\delta$ value; $CDCl_3$) 1.35 to 1.90(4H,m), 1.39(3H,s), 1.66(3H,s), 1.74(3H,s), 2.05 to 2.55(3H,m), 2.90(2H,s), 2.96(1H,t,6 Hz) 3.25(1H,m), 3.28(3H,s), 3.52(1H,d,13 Hz), 3.99(2H,d,13 Hz), 4.74(1H,d,12 Hz), 4.81(1H,d,12 Hz), 5.19(1H,m), 7.20 to 7.45(4H,m).

EXAMPLE 98

4-(N'-chloroacetylureido)-2-(1,2-epoxy-1,5-dimethyl-4-hexenyl)-1-(2-hydroxymethylbenzyl)thiomethyl-3-methoxycyclohexanol In dichloromethane (20 ml) was dissolved 4-amino-2-(1,2-epoxy-1,5-dimethyl-4-hexenyl)-1-(2-hydroxymethylbenzyl)thiomethyl-3-methoxycyclohexanol (629 mg). To the solution was added dropwise, under ice-cooling, chloroacetyl isocyanate (0.22 ml). The mixture was stirred for 10 minutes, to which was then added water to suspend the reaction. The reaction product was extracted with ethyl acetate. The extract solution was washed with a saturated aqueous solution of sodium chloride and, then, dried over anhydrous magnesium sulfate. The solvent was distilled off, and the residue was purified by means of a silica gel column chromatography (carrier 30 g, developing solvent: ethyl acetate - hexane=3:2) to afford 4-(N'-chloroacetylureido)-2-(1,2-epoxy-1,5-dimethyl-4-hexenyl)-1-(2-hydroxymethylbenzyl)thiomethyl-3-methoxycyclohexanol (514 mg: yield 64%) as a colorless powdery product.

NMR spectrum ($\delta$ value; $CDCl_3$): 1.40(3H,s), 1.45 to 2.55(6H,m), 1.65(3H,s), 1.73(3H.m), 2.65(1H,t,6 Hz), 2.83(1H,d,13 Hz), 2.96(1H,t,6 Hz), 2.97(1H,d,13 Hz), 3.30(3H,s), 3.35(1H,dd,4 Hz,11Hz), 3.86(1H,d,13 Hz), 3.94(1H,d,13 Hz), 4.15(2H,s), 4.47(1H,m), 4.75(1H,dd,6 Hz,13 Hz), 4.81(1H,dd,6 Hz,13 Hz), 5.17(1H,m), 7.20 to 7.45(4H,m), 8.25(2H,m).

EXAMPLE 99

4-(N'-chloroacetylureido)-2-(1,2-epoxy-1,5-dimethyl-4-hexenyl)-1-(2-methanesulfonyloxymethylbenzyl)thiomethyl-3-methoxycyclohexanol In dichloromethane (3 ml) were dissolved 4-(N'-chloroacetylureido)-2-(1,2-epoxy-1,5-dimethyl-4-hexenyl)-1-(2-hydroxymethylbenzyl)thiomethyl-3-methoxycyclohexanol (514 mg) and triethylamine (0.33 ml). To the solution was added dropwise at $-20°$ C. methanesulfonyl chloride (96 µl). The mixture was stirred for 10 minutes, to which was added water to suspend the reaction. The reaction product was extracted with ethyl acetate. The extract solution was washed with a saturated aqueous solution of sodium chloride and, then, dried over anhydrous magnesium sulfate. The solvent was distilled off under reduced pressure to leave 4-(N'-chloroacetylureido)-2-(1,2-epoxy-1,5-dimethyl-4-hexenyl)-1-(2-methanesulfonyloxymethylbenzyl)thiomethyl-3-methoxycyclohexanol (550 mg; yield 98%) as a colorless powdery product.

NMR spectrum ($\delta$ value; $CDCl_3$): 1.40(3H,s), 1.65(3H,s), 1.73(3H,s), 1.45 to 1.95(4H,m), 2.00 to 2.55(3H,m), 2.81(1H,d,14 Hz), 2.94(3H,s), 2.97(1H,d,14 Hz), 2.98(1H,t,6 Hz), 3.30(3H,s), 3.35(1H,m), 3.86(1H,d,13 Hz), 3.96(1H,d,6 Hz), 4.16(3H,br s), 4.48(1H,m), 5.26(1H,m), 5.46(2H,s), 7.15 to 7.55(4H,m), 8.42(1H,m).

EXAMPLE 100

4-(N'-chloroacetylureido)-2-(1,2-epoxy-1,5-dimethyl-4-hexenyl)-1-(1,3-dihydrobenzo[c]thiophen-2-ylio)methyl-3-methoxycyclohexanol chloride In dichloromethane (2 ml) was dissolved 4-(N'-chloroacetylureido)-2-(1,2-epoxy-1,5-dimethyl-4-hexenyl)-1-(2 -methanesulfonyloxymethylbenzyl)thiomethyl-3-methoxycyclohexanol (450 mg). The solution was stirred for 24 hours at 30° C. The solvent was distilled off under reduced pressure. To the residue was added water, to which was added sodium chloride to perform salting out. The product was extracted with ethyl acetate. The extract solution was dried over anhydrous magnesium sulfate. The solvent was then distilled off under reduced pressure. To the residue was added ether to cause pulverization to give 4-(N'-chloroacetylureido)-2-(1,2-epoxy-1,5-dimethyl-4-hexenyl)-1-(1,3-dihydrobenzo[c]thiophen-2-ylio)methyl-3-methoxycyclohexanol chloride (293 mg: yield 71%) as a colorless powdery product.

NMR spectrum ($\delta$ value; $CD_3OD$): 1.31(3H,s), 1.64(3H,s), 1.72(3H,s), 1.55 to 2.45(7H,m), 3.07(1H,t,7

Hz), 3.31(3H,s), 3.52(1H,d,13 Hz), 3.56(1H,dd,4 Hz,10 Hz), 3.91(1H,d,13 Hz), 4.19(2H,s), 4.42(1H,m), 4.81(1H,d,16 Hz), 4.95 to 5.25(4H,m), 7.40 to 7.60 (4H,m).

$[\alpha]_D^{22}$ −31.8° (c 0.21, CHCl$_3$).

Elemental Analysis for C$_{27}$H$_{38}$N$_2$O$_5$SCl$_2$.0.5H$_2$O : Calcd.: C:55.66%, H:6.75%, N:4.81%, Cl:12.17%, S:5.50% Found : C:55.50%, H:6.73%, N:4.63%, Cl:11.65%, S:5.84%

EXAMPLE 101

2-(1,2-Epoxy-1,5-dimethyl-4-hexenyl)-1-(3,4,5,6-tetrafluoro-2-hydroxymethylbenzyl)thiomethyl-3-methoxy-1,4-cyclohexanediol As in Example 79, from fumagillol (249 mg) was obtained 2-(1,2-epoxy-1,5-dimethyl-4-hexenyl)-1-(3,4,5,6-tetrafluoro-2-hydroxymethylbenzyl)thiomethyl-3-methoxy-1,4-cyclohexanediol (350 mg: yield 77%) as a colorless oily product.

NMR spectrum (δ value; CDCl$_3$): 1.40(3H,s), 1.66(3H,s), 1.75(3H,s), 1.75(3H,s), 1.55 to 1.85(4H,m), 2.00 to 2 50(3H,m), 2.89(1H,d,13 Hz), 2.92(1H,t,7 Hz), 2.97(1H,d,13 Hz), 3.20(1H,m), 3.31(3H,s), 3.88(1H,dd,2 Hz,13 Hz), 4.03(1H,dd,1Hz,13 Hz), 4.19(1H,m), 4.77(2H,m), 5.18(1H,m).

EXAMPLE 102

2-(1,2-Epoxy-1,5-dimethyl-4-hexenyl)-1-(3,4,5,6-tetrafluoro-2-methanesulfonyloxymethylbenzyl)thiomethyl-3-methoxy-1,4-cyclohexanediol As in Example 80, from 2-(1,2-epoxy-1,5-dimethyl-4-hexenyl)-1-(3,4,5,6-tetrafluoro-2-hydroxymethylbenzyl)thiomethyl-3-methoxy-1,4-cyclohexanediol (300 mg) was obtained 2-(1,2-epoxy-1,5dimethy-1,4-hexenyl)-1-(3,4,5,6-tetrafluoro-2-methanesulfonyloxymethylbenzyl)thiomethyl-3-methoxy-1,4-cyclohexanediol (330 mg: yield 95%) as a colorless oily product.

NMR spectrum (δ value; CDCl$_3$): 1.41(3H,s), 1.66(3H,s), 1.74(3H,s), 1.55 to 1.85(4H,m), 2.00 to 2.50(3H,m), 2.90(1H,d,13 Hz), 2.97(1H,t,7 Hz), 3.02(1H,d,13 Hz), 3.08(3H,s), 3.25(1H,m), 3.94(1H,dd,2 Hz,13 Hz), 4.02(1H,dd,2 Hz,13 Hz), 4.21(1H,m), 5.19(1H,m), 5.46(1H,br s).

EXAMPLE 103

2-(1,2-Epoxy-1,5-dimethyl-4-hexenyl)-1-(6-hydroxymethyl-3-cyclohexenylmethyl)thiomethyl-3-methoxy-1,4-cyclohexanediol As in Example 79, from fumagillol (700 mg) was obtained 2-(1,2-epoxy-1,5-dimethyl-4-hexenyl)-1-(6-hydroxymethyl-3-cyclohexenylmethyl)thiomethyl-3-methoxy-1,4-cyclohexanediol (988 mg: yield 90%) as a colorless oily product.

NMR spectrum (δ value; CDCl$_3$): 1.46(3H,s), 1.67(3H,s), 1.75(3H,s), 1.55 to 2.80(13H,m), 2.96(1H,d,13 Hz), 2.98(1H,t,6 Hz), 3.30(1H,m), 3.24(3H,s), 3.45 to 3.75(4H,m), 4.22(1H,m), 5.20(1H,m), 5.63(2H,br s).

EXAMPLE 104

4-(N-chloroacetylcarbamoyloxy)-2-(1,2-epoxy-1,5-dimethyl-4-hexenyl)-1-(1,3,3a,4,7,7ahexahydrobenzo[c]thiophen-2-ylio)methyl-3-methoxycyclohexanol chloride In dichloromethane (3 ml) were dissolved 2-(1,2-epoxy-1,5-dimethyl-4-hexenyl)-1-(6-hydroxymethyl-3-cyclohexenylmethyl)thiomethyl-3-methoxy-1,4-cyclohexanediol (500 mg) and triethylamine (0.32 ml).

To the solution was added dropwise at −20° C. methaneshlfonyl chloride (92 μl). The mixture was warmed to room temperature, which was stirred for one hour. The mixture was then cooled on an ice-bath, to which was added dropwise chloroacetyl isocyanate (0.29 ml). The mixture was stirred for 10 minutes, to which was then added water to suspend the reaction. To the reaction mixture was added sodium chloride to perform salting-out, followed by extraction with ethyl acetate. The extract solution was dried over anhydrous magnesium sulfate. The solvent was then distilled off under reduced pressure. The residue was purified by means of a silica gel column chromatography (carrier 20 g, developing solvent: chloroform-methanol=15:1) to afford 4-(N-chloroacetylcarbamoyloxy)-2-(1,2-epoxy-1,5-dimethyl-4-hexenyl)-1-(1,3,3a,4,7,7ahexahydrobenzo[c]thiophen-2-ylio)methyl-3-methoxycyclohexanol chloride (214 mg: yield 27%) as a colorless powdery product.

NMR spectrum (δ value; CD$_3$OD): 1.45(3H,s), 1.68(3H,s), 1.75(3H,s), 1.70 to 2.30(8H,m), 2.35 to 2.55(3H,m), 2.85 to 3.05(2H,m), 3.12(1H,t,6 Hz), 3.34(3H,s), 3.40 to 3.75(5H,m), 3.84(1H,dd,6 Hz,13 Hz), 4.13(1H,d,13 Hz), 4.43(2H,s), 5.24(1H,m), 5.47(1H,m), 5.70(2H,br s).

EXAMPLE 105

4-amino-2-(1,2-epoxy-1,5-dimethyl-4-hexenyl)-1-(6-hydroxymethyl-3-cyclohexenylmethyl)thiomethyl-3-methoxycyclohexanol As in Example 97, from 6-oxo-6-desoxyfumagillol, by way of 2-(1,2-epoxy-1,5-dimethyl-4-hexenyl)-1-(6-hydroxymethyl-3-cyclohexenylmethyl)thiomethyl-3-methoxy-4-oxocyclohexanol, was obtained 4-amino-2-(1,2-epoxy-1,5-dimethyl-4-hexenyl)-1-(6-hydroxymethyl-3-cyclohexenylmethyl)thiomethyl-3-methoxycyclohexanol as a colorless oily product.

2-(1,2-epoxy-1,5-dimethyl-4-hexenyl)-1-(6-hydroxymethyl-3-cyclohexenylmethyl)thiomethyl-3-methoxy-4-oxocyclohexanol:

NMR spectrum (δ value; CDCl$_3$): 1.46(3H,s), 1.67(3H,s), 1.74(3H,s), 1.65-2.85(13H,m), 2.85L 20 3.10(4H,s), 3.41(3H,s), 3.45-3.75(2H,m), 3.87(1H,d,12 Hz), 3.99(1H,dd,2 Hz,8 Hz), 5.19(1H,m), 5.63(2H,d,2 Hz).

4-amino-2-(1,2-epoxy-1,5-dimethyl-4-hexenyl)-1-(6-hydroxymethyl-3-cyclohexenylmethyl)thiomethyl-3-methoxycyclohexanol:

NMR spectrum (δ value; CDCl$_3$): 1.45(1.5H,s), 1.46(1.5H,s), 1.66(3H,s), 1.74(3H,s), 1.50-3.05(18H,m), 3.25(1H,m), 3.29(3H,s), 3.45-3.75(3H,m), 5.19(1H,m), 5.62(2H,brs).

EXAMPLE 106

4-(N′-chloroacetylureido)-2-(1,2-epoxy-1,5-dimethyl-4-hexenyl)-1-(6-hydroxymethyl-3-cyclohexenylmethyl)-thiomethyl-3-methoxycyclohexanol As in Example 98, from 4-amino-2-(1,2-epoxy-1,5-dimethyl-4-hexenyl)-1-(6-hydroxymethyl-3-cyclohexenylmethyl)thiomethyl-3-methoxycyclohexanol (870 mg) was obtained 4-(N′-chloroacetylureido)-2-(1,2-epoxy-1,5-dimethyl-4-hexenyl)-1-(6-hydroxymethyl-3-cyclohexenylmethyl)thiomethyl-3-methoxycyclohexanol (588 mg: yield 53%) as a colorless oily product.

NMR spectrum (δ value; CDCl₃): 1.46(1.5H,s), 1.48(1.5H,s), 1.66(3H,s), 1.74(3H,s), 1.50-3.80(18H,m), 3.31(1.5H,s), 3.32(1.5H,s), 3.25-3.90(4H,m), 4.13(1H,s), 4.14(1H,s), 4.50(1H,m), 5.17(1H,m), 5.62(2H,brs), 8.43(1H,m), 8.59(1H,m).

EXAMPLE 107

4-(N'-chloroacetylureido)-2-(1,2-epoxy-1,5-dimethyl-4-hexenyl)-1-(1,3,3a,4,7,7a-hexahydrobenzo[c]thiophen-2-ylio)methyl-3-methoxycyclohexanol chloride In dichloromethane (5 ml) were dissolved 4-(N'-chloroacetylureido)-2-(1,2-epoxy-1,5-dimethyl-4-hexenyl)-1-(6-hydroxymethyl-3-cyclohexenylmethyl) thiomethyl-3-methoxycyclohexanol (500 mg) and triethylamine (0.25 ml). To the solution was added dropwise at −20° C. methanesulfonyl chloride (69 μl ). The mixture was warmed to room temperature, which was stirred for one hour. The solvent was distilled off under reduced pressure and the residue was dissolved in water. Insolubles were removed off by decantation and to the obtained supernatant liquid was added sodium chloride, followed by salting out. The product was extracted with ethyl acetate. The extract solution was dried over anhydrous magnesium sulfate, then the solvent was distilled off under reduced pressure. The residue was purified by means of a silica gel column chromatography (carrier 20 g, developing solvent : chloroform - methanol=15:1) to give 4-(N'-chloroacetylureido)-2-(1,2-epoxy-1,5-dimethyl-4-hexenyl)-1-(1,3,3a,4,7,7ahexahydrobenzo[c]thiophen-2-ylio)methyl-3-methoxycyclohexanol chloride (290 mg: yield 56%) as colorless powder.

NMR spectrum (δ value; CD₃OD): 1.47(3H,s), 1.68(3H,s), 1.75(3H,s), 1.55-2.30(8H,m), 2.35-2.55(3H,m), 2.85-3.05(2H,m), 3.15(1H,t,6 Hz), 3.33(3H,s), 3.50-3.65(5H,m), 3.70(1H,d,13 Hz), 3.82(1H,dd,6 Hz,13 Hz), 4.13(1H,d,13 Hz), 4.19(2H,s), 4.43(1H,m), 5.23(1H,m), 5.70(2H,brs).

Elemental Analysis for $C_{27}H_{42}N_2O_5SCl_2 \cdot 0.75H_2O$: Calcd. C:54.86%, H:7.42%, N:4.74%, Found C:54.95%, H:7.76%, N:5.00%,

What is claimed is:

1. A compound of the formula:

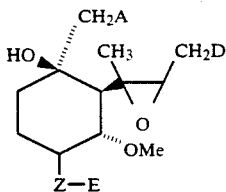

wherein A is halogen, $-N(O)_mR^1R^2$, $-N{\oplus}R^1R^2R^3X{\ominus}$, $-S(O)_nR^1$ or $S{\oplus}(O)_mR^1R^2X\beta$; and in which $R^1$, $R^2$ and $R^3$ independently are (1) a $C_{1-6}$alkyl, $C_{2-6}$alkenyl, $C_{2-6}$alkynyl, $C_{3-6}$cycloalkyl, $C_{3-6}$cycloalkenyl, $C_{7-13}$aralkyl or $C_{6-10}$aryl group, each of which is unsubstituted or substituted by (i) $C_{1-6}$alkyl, (ii) $C_{2-6}$alkenyl, (iii) $C_{3-6}$alkynyl, (iv) $C_{3-6}$cycloalkyl, (v) $C_{3-6}$cycloalkenyl, (vi) $C_{6-10}$aryl, (vii) amino, (viii) $C_{1-6}$alkylamino, (ix) di-$C_{1-6}$alkylamino, (x) azido, (xi) nitro, (xii) halogen, (xiii) hydroxyl, (xiv) $C_{1-4}$alkoxy, (xv) $C_{6-10}$aryloxy, (xvi) $C_{1-6}$alkylthio, (xvii) $C_{6-10}$arylthio, (xviii) cyano, (xix) carbamoyl, (xx) carboxyl, (xxi) $C_{1-4}$alkoxy-carbonyl, (xxii) $C_{7-11}$aryloxycarbonyl, (xxiii) carboxy-$C_{1-4}$alkoxy, (xxiv) $C_{1-6}$alkanoyl, (xxv) $C_{7-11}$aroyl, (xxvi) $C_{6-10}$arylsulfonyl, (xxvii) $C_{1-6}$alkylsulfinyl, (xxviii) $C_{6-10}$arylsulfinyl, (xxix) $C_{1-6}$alkylsufonyl, (xxx) a 5- or 6-membered heterocyclic group containing 1 to 4 hetero atoms of nitrogen, oxygen and/or sulfur, (xxxi) a 5- or 6-membered heterocyclic-carbonyl group containing 1 to 4 hetero atoms of nitrogen, oxygen and/or sulfur, or (xxxii) a 5- or 6-membered heterocyclic-thio group containing 1 to 4 hetero atoms of nitrogen, oxygen and/or sulfur which may be fused with a benzene ring, wherein groups (i) to (xxxii) are unsubstituted or further substituted by one to three groups of any of groups (i) to (xxxii) as defined above, or (2) a 5- or 6-membered heterocyclic group containing 1 to 4 hetero atoms of nitrogen, oxygen and/or sulfur, which is unsubstituted or substituted by the substituent(s) on the $C_{1-6}$alkyl, $C_{2-6}$alkenyl, $C_{2-6}$alkynyl, $C_{3-6}$cycloalkyl, $C_{3-6}$cycloalkenyl, $C_{7-13}$aralkyl or $C_{6-10}$aryl group as defined in (1) of $R^1$, $R^2$ and $R^3$, and which may be fused with benzene, pyridine or cyclohexane; $X\oplus$ is a counter anion; m is an integer of 0 or 1; n is an integer of 0 to 2; $R^1$ and $R^2$ together with an adjacent nitrogen atom may form a 4 to 7 membered nitrogen-containing heterocyclic group which is unsubstituted or substituted by the substituent(s) on the $C_{1-6}$alkyl, $C_{2-6}$alkenyl, $C_{2-6}$alkynyl, $C_{3-6}$cycloalkyl, $C_{3-6}$cycloalkenyl, $C_{7-13}$aralkyl or $C_{6-10}$aryl groups as defined in (1) of $R^1$, $R^2$ and $R^3$, and which may be fused with benzene, pyridine, pyrazine, pyridazine, cyclohexane or cyclohexene, or $R^1$ and $R^2$ together with an adjacent sulfur atom may form a 4 to 7-membered sulfur-containing heterocyclic group which is unsubstituted or substituted by the substituent(s) on the $C_{1-6}$alkyl, $C_{2-6}$alkenyl, $C_{2-6}$alkynyl, $C_{3-6}$cycloalkyl, $C_{3-6}$cycloalkenyl, $C_{7-13}$aralkyl or $C_{6-10}$aryl groups as defined in (1) of $R^1$, $R^2$ and $R^3$, and which may be fused with benzene, pyridine, pyrazine, pyridazine, cyclohexane or cyclohexene; Z is $-NR^4$ wherein $R^4$ is hydrogen, or a $C_{1-6}$alkyl or $C_{6-10}$aryl group, each of which is unsubstituted or substituted by the substituent(s) on the $C_{1-6}$alkyl, $C_{2-6}$alkenyl, $C_{2-6}$alkynyl, $C_{3-6}$cycloalkyl, $C_{3-6}$cycloalkenyl, $C_{7-13}$aralkyl or $C_{6-10}$aryl groups as defined in (1) of $R^1$, $R^2$ and $R^3$; D is 2-methyl-1-propenyl or isobutyl; E is (i) hydrogen, (ii) a group as defined in (1) of $R^1$, $R^2$ and $R^3$, or (iii) a $C_{1-10}$alkanoyl, $C_{7-11}$aroyl, 5- or 6-membered heterocyclic carbonyl containing 1 to 4 hetero atoms of nitrogen, oxygen and/or sulfur, carbamoyl, thiocarbamoyl, $C_{6-10}$arylsulfonyl, $C_{1-6}$alkylsulfonyl, sulfamoyl, $C_{2-7}$alkoxycarbonyl or $C_{7-11}$aryloxycarbonyl group which is unsubstituted or substituted by the substituent(s) on the $C_{1-6}$alkyl, $C_{2-6}$alkenyl, $C_{2-6}$alkynyl, $C_{3-6}$cycloalkyl, $C_{3-6}$cycloalkenyl, $C_{7-13}$aralkyl or $C_{6-10}$aryl groups as defined in (1) of $R^1$, $R^2$ and $R^3$, provided that, when A is chlorine, E is a group of (ii), or a group of (iii) excepting dinitrobenzoyl; or a salt thereof.

2. The compound according to claim 1, wherein A is $N(O)_mR^1R^2$, $N\oplus^1R^2R^3X\ominus$, $S(O)_nR^1$ or $S\oplus(O)_mR^1R^2X\ominus$ where $R^1$, $R^2$, $R^3$, $X\ominus$, m and n are the same as defined above in claim 1.

3. The compound according to claim 1, wherein A is $N(O)_mR^1R^2$ in which $R^1$ and $R^2$ are each $C_{1-6}$alkyl, or together with the adjacent nitrogen atom form a pyrrolidine, piperidine, morpholine or 4-methylpiperazine, and m is 0 or 1.

4. The compound according to claim 1, wherein A is $N\oplus R^1R^2R^3X\ominus$ is which $R^1$, $R^2$ and $R^3$ are each $C_{1-6}$alkyl, or $R^1$ and $R^2$ together with the adjacent nitrogen atom form a pyrrolidine, piperidine, morpholine or 4-methylpiperazine and $R^3$ is $C_{1-6}$alkyl, and $X\ominus$ is an inorganic counter anion.

5. The compound according to claim 1, wherein A is $S(O)nR^1$ in which $R^1$ is (1) $C_{1-6}$alkyl which is unsubstituted or substituted with (i) hydroxyl, (ii) mesyloxy or (iii) phenyl which is unsubstituted or substituted with halogen, hydroxymethyl or mesyloxymethyl, (2) $C_{2-6}$alkenyl, (4) phenyl, (4) naphthyl, (5) pyridyl or (6) quinolyl, and n is 0 or 1.

6. The compound according to claim 1, wherein A is $S\oplus(O)mR^1R^2X\ominus$ in which $R^1$ is $C_{1-6}$alkyl and $R^2$ is $C_{1-6}$alkyl which is unsubstituted or substituted with (i) phenyl, (ii) $C_{2-6}$alkenyl, (iii) $C_{2-6}$alkynyl or (iv) phenyl which is substituted with halogen or $C_{1-6}$alkyl, or $R^1$ and $R^2$ together with the adjacent sulfur atom form tetrahydrothiophene, thioxane, dihydrobenzenthiophene, hexahydrobenzothiophene, perhydrobenzothiophene, tetrahydrobenzothiophene, dihydrothienopyridine, dihydrothienopyrazine, dihydrothienopyridazine, m is 0 and $X\oplus$ is organic or inorganic counter anion.

7. The compound according to claim 1, wherein D is 2-methyl-1propenyl.

8. The compound according to claim 1, wherein E is hydrogen or $C_{1-6}$alkyl.

9. The compound according to claim 1, wherein E is $C_{1-6}$alkanoyl, $C_{7-11}$aroyl, 5- or 6-membered heterocyclic carbonyl containing 1 to 4 of nitrogen, oxygen and/or sulfur atoms, carbamoyl, thiocarbamoyl, $C_{6-10}$arylsulfonyl, $C_{1-6}$alkylsulfonyl, sulfamoyol, $C_{2-7}$alkoxycarbonyl, or $C_{7-11}$aryloxycarbonyl, each of which is unsubstituted or substituted by the substituent(s) on the $C_{1-6}$alkyl, $C_{2-6}$alkenyl, $C_{2-6}$alkynyl, $C_{3-6}$cycloalkyl, $C_{3-6}$cycloalkenyl, $C_{7-13}$aralkyl or $C_{6-10}$aryl groups as defined in (1) of $R^1$, $R^2$ and $R^3$ of claim 1.

10. The compound according to claim 1, wherein E is benzoyl; carbamoyl; $C_{1-6}$alkylcarbamoyl which is unsubstituted or substituted with halogen; $C_{1-6}$alkanoylcarbamoyl which is unsubstituted or substituted with halogen, $C_{1-6}$alkylthio, $C_{6-11}$arylthio, $C_{7-13}$aralkylthio, quinolylthio or benzothiazolythio; $C_{2-6}$alkenylcarbamoyl; $C_{6-11}$arylcarbamoyl; morpholyl; $C_{6-11}$arylsulfonyl; $C_{1-6}$alkylsulfonyl or $C_{7-11}$aryloxycarbonyl.

11. The compound according to claim 1, wherein A is $S\oplus R^1R^2X\ominus$ wherein $R^1$ is $C_{1-6}$alkyl and $R^2$ is $C_{1-6}$alkyl which is unsubstituted or substituted with phenyl, or $R^1$ and $R^2$ together with the adjacent sulfur atom form dihydrobenzothiophene and $X\ominus$ is halogen anion; Z is NH; D is 2-methyl-1-propenyl; and E is hydrogen or $C_{1-6}$alkanoyl which is unsubstituted or substituted with halogen.

12. The compound according to claim 1, which is 4-(N'-chloroacetylureido)-2-(1,2-epoxy-1,5-dimethyl-4-hexenyl)-1-(1,3-dihydrobenzothiophen-2-ylio)methyl-3-methoxycyclohexanol chloride.

13. A pharmaceutical composition which contains a compound of the formula:

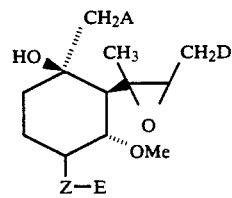

wherein the symbols are as defined in claim 1, or a salt thereof and a pharmaceutically acceptable carrier or excipient therefore.

14. A method of inhibiting or treating tumor which comprises administering to mammal a therapeutically effective amount of a compound of the formula

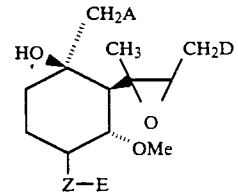

wherein the symbols are as defined in claim 1, or a pharmaceutically acceptable salt, optionally with a pharmaceutically acceptable carrier or excipient therefor.

* * * * *